United States Patent [19]
Suzuki et al.

[11] Patent Number: 5,543,415
[45] Date of Patent: Aug. 6, 1996

[54] ANTIDEPRESSANTS

[75] Inventors: Fumio Suzuki, Mishima; Junichi Shimada, Sunto-gun; Akio Ishii, Sunto-gun; Joji Nakamura, Sunto-gun; Shunji Ichikawa, Tagata-gun; Shigeto Kitamura, Machida; Nobuaki Koike, Sunto-gun, all of Japan

[73] Assignee: Kyowa Hakko Kogyo Co., Ltd., Tokyo, Japan

[21] Appl. No.: 199,142

[22] PCT Filed: Jul. 7, 1993

[86] PCT No.: PCT/JP93/00931

§ 371 Date: Feb. 25, 1994

§ 102(e) Date: Feb. 25, 1994

[87] PCT Pub. No.: WO94/01114

PCT Pub. Date: Jan. 20, 1994

[30] Foreign Application Priority Data

Jul. 8, 1992 [JP] Japan ................... 4-181025

[51] Int. Cl.$^6$ .................. A61K 31/52; A61K 31/505
[52] U.S. Cl. ............................ 514/263; 514/267
[58] Field of Search ............... 514/263; 544/267

[56] References Cited

U.S. PATENT DOCUMENTS 3,641,010  2/1972  Schweiss et al. ............. 260/240
4,472,387  9/1984  Laruelle et al. ............. 424/180

FOREIGN PATENT DOCUMENTS 0565377  10/1993  European Pat. Off. .
56428    6/1990   Japan .
06976    4/1992   WIPO .

OTHER PUBLICATIONS

Sarges et al, J. Med. Chem., vol. 33, 1990, pp. 2240–2254.
Sarges et al., Chemical Abstracts, vol. 113, No. 7, abstract No. 59110r, 1990.
Erickson et al., J. Med. Chem., vol. 34, No. 4 (1991) 1431–1435.
Kaupp et al., Chem. Ber., vol. 119 (1986) 1525–39.
Chem. Abstracts, 60 (1964) 1741h.
Maj. et al., J. Neural Transmission 52 (1981) 189–197.

Primary Examiner—Marianne M. Cintins
Assistant Examiner—William R. A. Jarvis
Attorney, Agent, or Firm—Fitzpatrick, Cella, Harper & Scinto

[57] ABSTRACT

The present invention relates to an antidepressant containing as an active ingredient a xanthine derivative or a pharmaceutically acceptable salt thereof, the xanthine derivative being represented by Formula (I):

in which $R^1$, $R^2$, and $R^3$ represent independently hydrogen, lower alkyl, lower alkenyl;
$R^4$ represents cycloalkyl, $-(CH_2)_n-R^5$ (in which $R^5$ represents substituted or unsubstituted aryl or a substituted or unsubstituted heterocyclic group; and n is an integer of 0 to 4), or (in which $Y^1$ and $Y^2$ represent independently hydrogen, halogen or lower alkyl; and Z represents substituted or unsubstituted aryl, (in which $R^6$ represents hydrogen, hydroxy, lower alkyl, lower alkoxy, halogen, nitro, or amino; and m represents an integer of 1 to 3), or a substituted or unsubstituted heterocyclic group);
and $X^1$ and $X^2$ represent independently O or S.

2 Claims, No Drawings

ANTIDEPRESSANTS

This application is a 371 of PCT/JP93/00931 filed Jul. 7, 1993.

TECHNICAL FIELD

The present invention relates to an antidepressant containing a xanthine derivative or a pharmaceutically acceptable salt thereof as an active ingredient.

BACKGROUND ART

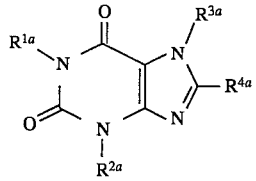

(A)

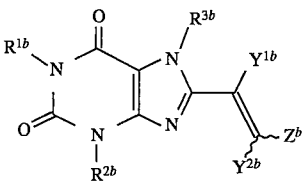

(B)

It is known that adenosine antagonistic action is found in compounds represented by Formula (A) in which $R^{1a}$ and $R^{2a}$ represent propyl, $R^{3a}$ represents hydrogen, and $R^{4a}$ represents substituted or unsubstituted phenyl, aromatic heterocyclic group, cycloalkyl, styryl, or phenylethyl [J. Med. Chem., 34, 1431 (1991)]. Further, Japanese Published Unexamined Patent Application No. 26516/72, as cerebral stimulants, compounds represented by Formula (B) in which $R^{1b}$ and $R^{2b}$ independently represent methyl or ethyl, $R^{3b}$ represents methyl, $Y^{1b}$ and $Y^{2b}$ represent hydrogen, and $Z^b$ represents phenyl or 3,4,5-trimethoxyphenyl WO92/06976 discloses, as compounds having an adenosine $A_2$ receptor antagonistic activity and therapeutic effects on asthma and osteoporosis, compounds represented by Formula (B) in which $R^{1b}$ and $R^{2b}$ independently represent hydrogen, propyl, butyl, or allyl, $R^{3b}$ represents hydrogen or lower alkyl, $Y^{1b}$ and $Y^{2b}$ independently represent hydrogen or methyl, and $Z^b$ represents phenyl, pyridyl, imidazolyl, furyl, or thienyl unsubstituted or substituted by 1 to 3 substituents such as lower alkyl, hydroxy, lower alkoxy, halogen, amino, and nitro. Furthermore, other compounds represented by Formula (B) are known. One is 8-styryl caffeine which is a compound of Formula (B) in which $R^{1b}$, $R^{2b}$, and $R^{3b}$ represent methyl, $Y^{1b}$ and Y2b represent hydrogen, and $Z^b$ represents phenyl [Chem. Ber., 119, 1525 (1986)]. Another is a compound of Formula (B) in which $R^{1b}$, $R^{2b}$, and $R^{3b}$ represent methyl, $Y^{1b}$ and $Y^{2b}$ represent hydrogen, and $Z^b$ represents pyridyl, quinolyl, or methoxy-substituted or unsubstituted benzothiazolyl [Chem. Abst., 60, 1741h (1964)]. However, there is no description with regard to the pharmacologic action of any of these compounds.

It is clinically well known that the conventional antidepressant exhibits little effect in a single administration, and the effect is observed after at least about two weeks' consecutive administration. With the conventional antidepressant, the enhancement of clonidine-induced aggressive behavior in mice is observed after at least ten days' consecutive administration [J. Neural Transmission, 52, 189 (1981)].

DISCLOSURE OF THE INVENTION

The present invention relates to an antidepressant containing as an active ingredient a xanthine derivative or a pharmaceutically acceptable salt thereof, the xanthine derivative being represented by Formula (I):

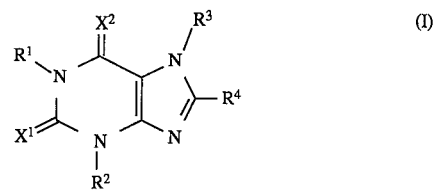

(I)

in which $R^1$, $R^2$, and $R^3$ represent independently hydrogen, lower alkyl, lower alkenyl, or lower alkynyl;
$R^4$ represents cycloalkyl, $—(CH_2)_n—R^5$ (in which $R^5$ represents substituted or unsubstituted aryl or a substituted or unsubstituted heterocyclic group; and n is an integer of 0 to 4), or

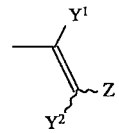

(in which $Y^1$ and $Y^2$ represent independently hydrogen, halogen, or lower alkyl; and Z represents substituted or unsubstituted aryl,

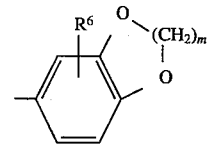

(in which $R^6$ represents hydrogen, hydroxy, lower alkyl, lower alkoxy, halogen, nitro, or amino; and m represents an integer of 1 to 3), or a substituted or unsubstituted heterocyclic group);
and $X^1$ and $X^2$ represent independently O or S.

In the definitions of Compound (I), the lower alkyl means a straight-chain or branched alkyl group having 1 to 6 carbon atoms such as methyl, ethyl, propyl, isopropyl, butyl, isobutyl, sec-butyl, tert-butyl, pentyl, neopentyl, and hexyl. The lower alkenyl means a straight-chain or branched alkenyl group having 2 to 6 carbon atoms such as vinyl, allyl, methacryl, crotyl, 3-butenyl, 2-pentenyl, 4-pentenyl, 2-hexenyl, 5-hexenyl. The lower alkynyl means a straight-chain or branched alkynyl group having 2 to 6 carbon atoms such as ethynyl, propargyl, 2-butynyl, 3-butynyl, 2-pentynyl, 4-pentynyl, 2-hexynyl, 5-hexynyl, 4-methyl-2-pentynyl. The aryl means phenyl or naphthyl. The cycloalkyl means a cycloalkyl group having 3 to 8 carbon atoms such as cyclopropyl, cyclobutyl, cyclopentyl, cyclohexyl, cycloheptyl, and cyclooctyl. Examples of the heterocyclic group are furyl, thienyl, pyrrolyl, pyranyl, thiopyranyl, pyridyl, thiazolyl, imidazolyl, pyrimidyl, triazinyl, indolyl, quinolyl, purinyl, and benzothiazolyl. The halogen includes fluorine, chlorine, bromine, and iodine.

The substituted aryl and the substituted heterocyclic ring each has 1 to 3 independently-selected substituents. Examples of the substituents are lower alkyl, hydroxy, substituted or unsubstituted lower alkoxy, halogen, nitro, amino, lower alkylamino, di (lower alkyl) amino, trifluoromethyl, trifluoromethoxy, benzyloxy, phenyl, and phenoxy. The lower alkyl and the alkyl moiety of the lower alkoxy, lower alkylamino, and all(lower alkyl)amino have the same meaning as the lower alkyl defined above. The halogen has the same meaning as defined above. Examples of the substituent of the substituted lower alkoxy are hydroxy, lower alkoxy, halogen, amino, azide, carboxy, and lower alkoxycarbonyl. The lower alkyl moiety of the lower alkoxy and lower alkoxycarbonyl has the same meaning as the lower alkyl defined above, and the halogen has the same meaning as defined above.

The pharmaceutically acceptable salts of Compounds (I) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, arid phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The processes for producing Compounds (i) are described below. Compounds (I) can also be produced according to the methods described in, for example, Japanese Published Unexamined Patent Application No. 26516/72; J. Med. Chem., 34, 1431 (1991); Chem. Ber., 119, 1525 (1986); and Chem. Abst., 60, 1741h (1964).

Process 1

Compound (I-a) [Compound (I) in which $R^3$ is hydrogen] can be prepared by the following reaction steps:

reactive derivative thereof to give Compound (IV). Examples of the reactive derivative of the carboxylic acid (III) are acid halides such as acid chloride and acid bromide, active esters such as p-nitrophenyl ester and N-oxysuccinimide, commercially available acid anhydrides, acid anhydrides produced by using carbodiimides such as 3-(3-dimethylaminopropyl)-1-ethylcarbodiimide, diisopropyl carbodiimide, and dicyclohexyl carbodiimide, and mixed acid anhydrides with monoethyl carbonate or monoisobutyl carbonate. If the carboxylic acid (III) is used, the reaction is completed in 10 minutes to 5 hours at 50° to 200° C. without using a solvent.

If a reactive derivative of the carboxylic acid (III) is used, the reaction can be carried out according to a conventional method employed in peptide chemistry. That is, Compound (II) and a derivative of the carboxylic acid (III) are allowed to react, preferably in the presence of an additive or a base, to give Compound (IV). Examples of the solvent are halogenated hydrocarbons such as methylene chloride, chloroform, and ethylene dichloride, ethers such as dioxane and tetrahydrofuran, dimethylformamide, dimethylsulfoxide, and water if necessary. An example of the additive is 1-hydroxybenzotriazole. Examples of the base are pyridine, triethylamine, 4-dimethylaminopyridine, and N-methylmorpholine. The reaction is completed in 0.5 to 24 hours at −80° to 50° C. The reactive derivative may be formed in the reaction system and then used without being isolated.

(STEP 2)

Compound (I-a) can be obtained by reaction of Compound (IV) carried out in any of the following manners: in the presence of a base (Method A); by treatment with a dehydrating agent (Method B); or by heating (Method C). In Method A, the reaction is carried out in a solvent in the presence of a base such as an alkali metal hydroxide (e.g. sodium hydroxide and potassium hydroxide). As the solvent, water, lower alcohols such as methanol and ethanol, ethers

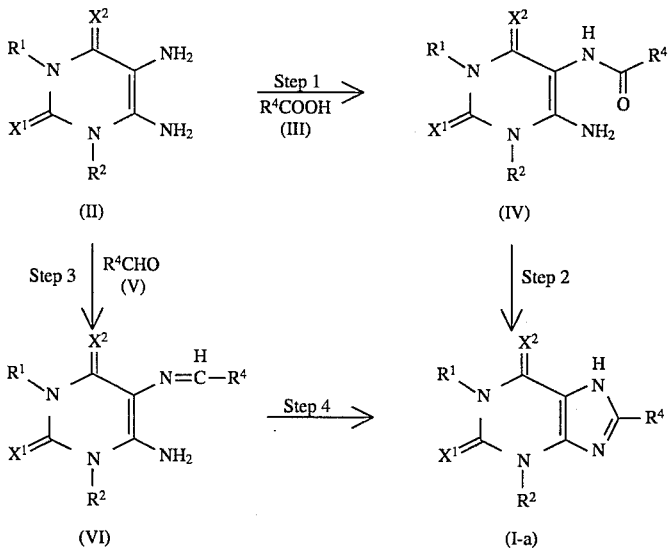

(In the formulae $R^1$, $R^2$, $R^4$, $X^1$, and $X^2$ have the same meanings as defined above.)

(STEP 1)

A uracil derivative (II) obtained by a known method [for example, Japanese Published Unexamined Patent Application No. 42383/84; J. Med. Chem., 32, 1873 (1989)] is allowed to react with either a carboxylic acid (III) or a such as dioxane and tetrahydrofuran, dimethylformamide, dimethylsulfoxide, and the like may be used alone or in combination. The reaction is completed in 10 minutes to 6 hours at 0° to 180° C.

In Method B, the reaction is carried out in an inert solvent or in the absence of a solvent using a dehydrating agent such as a thionyl halide (e.g. thionyl chloride) and a phosphorus oxyhalide (e.g. phosphorus oxychloride). Examples of the inert solvent are halogenated hydrocarbons such as methylene chloride, chloroform and ethylene dichloride, dimethylformamide, and dimethylsulfoxide. The reaction is completed in 0.5 to 12 hours at 0° to 180° C.

In Method C, the reaction is carried out in a polar solvent such as dimethylformamide, dimethylsulfoxide, and Dowtherm A (Dow Chemicals). The reaction is completed in 10 minutes to 5 hours at 50° to 200° C.
(STEP 3)

Compound (II) is allowed to react with an aldehyde (V) to give a Schiff's base (VI). As a reaction solvent, mixtures of acetic acid and a lower alcohol such as methanol and ethanol may be used. The reaction is completed in 0.5 to 12 hours at −20° to 100° C.
(STEP 4)

Compound (VI) is oxidatively cyclized in the presence of an oxidizing agent to form Compound (I-a). Examples of the oxidizing agent are oxygen, ferric chloride, cerium (IV) ammonium nitrate, and diethylazodicarboxylate. Examples of the solvent are lower alcohols such as methanol and ethanol, halogenated hydrocarbons such as methylene chloride and chloroform, and aromatic hydrocarbons such as toluene, xylene, and nitrobenzene. The reaction is completed in 10 minutes to 12 hours at 0° to 180° C.

Process (2)

Compound (I-b) [Compound (I) in which $R^3$ is a group other than hydrogen] can be prepared by the following reaction step.

Compound (I-b) is obtained from Compound (I-a) prepared by Process 1.

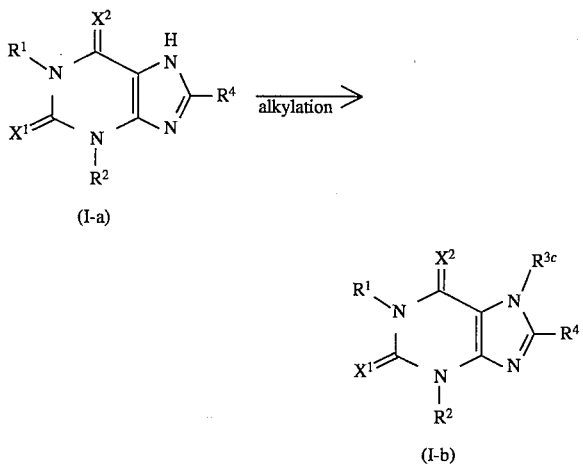

(In the formulae, $R^{3c}$ represents a group other than hydrogen in the definition of $R^3$; and $R^1$, $R^2$, $R^4$, $X^1$, and $X^2$ have the same meanings as defined above.)

Compound (I-b) can be obtained by reaction of Compound (I-a) with an alkylating agent, in the presence of a base if necessary. Examples of the alkylating agent are alkyl halides such as methyl iodide and allyl bromide, dialkyl sulfates such as dimethyl sulfate, sulfonic esters such as allyl p-tolenesulfonate, and diazoalkanes such as diazomethane. Examples of the base are alkali metal carbonates such as sodium carbonate and potassium carbonate, alkali metal hydrides such as sodium hydride, and alkali metal alkoxides such as sodium methoxide and sodium ethoxide. As a reaction solvent, aromatic hydrocarbons such as toluene and xylene, ketones such as acetone and methyl ethyl ketone, dimethylformamide, dimethylsulfoxide, or the like may be used. The reaction is completed in 0.5 to 24 hours at 0° to 180° C.

Process 3

Compound (I-d) [Compound (I) in which Z is phenyl having hydroxy as substituent(s)] can be alternatively prepared by the following reaction step.

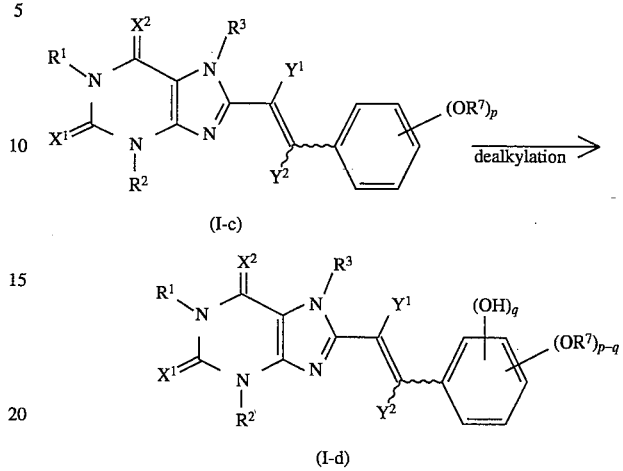

(In the formulae, $R^7$ represents substituted or unsubstituted lower alkyl; p and q are integers of 1 to 3 and p≧q; and $R^1$, $R^2$, $R^3$, $X^1$, $X^2$, $Y^1$, and $Y^2$ have the same meanings as defined above.)

The substituted or unsubstituted lower alkyl in the definition of $R^7$ has the same meaning as defined above.

Compound (I-d) can be obtained by reaction of Compound (I-c) [Compound (I) in which Z is phenyl having lower alkoxy as substituent (s)] obtained by Process 1 or Process 2 with a dealkylating agent. Examples of the suitable dealkylating agent are boron tribromide and the complex thereof with dimethyl disulfide, boron trichloride, iodotrimethylsilane, sodium ethanethiolate, sodium benzenethiolate, and hydrobromic acid. A reaction solvent is selected from aromatic hydrocarbons such as toluene and xylene, halogenated hydrocarbons such as methylene chloride, chloroform, and ethylene dichloride, dimethylformamide, acetic acid, etc. depending upon the kind of the dealkylating agent used. The reaction is completed in 10 minutes to 120 hours at −30° to 140° C.

Process 4

Compound (I-e) [Compound (I) in which Z is phenyl having lower alkoxy as substituent (s)] can be alternatively prepared by the following reaction step.

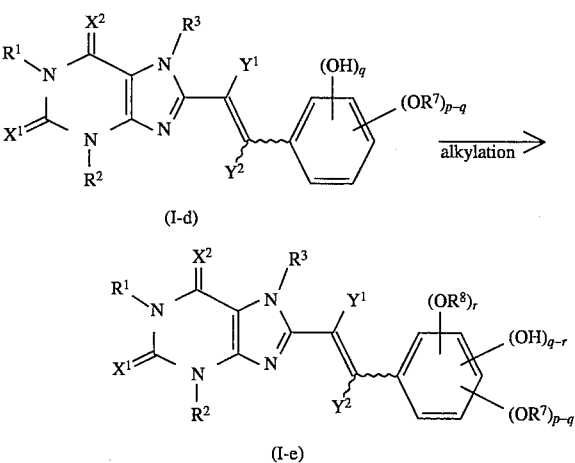

(In the formulae;, $R^8$ represents substituted or unsubstituted lower alkyl; r is an integer of 1 to 3 and q≧r; and $R^1$, $R^2, R^3, R^7, X^1, X^2, Y^1, Y^2$, p, and q have the same meanings as defined above.)

The substituted or unsubstituted lower alkyl in the definition of $R^8$ has the same meaning as defined above.

Compound (I-e) can be obtained from Compound (I-d) according to the method of Process 2.

Process 5

Compound (I-h) [Compound (I) in which Z is phenyl having amino-substituted lower alkoxy as the substituent] can be alternatively prepared by the following reaction step.

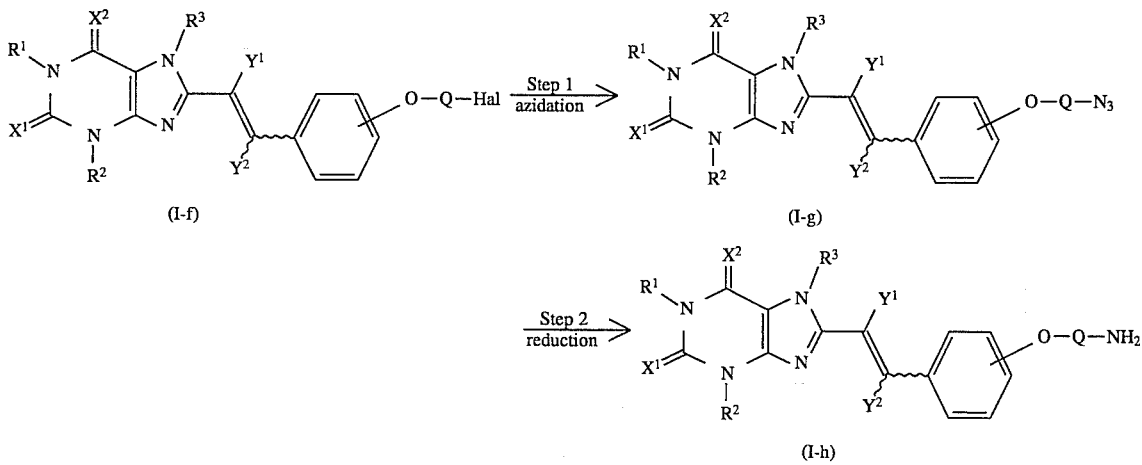

(In the formulae, Q represents lower alkylene; Hal represents chlorine, bromine, or iodine; and $R^1, R^2, R^3, X^1, X^2, Y^1$, and $Y^2$ have the same meanings as defined above.)

The lower alkylene in the definition of Q means a straight-chain or branched alkylene group having 1 to 6 carbon atoms such as methylene, ethylene, propylene, 1-methylethylene, butylene, 1-methylpropylene, 2-methylpropylene, pentylene, and hexylene.

(STEP 1)

Compound (I-g) can be obtained by reaction of Compound (I-f) [Compound (I) in which Z is phenyl having chlorine, bromine, or iodine-substituted lower alkoxy as the substituent] obtained by Process 4 with 5 to 10 equivalents of sodium azide. As a reaction solvent, an inert solvent such as dimethylformamide may be used. The reaction is completed in 1 to 10 hours at 50° to 80° C.

(STEP 2)

Compound (I-h) can be obtained by treatment of Compound (I-g) in an inert solvent such as tetrahydrofuran and dioxane in the presence of 2 to 5 equivalents of a reducing agent such as triphenylphosphine, followed by addition of an excess of water and further treatment for 1 to 10 hours at 50° C. to the boiling point of the solvent used.

Process 6

Compound (I-j) [Compound (I) in which Z is phenyl having carboxy-substituted lower alkoxy as the substituent] can be alternatively prepared by the following reaction step.

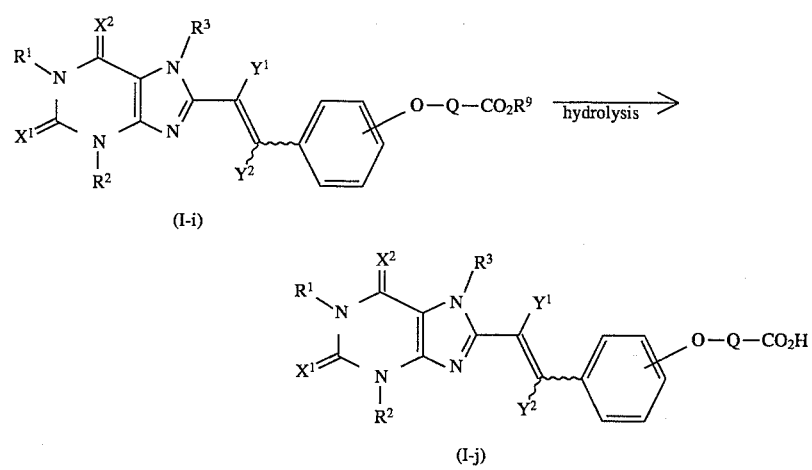

(In the formulae, $R^9$ represents lower alkyl; and $R^1, R^2, R^3$, Q, $X^1, X^2, Y^1$, and $Y^2$ have the same meanings as defined above.)

The lower alkyl in the definition of $R^9$ has the same meaning as defined above.

Compound (I-j) can be obtained by hydrolysis of Compound (I-i) [Compound (I) in which Z is phenyl having lower alkoxycarbonyl-substituted lower alkoxy as the substituent] obtained by Process 4 in the presence of an alkali metal hydroxide such as sodium hydroxide and lithium hydroxide. As a reaction solvent, a mixture of water and an ether such as dioxane and tetrahydrofuran, or a mixture of water and an alcohol such as methanol and ethanol may be used. The reaction is completed in 10 minutes to 12 hours at room temperature to the boiling point of the solvent used.

Process 7

Compound (I-m) [Compound (I) in which Z is phenyl having hydroxy as the substituent (s)] can be alternatively prepared by the following reaction step.

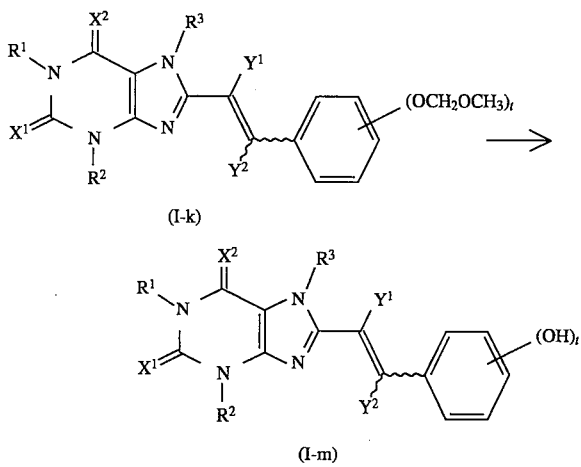

(In the formulae, t is an integer of 1 to 3; and $R^1$, $R^2$, $R^3$, $X^1$, $X^2$, $Y^1$, and $Y^2$ have the same meanings as defined above.)

Compound (I-m) can be obtained by treatment of Compound (I-k) [Compound (I) in which Z is phenyl having methoxymethoxy as the substituent (s)] obtained by Process 1, Process 2, or Process 4 in the presence of hydrogen chloride gas, an aqueous solution of hydrochloric acid, or the like. As a reaction solvent, ethers such as dioxane and tetrahydrofuran, alcohols such as methanol and ethanol, or the like may be used. The reaction is completed in 1 to 20 hours at room temperature to the boiling point of the solvent used.

Process 8

Compound (I-o) [Compound (I) in which $X^2$ is S] can be alternatively prepared by the following reaction step.

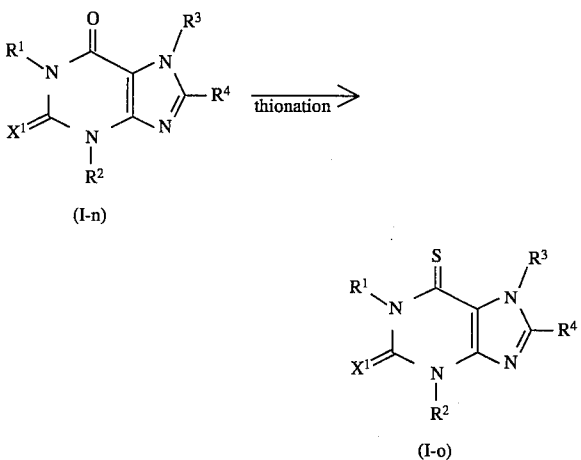

(In the formulae, $R^1$, $R^2$, $R^3$, $R^4$, and $X^1$ have the same meanings as defined above.)

Compound (I-o) can be obtained by reaction of Compound (I-n) [Compound (I) in which $X^2$ is O] obtained by Process 1 to Process 7 with a thionating agent. Examples of the thionating agent are phosphorus pentachloride and Leawsson's reagent. As a reaction solvent, pyridine, dimethylformamide, dioxane, tetrahydrofuran, or the like, preferably pyridine, may be used. The reaction is completed in 10 minutes to 36 hours at 50° to 180° C.

The desired compounds in the processes described above can be isolated and purified by purification methods conventionally used in organic synthetic chemistry, for example, filtration, extraction, washing, drying, concentration, recrystallization, and various kinds of chromatography.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or a base to form a salt.

Compounds (I) arid pharmaceutically acceptable salts thereof may be in the form of adducts with water or various solvents, which can also be used as the therapeutic agent of the present invention.

Examples of Compounds (I) are shown in Table 1, and the structures thereof are shown in Table 2.

TABLE 1

| Compound No. | Name of the Compound |
|---|---|
| 1 | (E)-8-(3,4-dimethoxystyryl)-7-methyl-1,3-dipropylxanthine |
| 2 | (E)-8-(3,4,5-trimethoxystyryl)caffeine |
| 3 | (E)-7-methyl-1,3-dipropyl-8-styrylxanthine |
| 4 | (E)-1,3-diethyl-7-methyl-8-(3,4,5-trimethoxystyryl)xanthine |
| 5 | (E)-7-methyl-1,3-dipropyl-8-(3,4,5-trimethoxystyryl)xanthine |
| 6 | (E)-8-(4-methoxystyryl)-7-methyl-1,3-dipropylxanthine |
| 7 | (E)-1,3-diallyl-7-methyl-8-(3,4,5-trimethoxystyryl)xanthine |
| 8 | (E)-1,3-dibutyl-8-(3,4,5-trimethoxystyryl)xanthine |
| 9 | (E)-1,3-dibutyl-7-methyl-8-(3,4,5-trimethoxystyryl)xanthine |
| 10 | (E)-1,3-dipropyl-8-(3,4,5-trimethoxystyryl)xanthine |
| 11 | (E)-8-(3,4,5-trimethoxystyryl)theophylline |
| 12 | (E)-1,3-diallyl-8-(3,4,5-trimethoxystyryl)xanthine |
| 13 | (E)-8-(4-methoxy-2,3-dimethylstyryl)-1,3-dipropylxanthine |
| 14 | (E)-8-(4-methoxy-2,3-dimethylstyryl)-7-methyl-1,3-dipropylxanthine |
| 15 | (E)-8-(2,4-dimethoxy-3-methylstyryl)-1,3-dipropylxanthine |
| 16 | (E)-8-(2,4-dimethoxy-3-methylstyryl)-7-methyl-1,3-dipropylxanthine |
| 17 | (E)-8-[2-(1,4-benzodioxan-6-yl)vinyl]-1,3-dipropylxanthine |
| 18 | (E)-8-[2-(1,4-benzodioxan-6-yl)vinyl]-7-methyl-1,3-dipropylxanthine |
| 19 | (E)-8-(3,4-methylenedioxystyryl)-1,3-dipropylxanthine |
| 20 | (E)-7-methyl-8-(3,4-methylenedioxystyryl)-1,3-dipropylxanthine |
| 21 | (E)-1,3-dipropyl-8-(2,3,4-trimethoxystyryl)xanthine |
| 22 | (E)-7-methyl-1,3-dipropyl-8-(2,3,4-trimethoxystyryl)xanthine |
| 23 | (E)-1,3-dipropyl-8-(2,4,5-trimethoxystyryl)xanthine |
| 24 | (E)-7-methyl-1,3-dipropyl-8-(2,4,5-trimethoxystyryl)xanthine |
| 25 | (E)-8-(2,4-dimethoxystyryl)-1,3-dipropylxanthine |
| 26 | (E)-8-(2,4-dimethoxystyryl)-7-methyl-1,3-dipropylxanthine |
| 27 | (E)-8-(4-benzyloxy-3,5-dimethoxystyryl)-1,3-dipropylxanthine |

TABLE 1-continued

| Compound No. | Name of the Compound |
|---|---|
| 28 | (E)-8-(4-benzyloxy-3,5-dimethoxystyryl)-7-methyl-1,3-dipropylxanthine |
| 29 | (E)-8-(2,3-dimethoxystyryl)-1,3-dipropylxanthine |
| 30 | (E)-8-(2,3-dimethoxystyryl)-7-methyl-1,3-dipropylxanthine |
| 31 | (E)-8-(3,4-dimethylstyryl)-1,3-dipropylxanthine |
| 32 | (E)-8-(3,4-dimethylstyryl)-7-methyl-1,3-dipropylxanthine |
| 33 | (E)-8-(3,5-dimethoxystyryl)-1,3-dipropylxanthine |
| 34 | (E)-8-(3,5-dimethoxystyryl)-7-methyl-1,3-dipropylxanthine |
| 35 | (E)-8-(3-nitrostyryl)-1,3-dipropylxanthine |
| 36 | (E)-7-methyl-8-(3-nitrostyryl)-1,3-dipropylxanthine |
| 37 | (E)-8-(3-fluorostyryl)-1,3-dipropylxanthine |
| 38 | (E)-8-(3-fluorostyryl)-7-methyl-1,3-dipropylxanthine |
| 39 | (E)-8-(3-chlorostyryl)-1,3-dipropylxanthine |
| 40 | (E)-8-(3-chlorostyryl)-7-methyl-1,3-dipropylxanthine |
| 41 | (E)-8-(2-chlorostyryl)-1,3-dipropylxanthine |
| 42 | (E)-8-(2-chlorostyryl)-7-methyl-1,3-dipropylxanthine |
| 43 | (E)-8-(2-fluorostyryl)-1,3-dipropylxanthine |
| 44 | (E)-8-(2-fluorostyryl)-7-methyl-1,3-dipropylxanthine |
| 45 | (E)-8-(4-methoxy-2,5-dimethylstyryl)-1,3-dipropylxanthine |
| 46 | (E)-8-(4-methoxy-2,5-dimethylstyryl)-7-methyl-1,3-dipropylxanthine |
| 47 | (Z)-8-(3,4-dimethoxystyryl)-7-methyl-1,3-dipropylxanthine |
| 48 | (E)-8-(4-ethoxystyryl)-1,3-dipropylxanthine |
| 49 | (E)-8-(4-ethoxystyryl)-7-methyl-1,3-dipropylxanthine |
| 50 | (E)-8-(4-propoxystyryl)-1,3-dipropylxanthine |
| 51 | (E)-7-methyl-8-(4-propoxystyryl)-1,3-dipropylxanthine |
| 52 | (E)-8-(4-butoxystyryl)-1,3-dipropylxanthine |
| 53 | (E)-8-(4-butoxystyryl)-7-methyl-1,3-dipropylxanthine |
| 54 | (E)-8-(3,4-dihydroxystyryl)-7-methyl-1,3-dipropylxanthine |
| 55 | (E)-8-(3,4-diethoxystyryl)-7-methyl-1,3-dipropylxanthine |
| 56 | (E)-8-(3-bromo-4-methoxystyryl)-1,3-dipropylxanthine |
| 57 | (E)-8-(3-bromo-4-methoxystyryl)-7-methyl-1,3-dipropylxanthine |
| 58 | (E)-8-(2-bromo-4,5-dimethoxystyryl)-1,3-dipropylxanthine |
| 59 | (E)-8-(2-bromo-4,5-dimethoxystyryl)-7-methyl-1,3-dipropylxanthine |
| 60 | (E)-8-(3-bromo-4,5-dimethoxystyryl)-1,3-dipropylxanthine |
| 61 | (E)-8-(3-bromo-4,5-dimethoxystyryl)-7-methyl-1,3-dipropylxanthine |
| 62 | (E)-8-[2-(4-methoxynaphthyl)vinyl]-1,3-dipropylxanthine |
| 63 | (E)-8-[2-(4-methoxynaphthyl)vinyl]-7-methyl-1,3-dipropylxanthine |
| 64 | (E)-8-(3-hydroxy-4-methoxystyryl)-7-methyl-1,3-dipropylxanthine |
| 65 | (Z)-8-(3,4-dimethoxystyryl)-7-methyl-1,3-dipropylxanthine |
| 66 | (E)-8-(3,4-dimethoxystyryl)-7-ethyl-1,3-dipropylxanthine |
| 67 | (E)-8-(3,4-dimethoxystyryl)-7-propargyl-1,3-dipropylxanthine |
| 68 | (E)-8-(3,4-bis(methoxymethoxy)styryl]-7-methyl-1,3-dipropylxanthine |
| 69 | (E)-1,3-diallyl-8-(3,4-dimethoxystyryl)xanthine |
| 70 | (E)-1,3-diallyl-8-(3,4-dimethoxystyryl)-7-methylxanthine |
| 71 | (E)-8-(3,4-dimethoxystyryl)-1,3-dipropyl-2-thioxanthine |
| 72 | (E)-8-(3,4-dimethoxystyryl)-7-methyl-1,3-dipropyl-2-thioxanthine |
| 73 | (E)-8-(3,4-dimethoxystyryl)-1,3-diethylxanthine |
| 74 | (E)-8-(3,4-dimethoxystyryl)-1,3-diethyl-7-methylxanthine |
| 75 | (E)-8-(2,3-dimethoxystyryl)-1,3-diethylxanthine |
| 76 | (E)-8-(2,3-dimethoxystyryl)-1,3-diethyl-7-methylxanthine |
| 77 | (E)-8-(2,4-dimethoxystyryl)-1,3-diethylxanthine |
| 78 | (E)-8-(2,4-dimethoxystyryl)-1,3-diethyl-7-methylxanthine |
| 79 | (E)-1,3-diethyl-8-(2,3,4-trimethoxystyryl)-xanthine |
| 80 | (E)-1,3-diethyl-7-methyl-8-(2,3,4-trimethoxystyryl)xanthine |
| 81 | (E)-1,3-diethyl-8-(4-methoxy-2,3-dimethylstyryl)-xanthine |
| 82 | (E)-1,3-diethyl-8-(4-methoxy-2,3-dimethylstyryl)-7-methylxanthine |
| 83 | (E)-1,3-diethyl-8-(4-methoxy-2,5-dimethylstyryl)-xanthine |
| 84 | (E)-1,3-diethyl-8-(4-methoxy-2,5-dimethylstyryl)-7-methylxanthine |
| 85 | (E)-B-(2,4-dimethoxy-3-methylstyryl)-1,3-diethyl-xanthine |
| 86 | (E)-8-(2,4-dimethoxy-3-methylstyryl)-1,3-diethyl-7-methylxanthine |
| 87 | (E)-1,3-diethyl-8-(3,4-methylenedioxystyryl)-xanthine |
| 88 | (E)-1,3-diethyl-7-methyl-8-(3,4-methylenedioxystyryl)xanthine |
| 89 | (E)-8-[2-(1,4-benzodioxan-6-yl)vinyl]-1,3-diethylxanthine |
| 90 | (E)-8-[2-(1,4-benzodioxan-6-yl)vinyl]-1,3-diethyl-7-methylxanthine |
| 91 | (E)-8-(2,3,4-trimethoxystyryl)theophylline |
| 92 | (E)-8-(2,3,4-trimethoxystyryl)caffeine |
| 93 | (E)-8-(4-methoxy-2,3-dimethylstyryl)theophylline |
| 94 | (E)-8-(4-methoxy-2,3-dimethylstyryl)caffeine |
| 95 | (E)-8-(3,4-methylenedioxystyryl)theophylline |
| 96 | (E)-8-(3,4-methylenedioxystyryl)caffeine |
| 97 | (E)-8-(2,3-dimethoxystyryl)theophylline |
| 98 | (E)-8-(2,3-dimethoxystyryl)caffeine |
| 99 | (E)-8-(2,4-dimethoxystyryl)theophylline |
| 100 | (E)-8-(2,4-dimethoxystyryl)caffeine |
| 101 | (E)-8-(4-methoxy-2,5-dimethylstyryl)theophylline |
| 102 | (E)-8-(4-methoxy-2,5-dimethylstyryl)caffeine |
| 103 | (E)-8-(2,4-dimethoxy-3-methylstyryl)theophylline |
| 104 | (E)-8-(2,4-dimethoxy-3-methylstyryl)caffeine |
| 105 | (E)-8-(2-chloro-3,4-dimethoxystyryl)-1,3-diethylxanthine |
| 106 | (E)-8-(2-chloro-3,4-dimethoxystyryl)-1,3-diethyl-7-methylxanthine |
| 107 | (E)-8-(2-chloro-3,4-dimethoxystyryl)theophylline |
| 108 | (E)-8-(2-chloro-3,4-dimethoxystyryl)caffeine |
| 109 | (E)-8-(2,5-dimethylstyryl)-1,3-diethylxanthine |
| 110 | (E)-8-(2,5-dimethylstyryl)-1,3-diethyl-7-methylxanthine |
| 111 | (E)-8-(3,4-difluorostyryl)-1,3-diethylxanthine |
| 112 | (E)-8-(3,4-difluorostyryl)-1,3-diethyl-7-methylxanthine |
| 113 | (E)-8-(3-bromo-4-methoxystyryl)-1,3-diethylxanthine |
| 114 | (E)-8-(3-bromo-4-methoxystyryl)-1,3-diethyl-7-methylxanthine |
| 115 | (E)-8-(3-bromo-4-methoxystyryl)theophylline |
| 116 | (E)-8-(3-bromo-4-methoxystyryl)caffeine |
| 117 | (E)-8-(2-bromo-4,5-dimethoxystyryl)-1,3-diethylxanthine |
| 118 | (E)-8-(2-bromo-4,5-dimethoxystyryl)-1,3-diethyl-7-methylxanthine |
| 119 | (E)-8-(4,5-dimethoxy-2-nitrostyryl)-1,3-diethylxanthine |
| 120 | (E)-8-(4,5-dimethoxy-2-nitrostyryl)-1,3-diethyl-7-methylxanthine |

TABLE 1-continued

| Compound No. | Name of the Compound |
|---|---|
| 121 | (E)-1,3-diethyl-8-(3-methoxy-2-nitrostyryl)-xanthine |
| 122 | (E)-1,3-diethyl-8-(3-methoxy-2-nitrostyryl)-7-methylxanthine |
| 123 | (E)-8-(4-ethoxystyryl)-1,3-diethylxanthine |
| 124 | (E)-8-(4-ethoxystyryl)-1,3-diethyl-7-methyl-xanthine |
| 125 | (E)-1,3-diethyl-8-(4-propoxystyryl)xanthine |
| 126 | (E)-1,3-diethyl-7-methyl-8-(4-propoxystyryl)-xanthine |
| 127 | (E)-1,3-diethyl-8-(3-fluorostyryl)xanthine |
| 128 | (E)-1,3-diethyl-8-(3-fluorostyryl)-7-methyl-xanthine |
| 129 | (E)-8-(3,5-dimethoxystyryl)-1,3-diethylxanthine |
| 130 | (E)-8-(3,5-dimethoxystyryl)-1,3-diethyl-7-methyl-xanthine |
| 131 | (E)-8-(3-chlorostyryl)-1,3-diethylxanthine |
| 132 | (E)-8-(3-chlorostyryl)-1,3-diethyl-7-methyl-xanthine |
| 133 | (E)-1,3-diethyl-8-(α-methylstyryl)xanthine |
| 134 | (E)-1,3-diethyl-7-methyl-8-(α-methylstyryl)-xanthine |
| 135 | (E)-1,3-diethyl-8-(4-trifluoromethylstyryl)-xanthine |
| 136 | (E)-1,3-diethyl-7-methyl-8-(4-trifluoromethyl-styryl)xanthine |
| 137 | (E)-1,3-diethyl-8-(α-fluorostyryl)xanthine |
| 138 | (E)-1,3-diethyl-8-(α-fluorostyryl)-7-methyl-xanthine |
| 139 | (E)-1,3-diethyl-8-(3-methoxystyryl)xanthine |
| 140 | (E)-1,3-diethyl-8-(3-methoxystyryl)-7-methyl-xanthine |
| 141 | (E)-8-(4-bromostyryl)-1,3-diethylxanthine |
| 142 | (E)-8-(4-bromostyryl)-1,3-diethyl-7-methyl-xanthine |
| 143 | (E)-1,3-diethyl-8-(3-trifluoromethoxystyryl)-xanthine |
| 144 | (E)-1,3-diethyl-7-methyl-8-(3-trifluoromethoxy-styryl)xanthine |
| 145 | (E)-1,3-diethyl-8-(4-methoxymethoxystyryl)-xanthine |
| 146 | (E)-1,3-diethyl-8-(4-methoxymethoxystyryl)-7-methylxanthine |
| 147 | (E)-8-(4-butoxystyryl)-1,3-diethylxanthine |
| 148 | (E)-8-(4-butoxystyryl)-1,3-diethyl-7-methyl-xanthine |
| 149 | (E)-1,3-diethyl-8-(4-fluorostyryl)xanthine |
| 150 | (E)-1,3-diethyl-8-(4-fluorostyryl)-7-methyl-xanthine |
| 151 | (E)-1,3-diethyl-8-(4-methylstyryl)xanthine |
| 152 | (E)-1,3-diethyl-7-methyl-8-(4-methylstyryl)-xanthine |
| 153 | (E)-8-[3,5-bis(trifluoromethyl)styryl]-1,3-diethylxanthine |
| 154 | (E)-8-[3,5-bis(trifluoromethyl)styryl]-1,3-diethyl-7-methylxanthine |
| 155 | (E)-8-(3,5-difluorostyryl)-1,3-diethylxanthine |
| 156 | (E)-8-(3,5-difluorostyryl)-1,3-diethyl-7-methyl-xanthine |
| 157 | (E)-1,3-diethyl-8-(2-methoxystyryl)xanthine |
| 158 | (E)-1,3-diethyl-8-(2-methoxystyryl)-7-methyl-xanthine |
| 159 | (E)-1,3-diethyl-8-(3-nitrostyryl)xanthine |
| 160 | (E)-1,3-diethyl-7-methyl-8-(3-nitrostyryl)xanthine |
| 177 | (E)-8-(3-chloro-4-fluorostyryl)-1,3-diethyl-7-methylxanthine |
| 178 | (E)-1,3-diethyl-8-(3-methoxy-4,5-methylenedioxy-styryl)xanthine |
| 179 | (E)-1,3-diethyl-8-(3-methoxy-4,5-methylenedioxy-styryl)-7-methylxanthine |
| 180 | (E)-1,3-diethyl-8-(3-fluoro-2-methylstyryl)-xanthine |
| 181 | (E)-1,3-diethyl-8-(3-fluoro-2-methylstyryl)-7-methylxanthine |
| 182 | (E)-8-(3,4-dihydroxystyryl)-1,3-diethyl-7-methyl-xanthine |
| 183 | (E)-1,3-diethyl-8-(3-hydroxy-4-methoxystyryl)-7-methylxanthine |
| 184 | (E)-1,3-diethyl-8-(4-hydroxystyryl)-7-methyl-xanthine |
| 185 | (E)-8-(4-benzyloxystyryl)-1,3-diethyl-7-methyl-xanthine |
| 186 | (E)-8-[4-(4-bromobutoxy)styryl]-1,3-diethyl-7-methylxanthine |
| 187 | (E)-8-[4-(4-azidobutoxy)styryl]-1,3-diethyl-7-methylxanthine |
| 188 | (E)-8-[4-(4-aminobutoxy)styryl]-1,3-diethyl-7-methylxanthine |
| 189 | (E)-8-(4-ethoxycarbonylmethoxystyryl)-1,3-diethyl-7-methylxanthine |
| 190 | (E)-8-(4-carboxymethoxystyryl)-1,3-diethyl-7-methylxanthine |
| 191 | (E)-1,3-diethyl-8-(3-phenoxystyryl)xanthine |
| 192 | (E)-1,3-diethyl-7-methyl-8-(3-phenoxystyryl)xanthine |
| 193 | (E)-1,3-diethyl-8-(4-hydroxystyryl)xanthine |
| 194 | (E)-1,3-diethyl-8-(4-hydroxy-2,3-dimethylstyryl)-7-methylxanthine |

TABLE 2-1

| Compd. No. | $-R^1$ | $-R^2$ | $-Z$ | $-R^3$ |
|---|---|---|---|---|
| 1 | $-(CH_2)_2CH_3$ | $-(CH_2)_2CH_3$ | 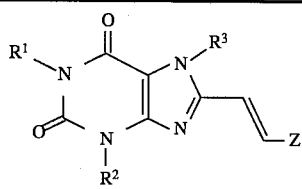 | $-CH_3$ |

TABLE 2-1-continued

[Structure: imidazole-fused pyrimidinedione with R¹ on N, R³ on N, R² on N, and vinyl-Z substituent]

| Compd. No. | -R¹ | -R² | -Z | -R³ |
|---|---|---|---|---|
| 2 | -CH₃ | -CH₃ | 3,4,5-tri(OCH₃)-phenyl | " |
| 3 | -(CH₂)₂CH₃ | -(CH₂)₂CH₃ | phenyl | " |
| 4 | -CH₂CH₃ | -CH₂CH₃ | 3,4,5-tri(OCH₃)-phenyl | " |
| 5 | -(CH₂)₂CH₃ | -(CH₂)₂CH₃ | " | " |
| 6 | " | " | 4-OCH₃-phenyl | " |
| 7 | -CH₂-CH=CH₂ | -CH₂-CH=CH₂ | 3,4,5-tri(OCH₃)-phenyl | " |
| 8 | -(CH₂)₃CH₃ | -(CH₂)₃CH₃ | " | -H |
| 9 | -(CH₂)₃CH₃ | -(CH₂)₃CH₃ | " | -CH₃ |
| 10 | -(CH₂)₂CH₃ | -(CH₂)₂CH₃ | " | -H |
| 11 | -CH₃ | -CH₃ | " | " |
| 12 | -CH₂-CH=CH₂ | -CH₂-CH=CH₂ | " | " |
| 13 | -(CH₂)₂CH₃ | -(CH₂)₂CH₃ | 4-OCH₃-2,3-di(CH₃)-phenyl | " |
| 14 | " | " | " | -CH₃ |
| 15 | " | " | 3-OCH₃-4-... methyl substituted phenyl | -H |
| 16 | " | " | " | -CH₃ |

TABLE 2-1-continued
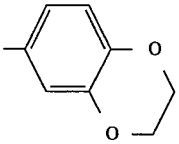
| Compd. No. | −R¹ | −R² | −Z | −R³ |
|---|---|---|---|---|
| 17 | −(CH₂)₂CH₃ | −(CH₂)₂CH₃ | 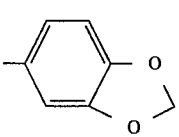 | −H |
| 18 | " | " | " | −CH₃ |
| 19 | " | " | 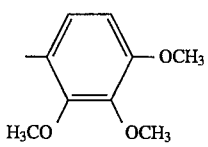 | −H |
| 20 | " | " | " | −CH₃ |
| 21 | " | " | 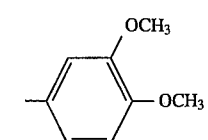 | −H |
| 22 | " | " | " | −CH₃ |
| 23 | " | " | 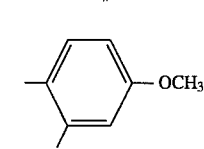 | −H |
| 24 | " | " | " | −CH₃ |
| 25 | " | " | 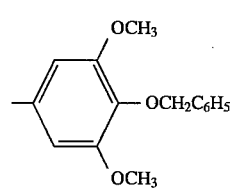 | −H |
| 26 | " | " | " | −CH₃ |
| 27 | " | " | 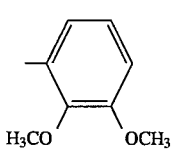 | −H |
| 28 | " | " | " | −CH₃ |
| 29 | " | " |  | −H |
| 30 | " | " | " | −CH₃ |

TABLE 2-1-continued

| Compd. No. | −R¹ | −R² | −Z | −R³ |
|---|---|---|---|---|
| 31 | " | " | 2,5-dimethylphenyl | −H |
| 32 | " | " | " | −CH₃ |
| 33 | −(CH₂)₂CH₃ | −(CH₂)₂CH₃ | 3,5-dimethoxyphenyl | −H |
| 34 | " | " | " | −CH₃ |
| 35 | " | " | 3-nitrophenyl | −H |
| 36 | " | " | " | −CH₃ |
| 37 | " | " | 3-fluorophenyl | −H |
| 38 | " | " | " | −CH₃ |
| 39 | " | " | 3-chlorophenyl | −H |
| 40 | " | " | " | −CH₃ |
| 41 | " | " | 2-chlorophenyl | −H |
| 42 | " | " | " | −CH₃ |
| 43 | " | " | 2-fluorophenyl | −H |
| 44 | " | " | " | −CH₃ |

TABLE 2-1-continued

[Structure: imidazole fused with pyrimidinedione, with R¹-N, R²-N, R³-N substituents and a vinyl-Z group]

| Compd. No. | −R¹ | −R² | −Z | −R³ |
|---|---|---|---|---|
| 45 | " | " | 2,5-dimethyl-4-methoxyphenyl (CH₃, OCH₃, H₃C) | −H |
| 46 | " | " | " | −CH₃ |
| 47* | " | " | R⁴ = vinyl-(3,4-dimethoxyphenyl) (H₃CO, OCH₃) | " |

*An about 6:4 mixture with Compound 1.

| Compd. No. | −R¹ | −R² | −Z | −R³ |
|---|---|---|---|---|
| 48 | −(CH₂)₂CH₃ | −(CH₂)₂CH₃ | 4-OCH₂CH₃-phenyl | −H |
| 49 | " | " | " | −CH₃ |
| 50 | " | " | 4-O(CH₂)₂CH₃-phenyl | −H |
| 51 | " | " | " | −CH₃ |
| 52 | " | " | 4-O(CH₂)₃CH₃-phenyl | −H |
| 53 | " | " | " | −CH₃ |
| 54 | " | " | 3,4-dihydroxyphenyl (OH, OH) | " |
| 55 | " | " | 3,4-bis(OCH₂CH₃)phenyl | " |
| 56 | " | " | 3-Br-4-OCH₃-phenyl | −H |

TABLE 2-1-continued
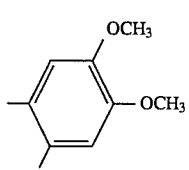
| Compd. No. | −R¹ | −R² | −Z | −R³ |
|---|---|---|---|---|
| 57 | " | " | " | −CH₃ |
| 58 | " | " | 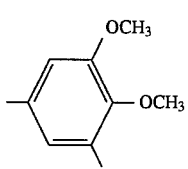 | −H |
| 59 | " | " | " | −CH₃ |
| 60 | " | " | 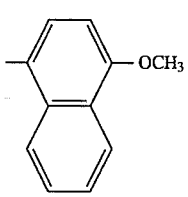 | −H |
| 61 | " | " | " | −CH₃ |
| 62 | " | " | 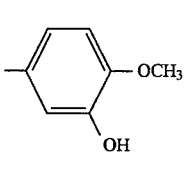 | −H |
| 63 | " | " | " | −CH₃ |
| 64 | " | " | 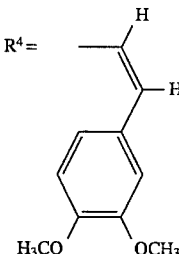 | " |
| 65 | " | " | R⁴ = 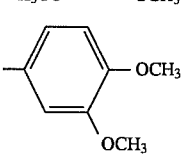 | " |
| 66 | −(CH₂)₂CH₃ | −(CH₂)₂CH₃ | (3,4-dimethoxyphenyl) | −C₂H₅ |
| 67 | " | " | " | −CH₂C≡CH |

TABLE 2-1-continued

[Structure: xanthine-imidazole fused ring with R¹ on N, R² on N, R³ on N, and 2-position substituted with CH=CH-Z]

| Compd. No. | -R¹ | -R² | -Z | -R³ |
|---|---|---|---|---|
| 68 | " | " | 4-(OCH₂OCH₃), 3-(OCH₂OCH₃)-phenyl | -CH₃ |
| 69 | -CH₂-CH=CH₂ | -CH₂-CH=CH₂ | 4-OCH₃, 3-OCH₃-phenyl | -H |
| 70 | " | " | " | -CH₃ |
| 71* | -(CH₂)₂CH₃ | -(CH₂)₂CH₃ | " | -H |
| 72* | " | " | " | -CH₃ |
| 73 | -CH₂CH₃ | -CH₂CH₃ | " | -H |
| 74 | " | " | " | -CH₃ |
| 75 | " | " | 2,3-di(OCH₃)-phenyl | -H |
| 76 | " | " | " | -CH₃ |
| 77 | " | " | 2,4-di(OCH₃)-phenyl (with H₃CO at 3) | -H |
| 78 | " | " | " | -CH₃ |
| 79 | " | " | 2,3,4-tri(OCH₃)-phenyl | -H |
| 80 | " | " | " | -CH₃ |
| 81 | " | " | 4-OCH₃, 2,3-di(CH₃)-phenyl | -H |
| 82 | " | " | " | -CH₃ |
| 83 | " | " | 2,5-di(CH₃), 4-OCH₃-phenyl | -H |
| 84 | " | " | " | -CH₃ |

TABLE 2-1-continued

Structure: R¹-N, R³-N in a fused bicyclic system with =O groups, connected to vinyl-Z group

| Compd. No. | —R¹ | —R² | —Z | —R³ |
|---|---|---|---|---|
| 85 | " | " | 4-OCH₃, 2-CH₃, 3-OCH₃ phenyl (2,3-dimethoxy-... with CH₃) | —H |
| 86 *2-Thio form | " | " | " | —CH₃ |
| 87 | —CH₂CH₃ | —CH₂CH₃ | 3,4-methylenedioxyphenyl | —H |
| 88 | " | " | " | —CH₃ |
| 89 | " | " | 3,4-ethylenedioxyphenyl | —H |
| 90 | " | " | " | —CH₃ |
| 91 | —CH₃ | —CH₃ | 3,4,5-trimethoxyphenyl | —H |
| 92 | " | " | " | —CH₃ |
| 93 | " | " | 3,5-dimethyl-4-methoxyphenyl | —H |
| 94 | " | " | " | —CH₃ |
| 95 | " | " | 3,4-methylenedioxyphenyl | —H |
| 96 | " | " | " | —CH₃ |
| 97 | " | " | 2,3-dimethoxyphenyl | —H |
| 98 | " | " | " | —CH₃ |

TABLE 2-1-continued

| Compd. No. | −R¹ | −R² | −Z | −R³ |
|---|---|---|---|---|
| 99 | " | " | 2,5-dimethoxyphenyl (−C₆H₃(OCH₃)₂, with OCH₃ and H₃CO) | −H |
| 100 | " | " | " | −CH₃ |
| 101 | " | " | 2,5-dimethyl-4-methoxyphenyl (CH₃, OCH₃, H₃C) | −H |
| 102 | " | " | " | −CH₃ |
| 103 | " | " | 2-methyl-3-methoxy-... (OCH₃, H₃CO, CH₃) | −H |
| 104 | " | " | " | −CH₃ |
| 105 | −CH₂CH₃ | −CH₂CH₃ | 3-chloro-2,4-dimethoxyphenyl (OCH₃, Cl, OCH₃) | −H |
| 106 | " | " | " | −CH₃ |
| 107 | −CH₃ | −CH₃ | " | −H |
| 108 | " | " | " | −CH₃ |
| 109 | −CH₂CH₃ | −CH₂CH₃ | 2,5-dimethylphenyl (CH₃, H₃C) | −H |
| 110 | " | " | " | −CH₃ |
| 111 | " | " | 3,4-difluorophenyl (F, F) | −H |
| 112 | " | " | " | −CH₃ |
| 113 | " | " | 3-bromo-4-methoxyphenyl (OCH₃, Br) | −H |
| 114 | " | " | " | −CH₃ |

TABLE 2-1-continued

Structure: Imidazo-fused pyrimidinedione with R¹-N, R²-N, R³-N substituents and -CH=CH-Z vinyl group

| Compd. No. | -R¹ | -R² | -Z | -R³ |
|---|---|---|---|---|
| 115 | -CH₃ | -CH₃ | " | -H |
| 116 | " | " | " | -CH₃ |
| 117 | -CH₂CH₃ | -CH₂CH₃ | 5-bromo-2,4-dimethoxyphenyl (OCH₃, OCH₃, Br) | -H |
| 118 | " | " | " | -CH₃ |
| 119 | " | " | 2,4-dimethoxy-5-nitrophenyl (OCH₃, OCH₃, O₂N) | -H |
| 120 | " | " | " | -CH₃ |
| 121 | " | " | 2-methoxy-3-nitrophenyl (O₂N, OCH₃) | -H |
| 122 | " | " | " | -CH₃ |
| 123 | -CH₂CH₃ | -CH₂CH₃ | 4-ethoxyphenyl (-OCH₂CH₃) | -H |
| 124 | " | " | " | -CH₃ |
| 125 | " | " | 4-propoxyphenyl (-O(CH₂)₂CH₃) | -H |
| 126 | " | " | " | -CH₃ |
| 127 | " | " | 3-fluorophenyl (F) | -H |
| 128 | " | " | " | -CH₃ |
| 129 | " | " | 3,5-dimethoxyphenyl (OCH₃, OCH₃) | -H |
| 130 | " | " | " | -CH₃ |

TABLE 2-1-continued

| Compd. No. | −R¹ | −R² | −Z | −R³ |
|---|---|---|---|---|
| 131 | " | " | 3-Cl-C₆H₄ | −H |
| 132 | " | " | " | −CH₃ |
| 133 | " | " | R⁴=CH₃, (E)-PhCH= | −H |
| 134 | " | " | " | −CH₃ |
| 135 | " | " | 4-CF₃-C₆H₄ | −H |
| 136 | " | " | " | −CH₃ |
| 137 | " | " | R⁴=F, PhCH= | −H |
| 138 | " | " | " | −CH₃ |
| 139 | " | " | 3-OCH₃-C₆H₄ | −H |
| 140 | " | " | " | −CH₃ |
| 141 | −CH₂CH₃ | −CH₂CH₃ | 4-Br-C₆H₄ | −H |
| 142 | " | " | " | −CH₃ |
| 143 | " | " | 3-OCF₃-C₆H₄ | −H |
| 144 | " | " | " | −CH₃ |
| 145 | " | " | 4-OCH₂OCH₃-C₆H₄ | −H |
| 146 | " | " | " | −CH₃ |

TABLE 2-1-continued

| Compd. No. | -R¹ | -R² | -Z | -R³ |
|---|---|---|---|---|
| 147 | " | " | -C₆H₄-O(CH₂)₃CH₃ (para) | -H |
| 148 | " | " | " | -CH₃ |
| 149 | " | " | -C₆H₄-F (para) | -H |
| 150 | " | " | " | -CH₃ |
| 151 | " | " | -C₆H₄-CH₃ (para) | -H |
| 152 | " | " | " | -CH₃ |
| 153 | " | " | -C₆H₃(CF₃)₂ (3,5) | -H |
| 154 | " | " | " | -CH₃ |
| 155 | " | " | -C₆H₃F₂ (3,5) | -H |
| 156 | " | " | " | -CH₃ |
| 157 | " | " | -C₆H₄-OCH₃ (ortho) | -H |
| 158 | " | " | " | -CH₃ |
| 159 | " | " | -C₆H₄-NO₂ (meta) | -H |
| 160 | " | " | " | -CH₃ |
| 161 | -CH₂CH₃ | -CH₂CH₃ | -C₆H₄-Br (meta) | -H |

TABLE 2-1-continued

| Compd. No. | −R¹ | −R² | −Z | −R³ |
|---|---|---|---|---|
| 162 | " | " | " | −CH₃ |
| 163 | " | " | 3-CF₃-phenyl | −H |
| 164 | " | " | " | −CH₃ |
| 165 | " | " | 5-Br-2,3-methylenedioxyphenyl | −H |
| 166 | " | " | " | −CH₃ |
| 167 | " | " | 2-F-phenyl | −H |
| 168 | " | " | " | −CH₃ |
| 169 | " | " | 4-N(CH₃)₂-phenyl | −H |
| 170 | " | " | 4-biphenyl | " |
| 171 | " | " | " | −CH₃ |
| 172 | " | " | 3-F-4-OCH₃-phenyl | −H |
| 173 | " | " | " | −CH₃ |
| 174 | " | " | 3-CH₃-4-OCH₃-phenyl | −H |
| 175 | " | " | " | −CH₃ |
| 176 | " | " | 3-Cl-4-F-phenyl | −H |

TABLE 2-1-continued
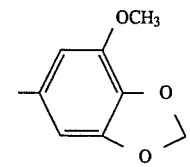
| Compd. No. | —R¹ | —R² | —Z | —R³ |
|---|---|---|---|---|
| 177 | " | " | " | —CH₃ |
| 178 | —CH₂CH₃ | —CH₂CH₃ | 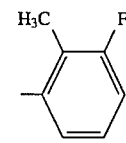 | —H |
| 179 | " | " | " | —CH₃ |
| 180 | " | " | 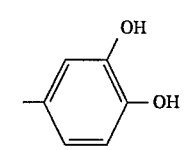 | —H |
| 181 | " | " | " | —CH₃ |
| 182 | " | " | 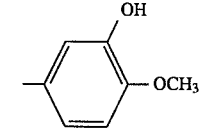 | " |
| 183 | " | " | 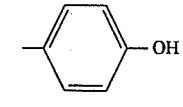 | " |
| 184 | " | " | 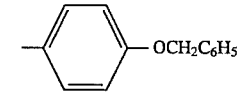 | " |
| 185 | " | " | 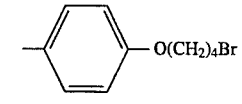 | " |
| 186 | " | " | 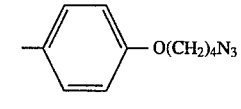 | " |
| 187 | " | " | 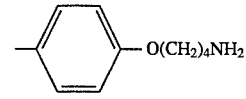 | " |
| 188 | " | " | 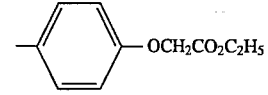 | " |
| 189 | " | " | —⌬—OCH₂CO₂C₂H₅ | " |

TABLE 2-1-continued

| Compd. No. | $-R^1$ | $-R^2$ | $-Z$ | $-R^3$ |
|---|---|---|---|---|
| 190 | " | " | -C6H4-OCH2CO2H | " |
| 191 | " | " | -C6H4-O-C6H5 | -H |
| 192 | " | " | " | -CH3 |
| 193 | " | " | -C6H4-OH | -H |
| 194 | " | " | -C6H2(CH3)2-OH | -CH3 |

The pharmacological activities of Compounds (I) are shown below by test examples.

Test Example 1

Effect on Clonidine-Induced Aggressive Behavior

The effect of a test compound on the aggressive behavior induced by intraperitoneal administration of clonidine was investigated. [Eur. J. Pharmacol., 29, 374 (1968)].

The experiment was performed by using several groups of male ddY mice (weighing 20 to 25 g, Japan SLC), each group consisting of two mice. The test compound was suspended in injectable distilled water (Otsuka Pharmaceutical Co., Ltd.) containing Tween 80 [polyoxyethylene (20) sorbitan monooleate]. Clonidine hydrochloride (Sigma Co.) was dissolved in physiological saline solution (Otsuka Pharmaceutical Co., Ltd.). The test compound suspension and the control suspension were orally administered to separate groups of the mice (0.1 ml per 10 g of body weight). Sixty minutes after the oral administration of the test compound, clonidine hydrochloride (20 mg/kg) was intraperitoneally injected. The number of biting attacks during 30 minutes after clonidine treatment was counted. The effect of the compound was evaluated by comparing the average number of biting attacks of the test compound-administered groups with that of control groups (Statistical comparison: Student's t-test).

The results are shown in Table 3.

TABLE 3

| | | Number of the Biting Attacks (mean ± S.E.M.) | | Number of the Attacks of Test Compound- |
|---|---|---|---|---|
| Compd. | Dose (mg/kg, po) | Control Group (number of animals) | Test Compound-Treated Group (number of animals) | Treated Group/ Number of the Attacks of Control Group |
| 1 | 2.5 | 5.7 ± 1.52 (20) | 27.5 ± 7.3* (15) | 4.8 |
| 2 | 1.25 | 6.2 ± 1.87 (20) | 29.0 ± 7.9* (15) | 4.7 |
| 3 | 10 | 7.7 ± 2.39 (15) | 26.1 ± 5.42** 15) | 3.4 |
| 4 | 10 | 3.2 ± 1.24 (15) | 51.3 ± 9.37*** 15) | 16.0 |
| 4 | 2.5 | 6.8 ± 3.17 | 36.9 ± 7.81** | 5.4 |

TABLE 3-continued

| Compd. | Dose (mg/kg, po) | Number of the Biting Attacks (mean ± S.E.M.) | | Number of the Attacks of Test Compound-Treated Group/ Number of the Attacks of Control Group |
|---|---|---|---|---|
| | | Control Group (number of animals) | Test Compound-Treated Group (number of animals) | |
| 4 | 0.63 | 2.6 ± 1.28 (15) | 25.3 ± 4.51*** (15) | 9.7 |
| 5 | 5 | 7.3 ± 2.56 (10) | 25.4 ± 7.71* (15) | 3.5 |
| 6 | 10 | 7.7 ± 2.39 (20) | 83.7 ± 10.95** (15) | 10.9 |
| 7 | 2.5 | 6.3 ± 3.06 (15) | 40.1 ± 8.36** (15) | 6.4 |
| 14 | 2.5 | 5.6 ± 3.06 (15) | 40.7 ± 8.50* (15) | 7.3 |
| 18 | 10 | 4.1 ± 1.80 (15) | 26.2 ± 7.32** (15) | 6.4 |
| 18 | 2.5 | 2.2 ± 1.25 (15) | 8.6 ± 3.74* (15) | 3.9 |
| 22 | 10 | 4.9 ± 2.41 (15) | 33.1 ± 5.18*** (15) | 6.8 |
| 49 | 10 | 2.6 ± 1.36 (15) | 81.5 ± 13.97** (15) | 31.3 |
| 70 | 10 | 7.6 ± 3.33 (10) | 60.3 ± 11.71** (10) | 7.9 |
| 74 | 10 | 4.3 ± 0.97 (15) | 73.3 ± 8.75*** (15) | 17.0 |
| 74 | 2.5 | 6.1 ± 1.71 (15) | 51.3 ± 8.70*** (15) | 8.4 |
| 74 | 0.63 | 6.1 ± 1.71 (15) | 23.2 ± 5.19** (15) | 3.8 |
| 78 | 10 | 5.3 ± 2.97 (15) | 32.1 ± 7.31* (15) | 6.1 |
| 80 | 10 | 4.9 ± 1.51 (15) | 67.5 ± 9.35*** (15) | 13.8 |
| 80 | 2.5 | 4.9 ± 1.51 (15) | 59.3 ± 12.37*** (15) | 12.1 |
| 80 | 0.63 | 6.5 ± 2.46 (15) | 30.3 ± 7.00** (15) | 4.7 |
| 82 | 10 | 7.7 ± 2.49 (15) | 61.8 ± 11.89*** (15) | 8.0 |
| 82 | 2.5 | 6.5 ± 2.46 (15) | 59.0 ± 13.31*** (15) | 9.1 |
| 114 | 10 | 2.1 ± 1.46 (15) | 37.8 ± 8.66** (15) | 18.0 |
| 124 | 10 | 3.7 ± 2.41 (10) | 50.5 ± 17.7* (10) | 13.6 |
| 124 | 2.5 | 2.5 ± 1.64 (15) | 85.8 ± 12.41*** (15) | 34.3 |
| 126 | 10 | 7.8 ± 2.6 (10) | 80.0 ± 13.93*** (10) | 10.3 |
| 130 | 10 | 10.8 ± 7.51 (10) | 52.2 ± 11.79** (10) | 4.8 |
| 148 | 10 | 2.9 ± 1.65 (10) | 46.3 ± 9.40** (10) | 16.0 |
| 150 | 10 | 2.9 ± 1.65 (10) | 42.1 ± 10.18** (10) | 14.5 |
| 152 | 10 | 12.4 ± 4.68 (5) | 82.6 ± 23.07* (5) | 6.7 |
| 162 | 10 | 2.1 ± 1.13 (15) | 17.9 ± 6.67* (15) | 8.5 |
| 168 | 10 | 7.6 ± 3.33 (10) | 53.9 ± 8.59*** (10) | 7.1 |
| 173 | 10 | 7.6 ± 3.33 (10) | 46.8 ± 14.89* (10) | 6.2 |
| 175 | 10 | 6.2 ± 3.02 (10) | 49.1 ± 15.59* (10) | 7.9 |
| 179 | 10 | 6.4 ± 2.98 (10) | 67.7 ± 16.08** (10) | 10.6 |
| 181 | 10 | 6.2 ± 3.02 (10) | 49.5 ± 9.09*** (10) | 8.0 |
| 184 | 10 | 7.6 ± 3.30 (10) | 77.1 ± 11.47*** (10) | 10.1 |
| 185 | 10 | 7.6 ± 3.30 (10) | 46.9 ± 14.00* (10) | 6.2 |
| theo- | 10 | 3.6 ± 1.39 | 18.6 ± 3.58** | 5.2 |

TABLE 3-continued

| | | Number of the Biting Attacks (mean ± S.E.M.) | | Number of the Attacks of Test Compound- |
|---|---|---|---|---|
| Compd. | Dose (mg/kg, po) | Control Group (number of animals) | Test Compound-Treated Group (number of animals) | Treated Group/ Number of the Attacks of Control Group |
| phylline | | (15) | (15) | |

*p<0.05;
**p<0.01;
***p<0.001

As shown in Table 3, single administration of the compound according to the present invention enhanced the aggressive behavior induced by intraperitoneal administration of clonidine.

Test Example 2

Acute Toxicity Test

Test compounds were orally administered to groups of ddY-strain male mice weighing 20±1 g, each group consisting of three mice. Seven days after the administration, minimum lethal dose (MLD) of each compound was determined by observing the mortality. The results are shown in Table 4.

TABLE 4

| Compd. No. | MLD (mg/kg) | Compd. No. | MLD (mg/kg) |
|---|---|---|---|
| 1 | >300 | 33 | >100 |
| 2 | >300 | 34 | >300 |
| 3 | >300 | 35 | >100 |
| 4 | >300 | 36 | >100 |
| 5 | >300 | 37 | >100 |
| 6 | >300 | 38 | >300 |
| 7 | >300 | 39 | >100 |
| 8 | >100 | 40 | >300 |
| 9 | >300 | 41 | >100 |
| 10 | >300 | 42 | >100 |
| 11 | >300 | 43 | >100 |
| 12 | >300 | 44 | >100 |
| 13 | >300 | 45 | >300 |
| 14 | >300 | 46 | >300 |
| 15 | >100 | 47 | >300 |
| 16 | >300 | 48 | >100 |
| 17 | >300 | 49 | >300 |
| 18 | >300 | 50 | >100 |
| 19 | >300 | 51 | >300 |
| 20 | >300 | 52 | >100 |
| 21 | >300 | 53 | >300 |
| 22 | >300 | 54 | >100 |
| 23 | >300 | 55 | >100 |
| 24 | >300 | 56 | >100 |
| 25 | >100 | 57 | >100 |
| 26 | >300 | 58 | >300 |
| 27 | >100 | 59 | >300 |
| 28 | >100 | 60 | >300 |
| 29 | >100 | 61 | >100 |
| 30 | >300 | 62 | >100 |
| 31 | >100 | 63 | >300 |
| 32 | >300 | 64 | >100 |
| 65 | >300 | 97 | >100 |
| 66 | >300 | 98 | >300 |
| 67 | >300 | 99 | >100 |
| 68 | >100 | 100 | >300 |
| 69 | >100 | 101 | >100 |
| 70 | >100 | 102 | >100 |
| 71 | >100 | 103 | >100 |
| 72 | >300 | 104 | >100 |
| 73 | >300 | 105 | >100 |
| 74 | >300 | 106 | >300 |
| 75 | >300 | 107 | >100 |
| 76 | >300 | 108 | >300 |
| 77 | >100 | 109 | >300 |
| 78 | >300 | 110 | >300 |
| 79 | >300 | 111 | >300 |
| 80 | >300 | 112 | >300 |
| 81 | >300 | 113 | >100 |
| 82 | >300 | 114 | >100 |
| 83 | >300 | 115 | >100 |
| 84 | >300 | 116 | >300 |
| 85 | >300 | 117 | >100 |
| 86 | >300 | 118 | >100 |
| 87 | >300 | 119 | >100 |
| 88 | >300 | 120 | >300 |
| 89 | >100 | 121 | >300 |
| 90 | >300 | 122 | >100 |
| 91 | >300 | 123 | >100 |
| 92 | >300 | 124 | >300 |
| 93 | >100 | 125 | >100 |
| 94 | >100 | 126 | >300 |
| 95 | >300 | 127 | >100 |
| 96 | >300 | 128 | >300 |
| 129 | >100 | 162 | >100 |
| 130 | >300 | 163 | >100 |
| 131 | >100 | 164 | >100 |
| 132 | >300 | 165 | >100 |
| 133 | >100 | 166 | >100 |
| 134 | >300 | 167 | >100 |
| 135 | >100 | 168 | >100 |
| 136 | >300 | 169 | >100 |
| 137 | >100 | 170 | >100 |
| 138 | >100 | 171 | >100 |
| 139 | >100 | 172 | >100 |
| 140 | >300 | 173 | >100 |
| 141 | >100 | 174 | >100 |
| 142 | >100 | 175 | >100 |
| 143 | >100 | 176 | >100 |
| 144 | >100 | 177 | >100 |
| 145 | >100 | 178 | >100 |
| 146 | >100 | 179 | >100 |
| 147 | >100 | 180 | >100 |
| 148 | >100 | 181 | >100 |
| 149 | >100 | 182 | >100 |
| 150 | >100 | 183 | >100 |
| 151 | >100 | 184 | >100 |
| 152 | >100 | 185 | >100 |
| 153 | >100 | 186 | >100 |
| 154 | >100 | 187 | >100 |
| 155 | >100 | 188 | >100 |
| 156 | >100 | 189 | >100 |
| 157 | >100 | 190 | >100 |
| 158 | >100 | 191 | >100 |
| 159 | >100 | 192 | >100 |
| 160 | >100 | 193 | >100 |
| 161 | >100 | 194 | >100 |

As shown in Table 4, the MLD value of all the compounds are greater than 100 mg/kg or 300 mg/kg, indicating that the toxicity of the compounds is weak. Therefore, these compounds can be safely used in a wide range of doses.

As described above, Compounds (I) and pharmaceutically acceptable; salts thereof enhance clonidine-induced aggressive behavior. Thus, they are effective as antidepressants.

Compounds (I) and pharmaceutically acceptable salts thereof can be administered as they are, or in the form of various pharmaceutical compositions. The pharmaceutical compositions; in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactoses, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are most useful oral unit dose forms because of the readiness of administration. For preparing tablets and capsules, solid pharmaceutical carriers are used.

Injectable preparations can be prepared using a carrier such as distilled water, a salt solution, a glucose solution, or a mixture of a salt solution and a glucose solution. The preparations can be prepared in the form of solution, suspension, or dispersion according to a conventional method by using a suitable solubilizing agent or suspending agent.

Compounds (I) and pharmaceutically acceptable salts thereof can be administered orally in the said dosage forms or parenterally as injections. The effective dose and the administration schedule vary depending upon the mode of administration, the age, body weight and conditions of a patient, etc. However, generally, Compound (I) or a pharmaceutically acceptable salt thereof is administered in a daily dose of 0.01 to 25 mg/kg in 3 to 4 parts.

Certain embodiments of the invention are illustrated in the following Examples and Reference Examples.

BEST MODE FOR CARRYING OUT THE INVENTION

Example 1

Tablets

Tablets having the following composition were prepared in a conventional manner.

Compound 1 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined, thus obtaining granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter. The composition of each tablet thus prepared is shown in Table 5.

TABLE 5

| Composition of One Tablet | |
|---|---|
| Compound 1 | 20 mg |
| Lactose | 143.4 mg |
| Potato Starch | 30 mg |
| Hydroxypropylcellulose | 6 mg |
| Magnesium Stearate | 0.6 mg |
| | 200 mg |

Example 2

Fine Granules

Fine granules having the following composition were prepared in a conventional manner.

Compound 74 (20 g) was mixed with 655 g of lactose and 285 g of corn starch, followed by addition of 400 g of a 10% aqueous solution of hydroxypropylcellulose. The resultant mixture was kneaded, granulated, add then dried by a conventional method, thus obtaining fine granules containing 20 g of the active ingredient in 1,000 g. The composition of one pack of the fine granules is shown in Table 6.

TABLE 6

| Composition of One Pack of Fine Granules | |
|---|---|
| Compound 74 | 20 mg |
| Lactose | 655 mg |
| Corn Starch | 285 mg |
| Hydroxypropylcellulose | 40 mg |
| | 1,000 mg |

Example 3

Capsules

Capsules having the following composition were prepared in a conventional manner.

Compound 80 (200 g) was mixed with 995 g of Avicel and 5 g of magnesium stearate. The mixture was put in hard capsules No. 4 each having a capacity of 120 mg by using a capsule filler (Model LZ-64, Zanashi), thus obtaining capsules each containing 20 mg of the active ingredient. The composition of one capsule thus prepared is shown in Table 7.

TABLE 7

| Composition of One Capsule | |
|---|---|
| Compound 80 | 20 mg |
| Avicel | 99.5 mg |
| Magnesium Stearate | 0.5 mg |
| | 120 mg |

Example 4

Injections

Injections having the following composition were prepared in a conventional manner.

Compound 82 (1 g) was dissolved in 100 g of purified soybean oil, followed by addition of 12 g of purified egg yolk lecithin and 25 g of glycerine for injection. The resultant mixture was made up to 1,000 ml with distilled water for injection, thoroughly mixed, and emulsified by a conventional method. The resultant dispersion was subjected to aseptic filtration by using 0.2 μm disposable membrane filters, and then aseptically put into glass vials in 2 ml portions, thus obtaining injections containing 2 mg of the active ingredient per vial. The composition of one injection vial is shown in Table 8.

TABLE 8

Composition of One Injection Vial

| | |
|---|---|
| Compound 82 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

Reference Example 1

(E)-8-(3,4-Dimethoxystyryl)-7-methyl-1,3-dipropylxanthine (Compound 1)

3, 4-Dimethoxycinnamic acid (2.03 g, 9.74 mmol) and 3-(3-diethylaminopropyl)-1-ethylcarbodiimide hydrochloride (2.54 g, 13.3 mmol) were added to a mixture of water (60 ml) and dioxane (30 ml) containing 5,6-diamino-1,3-dipropyluracil (U.S. Pat. No. 2,602;795) (2.00 g, 8.85 mmol). The resultant solution was stirred at room temperature for 2 hours at pH 5.5. After neutralization, the reaction solution was extracted three times with 50 ml of chloroform. The combined extract was washed with a saturated aqueous solution of sodium chloride and dried over anhydrous sodium sulfate, followed by evaporation under reduced pressure. The residue was purified by silica gel column chromatography (eluent: 2% methanol/chloroform) to give 3.47 g (yield 94%) of (E)-6-amino-5-(3,4-dimethoxycinnamoyl) amino-1,3-dipropyluracil (Compound A) as an amorphous substance.

NMR (CDCl$_3$; 90 MHz) δ (ppm): 7.84 (1H, brs), 7.50 (1H, d, J=15.9 Hz), 7.10-6.65 (3H, m), 6.53 (1H, d, J=15.9 Hz), 5.75 (2H, brs), 4.00-3.50 (4H, m), 3.85 (6H, brs), 2.00-1.40 (4H, m), 1.10-0.80 (6H, m)

To 3.38 g (8.13 mmol) of Compound A were added 40 ml of dioxane and 80 ml of an aqueous 1N sodium hydroxide solution, followed by heating under reflux for 10 minutes. After cooling, the solution was neutralized, and deposited crystals were collected by filtration. Then, the collected crystals were recrystallized from dimethylsulfoxide/water to give 2.49 g (yield 77%) of (E)-8-(3,4-dimethoxystyryl)-1,3-dipropylxanthine (Compound B) as white crystals.

Melting Point: 260.0°–263.8° C. Elemental Analysis: C$_{21}$H$_{26}$N$_4$O$_4$ Calcd. (%): C, 63.30; H, 6.57; N, 14.06 Found (%): C, 63.29; H, 6.79; N, 14.21 IR (KBr) V$_{max}$ (cm$^{-1}$): 1701, 1640 NMR (DMSO-d$_6$; 270 MHz) δ (ppm): 13.39 (1H, brs), 7.59 (1H, d, J=16.7 Hz), 7.26 (1H, d, J=1.8 Hz), 7.13 (1H, dd, J=1.8, 8.6 Hz), 6.98 (1H, d, J=8:6 Hz), 6.95 (1H, d, J=16.7 Hz), 3.99 (2H, t), 4.00-3.85 (2H, t), 3.83 (3H, s), 3.80 (3H, s), 1.80-1.55 (4H, m), 1.00-0.85 (6H, m)

Compound B (1.20 g, 3.02 mmol) was dissolved in 20 ml of dimethylformamide. To the solution were added 1.04 g (7.55 mmol) of potassium carbonate and subsequently 0.38 ml (6.04 mmol) of methyl iodide, and the resultant mixture was stirred at 50° C. for 30 minutes. After cooling, insoluble matters were filtered off, and 400 ml of water was added to the filtrate. The mixture was extracted three times with 100 ml of chloroform. The extract was washed twice with water and once with a saturated aqueous solution of sodium chloride, and dried over anhydrous sodium sulfate, followed by evaporation under reduced pressure. The residue was purified by silica gel column chromatography (eluent: 1% methanol/chloroform), followed by recrystallization from propanol/water to give 1.22. g (yield 98%) of Compound 1 as white needles.

Melting Point: 164.1°–166.3° C. Elemental Analysis: C$_{22}$H$_{28}$N$_4$O$_4$ Calcd. (%): C, 64.06; H, 6.84; N, 13.58 Found (%): C, 64.06; H, 6.82; N, 13.80 IR (KBr) V$_{max}$ (cm$^{-1}$): 1692, 1657 NMR (DMSO-d$_6$; 270 MHz) δ (ppm): 7.60 (1H, d, J=15.8 Hz), 7.40 (1H, d, J=2.0 Hz), 7.28 (1H, dd, J=2.0, 8.4 Hz), 7.18 (1H, d, J=15.8 Hz), 6.99 (1H, d, J=8.4 Hz), 4.02 (3H, s), 3.99 (2H, t), 3.90-3.80 (2H, m), 3.85 (3H, s), 3.80 (3H, s), 1.80-1.55 (4H, m), 1.00-0.85 (6H, m)

Reference Example 2

(E)-7-Methyl-1,3-dipropyl-8-styrylxanthine (Compound 3)

5,6-Diamino-1,3-dipropyluracil (U.S. Pat. No. 2,602,795) (6.0 g, 26.5 mmol) was slowly added to a mixture of methanol (360 ml) and acetic acid (15 ml) containing cinnamaldehyde (3.34 ml, 26.5 mmol) under ice cooling. The resultant mixture was stirred at room temperature for 30 minutes, followed by evaporation under reduced pressure to give 6.30 g (yield 70%) of (E)-6-amino-5-(3-phenyl-3-propenylidene) -1,3-dipropyluracil (Compound C) as an amorphous substance.

Melting Point: 159.5°–161.0° C. IR (KBr) V$_{max}$ (cm$^{-1}$): 1687, 1593 NMR (CDCl$_3$; 90 MHz) δ (ppm): 9.75-9.60 (1H, m), 7.60-7.25 (5H, m), 7.00-6.80 (2H, m), 5.70 (2H, brs), 4.00-3.70 (4H, m), 2.00-1.40 (4H, m), 1.10-0.75 (6H, m) MS m/e (relative intensity): 340 (100, M$^+$), 130 (86)

To 6.30 g (18.5 mmol) of Compound C was added 240 ml of ethanol, and the mixture was heated under reflux for 2 hours in the presence of 4.32 g (26.5 mmol) of ferric chloride. After cooling, deposited crystals were collected by filtration to give 3.61 g (yield 61%) of (E)-1,3-dipropyl-8-styrylxanthine (Compound D) as white crystals.

Melting Point: 259.3°–261.0° C. (recrystallized from ethanol) Elemental Analysis: C$_{19}$H$_{22}$N$_4$O$_2$ Calcd. (%): C, 67.43; H, 6.55; N, 16.56 Found (%): C, 67.40; H, 6.61; N, 16.71 IR (KBr) V$_{max}$ (cm$^{-1}$): 1700, 1650, 1505 NMR (DMSO-d$_6$) δ (ppm): 13.59 (1H, brs), 7.70-7.55 (3H, m), 7.50-7.30 (3H, m), 7.06 (1H, d, J=16.5 Hz), 3.99 (2H, t), 3.86 (2H, t), 2.80-2.50 (4H, m), 0.95-0.80 (6H, m)

Subsequently, the same procedure as in Reference Example 1 was repeated using Compound D in place of Compound B to give 1.75 g (yield 84%) of Compound 3 as white needles.

Melting Point: 162.8°–163.2° C. Elemental Analysis: C$_{20}$H$_{24}$N$_4$O$_2$ Calcd. (%): C, 68.16; H, 6.86; N, 15.90 Found (%): C, 67.94; H, 6.96; N, 16.15 IR (KBr) V$_{max}$ (cm$^{-1}$): 1690, 1654, 1542, 1450, 1437 NMR (CDCl$_3$) δ (ppm): 7.79 (1H, d, J=15.8 Hz), 7.65-7.55 (2H, m), 7.48-7.35 (3H, m), 6.92 (1H, d, J=15.8 Hz), 4.11 (2H, t), 4.06 (3H, s), 3.98 (2H, t), 2.00-1.60 (4H, m), 1.08-0.95 (6H, m)

Reference Example 3

(E)-1,3-Dipropyl-8-(3,4,5-trimethoxystyryl)xanthine (Compound 9)

3,4,5-Trimethoxycinnamic acid (5.78 g, 24.3 mmol) and 6.36 g (33.2 mmol) of 3-(3-diethylaminopropyl)-1-ethylcarbodiimide hydrochloride were added to a mixture of dioxane (150 ml) and water (75 ml) containing 5.00 g (22.1 mmol) of 5,6-diamino-1,3-dipropyluracil. The resultant solution was stirred at room temperature at pH 5.5 for one hour. After the reaction, the solution was adjusted to pH 7 and extracted three times with chloroform. The combined extract was washed with a saturated aqueous solution of sodium chloride and dried over anhydrous sodium sulfate, followed by evaporation under reduced pressure. The residue was purified by silica gel column chromatography (eluent: 3% methanol/chloroform) to give 8.06 g (yield 82%) of (E)-6-amino-1,3-dipropyl-5-(3,4,5-trimethoxycinnamoylamino)uracil (Compound E) as an amorphous substance.

NMR (CDCl$_3$; 90 MHz) δ (ppm): 7.85 (1H, brs), 7.48 (1H, d, J=15.6 Hz), 6.67 (2H, s), 6.56 (1H, d, J=15.6 Hz), 5.80 (2H, brs), 4.00-3.70 (4H, m), 3.89 (9H, s), 1.80-1.45(4H, m), 1.15-0.80(6H, m)

To 10.02 g (22.5 mmol) of Compound E were added 100 ml of dioxane and 100 ml of an aqueous 2N.sodium hydroxide solution, and the solution was heated under reflux for 10 minutes. After cooling, the solution was neutralized, and deposited crystals were collected by filtration. Then, the collected crystals were recrystallized from dioxane/water to give 6.83 g (yield 91%) of Compound 9 as white crystals.

Melting Point: 161.8°–162.6° C. Elemental Analysis: C$_{22}$H$_{28}$N$_4$O$_5$ Calcd. (%): C, 61.66; H, 6.58; N, 13.07 Found (%): C, 61.73; H, 6.37; N, 13.08 IR (KBr) V$_{max}$ (cm$^{-1}$): 1702, 1643 NMR (CDCl$_3$; 90 MHz) δ (ppm): 12.87 (1H, brs), 7.72 (1H, d, J=16.3 Hz), 6.96 (1H, d, J=16.3 Hz), 6.81 (2H, s), 4.30-3.95 (4H, m), 3.92 (6H, s), 3.90 (3H, s), 2.10-1.50 (4H, m), 1.02 (2H, t), 0.90 (2H, t)

Reference Example 4

(E)-7-Methyl-1,3-dipropyl-8-(3,4,5-trimethoxystyryl)xanthine (Compound 5)

The same procedure as in Reference Example 1 was repeated using Compound 9 in place of Compound B to give 1.75 g (yield 84%) of Compound 5 as white needles.

Melting Point: 168.4°–169.1° C. (recrystallized from ethanol/water) Elemental Analysis: C$_{23}$H$_{30}$N$_4$O$_5$ Calcd. (%): C, 62.42; H, 6.83; N, 12.66 Found (%): C, 62.48; H, 6.60; N, 12.70 IR (KBr) V$_{max}$ (cm$^{-1}$): 1698, 1659 NMR (CDCl$_3$; 90 MHz) δ (ppm): 7.71 (1H, d, J=15.8 Hz), 6.86 (2H, s), 6.78 (1H, d, J=15.8 Hz), 4.30-3.95 (4H, m), 4.07 (3H, s), 3.93 (6H, s), 3.90 (3H, s), 2.05-1.50 (4H, m), 1.20-0.85 (6H, m)

Reference Example 5

(E)-8-(4-Methoxystyryl)-7-methyl-1,3-dipropylxanthine (Compound 6)

Substantially the same procedure as in Reference Example 1 was repeated using 2.00 g (8.85 mmol) of 5,6-diamino-1,3-dipropyluracil and 1.73 g (9.74 mmol) of 4-methoxycinnamic acid to give 2.29 g (overall yield 68%) of Compound 6.

Melting Point: 159.8°–161.3° C. (recrystallized from ethanol/water) Elemental Analysis: C$_{21}$H$_{26}$N$_4$O$_3$ Calcd. (%): C, 65.94; H, 6.85; N, 14.64 Found (%): C, 65.92; H, 6.90; N, 14.88 IR (KBr) V$_{max}$ (cm$^{-1}$): 1695, 1658 NMR (DMSO-d$_6$) δ (ppm): 7.72 (2H, d, J=8.8 Hz), 7.61 (1H, d, J=15.8 Hz), 7.16 (1H, d, J=15.8 Hz), 4.05-3.95 (2H, m), 4.00 (3H, s), 3.83 (2H, t), 3.80 (3H, s), 1.85-1.50 (4H, m), 1.00-0.85 (6H, m)

Reference Example 6

(E)-1,3-Diallyl-8-(3,4,5-trimethoxystyryl)xanthine (Compound 11)

Substantially the same procedure as in Reference Example 3 was repeated using 3.0 g (13.5 mmol) of 1,3-diallyl-5,6-diaminouracil and 3.55 g (14.9 mmol) of 3,4,5-trimethoxycinnamic acid to give 4.48 g (yield 75%) of (E)-1,3-diallyl-6-amino-5-(3,4,5-trimethoxycinnamoylamino)uracil (Compound F) as an amorphous substance.

NMR (CDCl$_3$; 90 MHz) δ (ppm): 7.90 (1H, brs), 7.56 (1H, d, J=16.0 Hz), 6.71 (2H, s), 6.57 (1H, d, J=16.0 Hz), 6.15-5.60(4H, m), 5.50-5.05(4H, m), 4.75-4.45 (4H, m), 3.90 (9H, s)

Substantially the same procedure as in Reference Example 3 was repeated using 4.34 g (9.82 mmol) of Compound F in place of Compound E to give 2.81 g (yield 68%) of Compound 11 as a pale yellowish green powder.

Melting Point 253.1°–255.4° C. (recrystallized from dioxane) Elemental Analysis: C$_{22}$H$_{24}$N$_4$O$_5$·1/2H$_2$O Calcd. (%): C, 60.96; H, 5.81; N, 12.93 Found (%): C, 61.05; H, 5.60; N, 12.91 IR (KBr) V$_{max}$ (cm$^{-1}$): 1704, 1645, 1583, 1510 NMR (CDCl$_3$) δ (ppm): 12.94 (1H, brs), 7.73 (1H, d, J=16.3 Hz), 7.05 (1H, d, J=16.3 Hz), 6.81 (2H, s), 6.12-5.92 (2H, m), 5.37-5.22 (4H, m), 4.83-4.76 (4H, m), 3.91 (6H, s), 3.90 (3H, s)

Reference Example 7

(E)-1,3-Diallyl-7-methyl-8-(3,4,5-trimethoxystyryl)xanthine (Compound 7)

Substantially the same procedure as in Reference Example 1 was repeated using 1.13 g (2.67 mmol) of Compound 11 in place of Compound B to give 620 mg (yield 53%) of Compound 7 as pale yellow needles.

Melting Point: 189.0°–191.1° C. (recrystallized from ethyl acetate) Elemental Analysis: C$_{23}$H$_{26}$N$_4$O$_5$ Calcd. (%): C, 63.00; H, 5.97; N, 12.77 Found (%): C, 63.00; H, 6.05; N, 12.85 IR (KBr) V$_{max}$ (cm$^{-1}$): 1699., 1660 NMR (CDCl$_3$; 90 MHz) δ (ppm): 7.78 (1H, d, J=16.0 Hz), 6.85 (2H, s), 6.84 (1H, d, J=16.0 Hz), 6.30-5.75 (2H, m), 5.45-5.10 (4H, m), 4.85-4.55 (4H, m), 4.07 (3H, s), 3.92 (6H, s), 3.90 (3H, s)

Reference Example 8

(E)-1,3-Dibutyl-8-(3,4,5-trimethoxystyryl)xanthine (Compound 8)

Substantially the same procedure as in Reference Example 1 was repeated using 4.75 g (18.7 mmol) of 5,6-diamino-1,3-dibutyluracil and 4.90 g (20.6 mmol) of 3,4,5-trimethoxycinnamic acid to give 10.6 g of crude (E)-6-amino-1,3-dibutyl-5-(3,4,5-trimethoxycinnamoylamino)uracil (Compound G) as an amorphous substance.

NMR (CDCl$_3$; 90 MHz) δ (ppm): 7.85 (1H, brs), 7.53 (1H, d, J=16.0 Hz), 6.72 (2H, s), 6.57 (1H, d, J=16.0 Hz), 5.74 (2H, brs), 4.05–3.70 (4H, m), 3.89 (9H, s), 1.80–1.15 (8H, m), 1.15–0.80 (6H, m)

Substantially the same procedure as in Reference Example 1 was repeated using 10.6 g of Compound G in place of Compound A to give 5.80 g (overall yield 68%) of Compound 8 as a white powder.

Melting Point: 205.8°–207.2° C. (recrystallized from ethyl acetate) Elemental Analysis: C$_{24}$H$_{32}$N$_4$O$_5$ Calcd. (%): C, 63.14; H, 7.06; N, 12.27 Found (%): C, 63.48; H, 6.71; N, 12.43 IR (KBr) V$_{max}$ (cm$^{-1}$): 1698, 1643, 1584, 1570, 1504 NMR (CDCl$_3$; 90 MHz) δ (ppm): 7.75 (1H, d, J=15.8 Hz), 6.98 (1H, d, J=15.8 Hz), 6.82 (2H, s), 4.30–4.12 (4H, m), 3.98 (6H, s), 3.93 (3H, s), 2.00–0.80 (14H, m)

Reference Example 9

(E)-1,3-Dibutyl-7-methyl-8-(3,4,5-trimethoxystyryl) xanthine (Compound 9)

Substantially the same procedure as in Reference Example 1 was repeated using 2.50 g (5.48 mmol) of Compound 8 obtained in Reference Example 8 in place of Compound B to give 2.36 g (yield 92%) of Compound 9 as a pale green powder.

Melting Point: 136.8°–137.3° C. (recrystallized from ethanol/water) Elemental Analysis: C$_{25}$H$_{34}$N$_4$O$_5$ Calcd. (%): C, 63.81; H, 7.28; N, 11.91 Found (%): C, 63.63; H, 6.93; N, 11.99 IR (KBr) V$_{max}$ (cm$^{-1}$): 1692, 1659 NMR (CDCl$_3$; 90 MHz) δ (ppm): 7.68 (1H, d, J=15.8 Hz), 6.80 (2H, s), 6.79 (1H, d, J=15.8 Hz), 4.30–3.90 (4H, m), 4.03 (3H, s), 3.95 (6H, s), 3.91 (3H, s), 1.90–1.10 (8H, m), 1.05–0.80 (6H, m)

Reference Example 10

(E)-8-(4-Methoxy-2,3-dimethylstyryl)-1,3-dipropylxanthine (Compound 13)

Substantially the same procedure as in Reference Example 1 was repeated using 2.31 g (10.24 mmol) of 5,6-diamino-1,3-dipropyluracil and 2.42 g (15.4 mmol) of 4-methoxy-2,3-dimethylcinnamic acid. Then, the resultant crude crystals were recrystallized from dioxane/water to give 1.96 g (yield 48%) of Compound 13 as a white powder.

Melting Point: 270.7°–271.3° C. Elemental Analysis: C$_{22}$H$_{28}$N$_4$O$_3$ Calcd. (%): C, 66.64; H, 7.11; N, 14.13 Found (%): C, 66.68; H, 7.20; N, 14.04 IR (KBr) V$_{max}$ (cm$^{-1}$): 1704, 1650, 1591, 1269 NMR (DMSO-d$_6$; 270 MHz) δ (ppm): 7.93 (1H, d, J=16.3 Hz), 7.57 (1H, d, J=8.9 Hz), 6.88 (1H, d, J=8.9 Hz), 6.82 (1H, d, J=16.3 Hz), 3.98 (2H, t, J=7.1 Hz), 3.86 (2H, t, J=7.3 Hz), 3.81 (3H, s), 2.32 (3H, s), 2.09 (3H, s), 1.80–1.55 (4H, m), 0.95–0.80 (6H, m)

Reference Example 11

(E)-8-(4-Methoxy-2,3-dimethylstyryl)-7-methyl-1,3-dipropylxanthine (Compound 14)

Substantially-the same procedure as in Reference Example 1 was repeated using 4.00 g (5.10 mmol) of Compound 13 obtained in Reference Example 10 in place of Compound B to give 1.73 g (yield 83%) of Compound 14 as yellow needles.

Melting Point: 171.0°–173.5° C. Elemental Analysis: C$_{23}$H$_{30}$N$_4$O$_3$ Calcd. (%): C, 67.29; H, 7.36; N, 13.64 Found (%): C, 66.87; H, 7.67; N, 13.51 IR (KBr) V$_{max}$ (cm$^{-1}$): 1697, 1659, 1593, 1493 NMR (CDCl$_3$; 270 MHz) δ (ppm): 8.07 (1H, d, J=15.3 Hz), 7.46 (1H, d, J=8.4 Hz), 6.77 (1H, d, J=8.4 Hz), 6.67 (1H, d, J=15.3 Hz), 4.12 (2H, t, J=7.3 Hz), 4.03 (3H, s), 3.98 (2H, t, J=7.3 Hz), 3.86 (3H, s), 2.39 (3H, s), 2.26 (3H, s), 1.85–1.50 (4H, m), 1.05–0.90 (6H, m)

Reference Example 12

(E)-8-(2,4-Dimethoxy-3-methylstyryl)-1,3-dipropylxanthine (Compound 15)

Substantially the same procedure as in Reference Example 1 was repeated using 1.25 g (5.52 mmol) of 5,6-diamino-1,3-dipropyluracil and 1.35 g (6.08 mmol) of 2,4-dimethoxy-3-methylcinnamic acid. Then, the resultant crude crystals were recrystallized from dioxane/water to give 1.14 g (yield 50%) of Compound 15 as white needles.

Melting Point: 255.2°–256.0° C. Elemental Analysis: C$_{22}$H$_{28}$N$_4$O$_4$

Calcd. (%): C, 64.06; H, 6.84; N, 13.58

Found (%): C, 63.77; H, 7.01; N, 13.42 IR (KBr) V$_{max}$ (cm$^{-1}$): 1694, 1650, 1594, 1495 NMR (DMSO-d$_6$;270 MHz) δ (ppm): 13.54 (1H, brs), 7.76 (1H, d, J=16.5 Hz), 7.59 (1H, d, J=8.9 Hz), 6.99 (1H, d, J=16.5 Hz), 6.84 (1H, d, J=8.9 Hz), 3.99 (2H, t, J=7.4 Hz), 3.85 (2H, t, J=7.3 Hz), 3.83 (3H, s), 3.70 (3H, s), 2.09 (3H, s), 1.80–1.55 (4H, m), 0.95–0.80 (6H, m)

Reference Example 13

(E)-8-(2,4-Dimethoxy-3-methylstyryl)-7-methyl-1,3-dipropylxanthine (Compound 16)

Substantially the same procedure as in Reference Example 1 was repeated using 1.10 g (2.67 mmol) of Compound 15 obtained in Reference Example 12 in place of Compound B. Then, the resultant crude crystals were recrystallized from ethanol/2-propanol to give 620 mg (yield 55%) of Compound 16 as pale yellow grains.

Melting Point: 191.4°–191.8 ° C. Elemental Analysis: C$_{23}$H$_{30}$N$_4$O$_4$ Calcd. (%): C, 64.76; H, 7.08; N, 13.13 Found (%): C, 4.84; H, 7.30; N, 12.89 IR (KBr) V$_{max}$ (cm$^{-1}$): 1695, 1654, 1274, 1107 NMR (CDCl$_3$; 270 MHz) δ (ppm): 7.91 (1H, d, J=15.8 Hz), 7.42 (1H, d, J=8.6 Hz), 6.98 (1H, d, J=15.8 Hz), 6.69 (1H, d, J=8.6 Hz), 4.11 (2H, t, J=7.4 Hz), 4.03 (3H, s), 4.03–3.95 (2H, m), 3.87 (3H, s), 3.77 (3H, s), 2.19 (3H, s), 1.85–1.55 (4H, m), 1.03–0.94 (6H, m)

Reference Example 14

(E)-8-[2-(1,4-Benzodioxan-6-yl)vinyl]-1,3-dipropylxanthine (Compound 17)

Substantially the same procedure as in Reference Example 1 was repeated using 1.35 g (5.96 mmol) of 5,6-diamino-1,3-dipropyluracil and 1.35 g (6.55 mmol) of 3-(1,4-benzodioxan-6-yl)acrylic acid. Then, the resultant crude crystals were recrystallized from ethanol/water to give 1.54 g (yield 65%) of Compound 17 as white needles.

Melting Point: >275° C. Elemental Analysis: C$_{21}$H$_{24}$N$_4$O$_4$ Calcd. (%): C, 63.62; H, 6.10; N, 14.13 Found (%): C, 63.57; H, 6.24; N, 14.36 IR (KBr) V$_{max}$ (cm$^{-1}$): 1693, 1636, 1582, 1511 NMR (DMSO-d$_6$; 270 MHz) δ (ppm): 12.52 (1H, brs), 7.63 (1H, d, J=16.2 Hz), 7.10–7.06

(2H, m), 6.95-6.86 (2H, m), 4.29 (4H, s), 4.15-4.10 (4H, m), 1.90-1.65 (4H, m), 1.05-0.95 (6H, m)

Reference Example 15

(E)-8-[2-(1,4-Benzodioxan-6-yl)vinyl]-7-methyl-1,3-dipropylxanthine (Compound 18)

Substantially the same procedure as in Reference Example 1 was repeated using 1.0 g (2.52 mmol) of Compound 17 obtained in Reference Example 14 in place of Compound B. Then, the resultant crude crystals were recrystallized from ethanol to give 840 mg (yield 81%) of Compound 18 as pale yellow needles. Melting Point: 181.9°–182.3° C. Elemental Analysis: $C_{22}H_{26}N_4O_4$ Calcd. (%): C, 64.37; H, 6.38; N, 13.64 Found (%): C, 64.56; H, 6.63; N, 13.92 IR (KBr) $V_{max}$ (cm$^{-1}$): 1693, 1651, 1510, 1288 NMR (CDCl$_3$; 270 MHz) δ (ppm): 7.67 (1H, d, J=15.5 Hz), 7.10 (2H, m), 6.88 (1H, d, J=8.3 Hz), 6.74 (1H, d, J=15.5 Hz), 4.30 (4H, m), 4.13-3.95 (4H, m), 4.03 (3H, s), 1.88-1.65 (4H, m), 1.03-0.94 (6H, m)

Reference Example 16

(E)-8-(3,4-Methylenedioxystyryl)-1,3-dipropylxanthine (Compound 19)

Substantially the same procedure as in Reference Example 1 was repeated using 4.25 g (18.8 mmol) of 5,6-diamino-1,3-dipropyluracil and 4.33 g (22.6 mmol) of 3,4-methylenedioxycinnamic acid. Then, the resultant crude crystals were recrystallized from dioxane to give 4.92 g (yield 69%) of Compound 19 as a pale yellow powder.

Melting Point: >270° C. Elemental Analysis: $C_{20}H_{22}N_4O_4 \cdot 0.75H_2O$ Calcd. (%): C, 60.50; H, 5.72; N, 14.43 Found (%): C, 60.67; H, 5.98; N, 14.15 IR (KBr) $V_{max}$ (cm$^{-1}$): 1688, 1648, 1499 NMR (DMSO-d$_6$; 270 MHz) δ (ppm): 13.49 (1H, brs), 7.56 (1H, d, J=16.3 Hz), 7.30 (1H, s), 7.07 (1H, d, J=8.4 Hz), 6.97-6.89 (2H, m), 6.07 (2H, s), 3.98 (2H, t, J=7.2 Hz), 3.85 (2H, t, J=7.3 Hz), 1.75-1.35 (4H, m), 0.95-0.80 (6H, m)

Reference Example 17

(E)-7-Methyl-8-(3,4-methylenedioxystyryl)-1,3-dipropylxanthine (Compound 20)

Substantially the same procedure as in Reference Example 1 was repeated using 3.0 g (7.85 mmol) of Compound 19 obtained in Reference Example 16 in place of Compound B. Then, the resultant crude crystals were recrystallized from toluene/cyclohexane to give 2.33 g (yield 75%) of Compound 20 as a pale green powder.

Melting Point: 151.7°–155.4° C. Elemental Analysis: $C_{21}H_{24}N_4O_4 \cdot 0.25H_2O$ Calcd. (%): C, 62.91; H, 6.16; N, 13.97 Found (%): C, 62.88; H, 6.25; N, 13.72 IR (KBr) $V_{max}$ (cm$^{-1}$): 1689, 1650, 1498, 1443 NMR (CDCl$_3$; 270 MHz) δ (ppm): 7.70 (1H, d, J=15.6 Hz), 7.10-6.95 (2H, m), 6.84 (1H, d, J=7.9 Hz), 6.72 (1H, d, J=15.6 Hz), 6.02 (2H, s), 4.10 (2H, t, J=7.3 Hz), 4.04 (3H, s), 3.97 (2H, t, J=7.3 Hz), 1.90-1.65 (4H, m), 1.05-0.90 (6H, m)

Reference Example 18

(E)-1,3-Dipropyl-8-(2,3,4-trimethoxystyryl)xanthine (Compound 21)

Substantially the same procedure as in Reference Example 1 was repeated using 2.00 g (8.85 mmol) of 5,6-diamino-1,3-dipropyluracil and 2.32 g (9.73 mmol) of 2,3,4-trimethoxycinnamic acid. Then, the resultant crude crystals were recrystallized from 2-propanol/water to give 1.84 g (yield 49%) of Compound 21 as pale yellow needles.

Melting Point: 246.5°–246.8° C. Elemental Analysis: $C_{22}H_{28}N_4O_5$ Calcd. (%): C, 61.66; H, 6.58; N, 13.07 Found (%): C, 61.50; H, 6.89; N, 13.06 IR (KBr) $V_{max}$ (cm$^{-1}$): 1703, 1651,, 1504 NMR (CDCl$_3$; 270 MHz) δ (ppm): 12.72 (1H, brs), 7.92 (1H, d, J=16.5 Hz), 7.31 (1H, d, J=8.7 Hz), 7.09 (1H, d, J=16.5 Hz), 6.71 (1H, d, J=8.7 Hz), 4.25-4.10 (4H, m), 3.95 (3H, s), 3.91 (3H, s), 3.90 (3H, s), 2.00-1.65(4H, m), 1.10-0.85 (6H, m)

Reference Example 19

(E)-7-Methyl-1,3-dipropyl-8-(2,3,4-trimethoxystyryl)xanthine (Compound 22)

Substantially the same procedure as in Reference Example 1 was repeated using 2.50 g (5.84 mmol) of Compound 21 obtained in Reference Example 18 in place of Compound B. Then, the resultant crude crystals were recrystallized from ethanol to give 1.70 g (yield 66%) of Compound 22 as yellow needles.

Melting Point: 153.5°–153.8° C. Elemental Analysis: $C_{23}H_{30}N_4O_5$ Calcd. (%): C, 62.42; H, 6.83; N, 12.66 Found (%): C, 62.77; H, 7.25; N, 12.65 IR (KBr) $V_{max}$ (cm$^{-1}$): 1699, 1657, 1590, 1497, 1439 NMR (CDCl$_3$; 270 MHz) δ (ppm): 7.88 (1H, d, J=15.8 Hz), 7.28 (1H, d, J=8.9 Hz), 7.02 (1H, d, J=15.8 Hz), 6.71 (1H, d, J=8.9 Hz), 4.25-3.95 (4H, m), 4.03 (3H, s), 3.97 (3H, s), 3.91 (3H, s), 3.90 (3H, s), 2.00-1.65 (4H, m), 1.10-0.85 (6H, m)

Reference Example 20

(E)-1,3-Dipropyl-8-(2,4,5-trimethoxystyryl)xanthine (Compound 23)

Substantially the same procedure as in Reference Example 1 was repeated using 2.00 g (8.85 mmol) of 5,6-diamino-1,3-dipropyluracil and 2.32 g (9.73 mmol) of 2,4,5-trimethoxycinnamic acid. Then, the resultant crude crystals were recrystallized from 2-propanol/water to give 870 mg (yield 23%) of Compound 23 as a pale yellow powder.

Melting Point: 254.5°–255.7 ° C. Elemental Analysis: $C_{22}H_{28}N_4O_5$ Calcd. (%): C, 61.66; H, 6.58; N, 13.07 Found (%): C, 61.944 H, 6.97; N, 13.06 IR (KBr) $V_{max}$ (cm$^{-1}$): 1693, 1650, 1517 NMR (CDCl$_3$; 270 MHz) δ (ppm): 12.53 (1H, brs), 7.97 (1H, d, J=16.5 Hz), 7.10 (1H, s), 6.99 (1H, d, J=16.5 Hz), 6.54 (1H, s), 4.25-4.10 (4H, m), 3.95 (3H, s), 3.90 (6H, s), 1.90-1.65 (4H, m), 1.01 (3H, t, J=7.6 Hz), 0.86 (3H, t, J=7.6 Hz)

Reference Example 21

(E)-7-Methyl-1,3-dipropyl-8-(2,4,5-trimethoxystyryl)xanthine (Compound 24)

Substantially the same procedure as in Reference Example 1 was repeated using 0.5 g (1.17 mmol) of Compound 23 obtained in Reference Example 20 in place of Compound B. Then, the resultant crude crystals were recrystallized from toluene/hexane to give 200 mg (yield 39%) of Compound 24 as a pale yellow powder. Melting Point: 195.5°–196.2° C. Elemental Analysis: $C_{23}H_{30}N_4O_5$ Calcd. (%): C, 62.42; H, 6.83; N, 12.66 Found (%): C, 62.14; H, 7.12; N, 12.56 IR (KBr) $V_{max}$ (cm$^{-1}$): 1688, 1653, 1515, 1439, 1214 NMR (CDCl$_3$; 270 MHz) δ (ppm): 7.93 (1H, d, J=15.8 Hz), 7.05 (1H, s), 6.94 (1H, d, J=15.8 Hz), 6.54 (1H, s), 4.15-3.90 (4H, m), 4.04 (3H, s), 3.95 (3H, s), 3.93 (3H, s), 3.91 (3H, s), 1.90-1.65 (4H, m), 1.03-0.94 (6H, m)

Reference Example 22

(E)-8-(2,4-Dimethoxystyryl)-1,3-dipropylxanthine (Compound 25)

Substantially the same procedure as in Reference Example 1 was repeated using 3.0 g (13.3 mmol) of 5,6-diamino-1,3-dipropyluracil and 3.04 g (14.60 mmol) of 2,4-dimethoxycinnamic acid. Then, the resultant crude crystals were recrystallized from dioxane/water to give 1.26 g (yield 24%) of Compound 25 as white crystals.

Melting Point: 273.1°–273.7° C. Elemental Analysis: $C_{21}H_{26}N_4O_4$ Calcd. (%): C, 63.30; H, 6.57; N, 14.06 Found (%): C, 62.94; H, 6.78; N, 14.03 IR (KBr) $V_{max}$ (cm$^{-1}$): 1693, 1645, 1506 NMR (DMSO-d$_6$;270 MHz) δ (ppm): 13.39 (1H, brs), 7.78 (1H, d, J=16.5 Hz), 7.54 (1H, d, J=8.2 Hz), 6.95 (1H, d, J=16.5 Hz), 6.63 (1H, d, J=2.3 Hz), 6.00 (1H, dd, J=8.2, 2.3 Hz), 4.01-3.85 (4H, m), 3.89 (3H, s), 3.82 (3H, s), 1.79-1.50 (4H, m), 0.93-0.87 (6H, m)

Reference Example 23

(E)-8-(2,4-Dimethoxystyryl)-7-methyl-1,3-dipropylxanthine (Compound 26)

Substantially the same procedure as in Reference Example 1 was repeated using 600 mg (1.51 mmol) of Compound 25 obtained in Reference Example 22 in place of Compound B. Then, the resultant crude crystals were recrystallized from hexane/ethyl acetate to give 556 mg (yield 90%) of Compound 26 as brown needles.

Melting Point: 167.6°–167.9° C. Elemental Analysis: $C_{22}H_{28}N_4O_4$ Calcd. (%): C, 64.06; H, 6.84; N, 13.58 Found (%): C, 63.98; H, 6.94; N, 13.61 IR (KBr) $V_{max}$ (cm$^{-1}$): 1691, 1653, 1603, 1437 NMR (CDCl$_3$; 270 MHz) δ (ppm): 7.92 (1H, d, J=15.8 Hz), 7.48 (1H, d, J=8.6 Hz), 6.98 (1H, d, J=15.8 Hz), 6.54 (1H, dd, J=8.6, 2.3 Hz), 6.50 (1H, d, J=2.3 Hz), 4.14-3.95 (4H, m), 4.02 (3H, s), 3.93 (3H, s), 3.86 (3H, s), 1.91-1.65 (4H, m), 1.03-0.94 (6H, m)

Reference Example 24

(E)-8-(4-Benzyloxy-3,5-dimethoxystyryl)-1,3-dipropylxanthine (Compound 27)

A mixture of 5.0 g (22.3 mmol) of 4-hydroxy-3,5-dimethoxycinnamic acid, 8.0 ml (66.9 mmol) of benzyl bromide, and potassium carbonate was stirred in 50 ml of dimethylformamide at 70° C. for 2 hours. Insoluble matters were filtered off and the filtrate was poured into 500 ml of water. The mixture was extracted three times with 100 ml of chloroform. The extract was washed twice with water and twice with a saturated aqueous solution of sodium chloride, and dried over anhydrous sodium sulfate, followed by evaporation under reduced pressure. To the residue were added 50 ml of an aqueous 2N sodium hydroxide solution and 50 ml of ethanol, followed by heating under reflux for 15 minutes. After cooling, the solution was adjusted to pH 3 with a concentrated hydrochloric acid solution and extracted three times with 50 ml of chloroform. The extract was washed with a saturated aqueous solution of sodium chloride, and dried over anhydrous sodium sulfate, followed by evaporation under reduced pressure. The residue was recrystallized from hexane to give 5.4 g (yield 77%) of (E)-4-benzyloxy-3,5-dimethoxycinnamic acid (Compound H) as pale yellow needles.

Melting Point: 101.8°–102.3° C. Elemental Analysis: $C_{18}H_{18}O_5$ Calcd. (%): C, 68.77; H, 5.77 Found (%): C, 68.95; H, 5.79 (KBr) $V_{max}$ (cm$^{-1}$): 2900 (br), 1683, 1630, 1579, 1502, 1281, 1129 NMR (CDCl$_3$; 90 MHz) δ (ppm): 7.80 (1H, d, J=16 Hz), 7.55-7.20 (5H, m), 6.80 (2H, s), 6.30 (1H, d, J=16 Hz), 5.08 (2H, s)

Substantially the same procedure as in Reference Example 1 was repeated using 3.30 g (14.5 mmol) of 5,6-diamino-1,3-dipropyluracil and 5.0 g (15.9 mmol) of Compound H. Then, the resultant crude crystals were recrystallized from ethanol/2-propanol to give 5.44 g (yield 74%) of Compound 27 as a white powder.

Melting Point: 221.1°–221.4° C. Elemental Analysis: $C_{28}H_{32}N_4O_5$ Calcd. (%): C, 66.65; H, 6.39; N, 11.10 Found (%): C, 66.65; H, 6.51; N, 11.01 IR (KBr) $V_{max}$ (cm$^{-1}$): 1704, 1637, 1582, 1505 NMR (CDCl$_3$; 90 MHz) δ (ppm): 7.69 (1H, d, J=16 Hz), 7.55-7.20 (5H, m), 6.96 (1H, d, J=16 Hz), 6.80 (2H, s), 5.08 (2H, s), 4.25-3.95 (4H, m), 3.88 (6H, s), 2.10-1.65 (4H, m), 1.20-0.80 (6H, m)

Reference Example 25

(E)-8-(4-Benzyloxy-3,5-dimethoxystyryl)-7-methyl-1,3-dipropylxanthine (Compound 28)

Substantially the same procedure as in Reference Example 1 was repeated using 8.20 g (14.5 mmol) of Compound 27 obtained in Reference Example 24 in place of Compound B. Then, the resultant crude crystals were recrystallized from 2-propanol/water to give 4.78 g (yield 64%) of Compound 28 as a white powder.

Melting Point: 164.7°–165.1° C. Elemental Analysis: $C_{29}H_{34}N_4O_5$ Calcd. (%): C, 67.16; H, 6.60; N, 10.80 Found (%): C, 67.01; H, 6.61;; N, 10.70 IR (KBr) $V_{max}$ (cm$^{-1}$): 1695, 1659, 1580, 1542, 1505, 1455, 1335 NMR (CDCl$_3$; 90 MHz) δ (ppm): 7.70 (1H, d, J=16 Hz), 7.55-7.20 (5H, m), 6.78 (2H, s), 6.72 (1H, d, J=16 Hz), 5.07 (2H, s), 4.25-3.95 (4H, m), 4.07 (3H, s), 3.89 (6H, s), 2.10-1.65 (4H, m), 1.20-0.85 (6H, m)

Reference Example 26

(E)-8-(2,3-Dimethoxystyryl)-1,3-dipropylxanthine (Compound 29)

Substantially the same procedure as in Reference Example 1 was repeated using 2.0 g (8.85 mmol) of 5,6-diamino-1,3-dipropyluracil and 2.2 g (10.6 mmol) of 2,3-dimethoxycinnamic acid. Then, the resultant crude crystals were recrystallized from chloroform/cyclohexane to give 1.26 g (yield 36%) of Compound 29 as yellow crystals.

Melting Point: 236.0°–236.5° C. Elemental Analysis: $C_{21}H_{26}N_4O_4$ Calcd. (%): C, 63.30; H, 6.57; N, 14.06 Found (%): C, 62.99; H, 6.71; N, 13.83 IR (KBr) $V_{max}$ (cm$^{-1}$): 1701, 1652, 1271 NMR (DMSO-d$_6$; 270 MHz) δ (ppm): 13.63 (1H, brs), 7.84 (1H, d, J=16.8 Hz), 7.28 (1H, d, J=6.8 Hz), 7.14-7.05 (3H, m), 4.00 (2H, t, J=7.3 Hz), 3.88-3.78

(2H, m), 3.83 (3H, s), 3.79 (3H, s), 1.80-1.50 (4H, m), 0.93-0.85 (6H, m)

Reference Example 27

(E)-8-(2,3-Dimethoxystyryl)-7-methyl-1,3-dipropylxanthine (Compound 30)

Substantially the same procedure as in Reference Example 1 was repeated using 1.5 g (3.77 mmol) of Compound 29 obtained in Reference Example 26 in place of Compound B. Then, the resultant crude crystals were recrystallized from toluene/cyclohexane to give 1.22 g (yield 79%) of Compound as pale brown needles.

Melting Point: 163.5°–163.7° C. Elemental Analysis: $C_{22}H_{28}N_4O_4$ Calcd. (%): C, 64.06; H, 6.84; N, 13.58 Found (%): C, 64.03; H, 7.12; N, 13.42 IR (KBr) $V_{max}$ (cm$^{-1}$): 1695, 1657, 1272 NMR (DMSO-$d_6$; 270 MHz) δ (ppm): 7.88 (1H, d, J=15.8 Hz), 7.50 (1H, dd, J=1.7, 7.6 Hz), 7.32 (1H, d, J=15.8 Hz), 7.17-7.06 (2H, m), 4.02 (3H, s), 4.02-3.98 (2H, m), 3.86-3.81 (2H, m), 3.84 (3H, s), 3.79 (3H, s), 1.80-1.65 (2H, m), 1.65-1.50 (2H, m), 0.93-0.84 (6H, m)

Reference Example 28

(E)-8-(3,4-Dimethylstyryl)-1,3-dipropylxanthine (Compound 31)

Substantially the same procedure as in Reference Example 1 was repeated using 5.90 g (26.0 mmol) of 5,6-diamino-1,3-dipropyluracil and 5.5 g (31.3 mmol) of 3,4-dimethylcinnamic acid. Then, the resultant crude crystals were recrystallized from dioxane/water to give 7.7 0 g (yield of Compound 31 as a white powder.

Melting Point: 252.7°–254.0° C. Elemental Analysis: $C_{21}H_{26}N_4O_2$ Calcd. (%): C, 68.83; H, 7.15; N, 15.29 Found (%): C, 68.43; H, 7.22; N, 15.22 IR (KBr) $V_{max}$ (cm$^{-1}$): 1700, 1648, 1490 NMR (DMSO-$d_6$; 270 MHz) δ (ppm): 7.40 (1H, d, J=16.2 Hz), 7.37 (1H, s), 7.29 (1H, d, J=7.2 Hz), 7.14 (1H, d, J=7.2 Hz), 6.95 (1H, d, J=16.2 Hz), 3.95 (2H, t, J=7.2 Hz), 3.83 (2H, t, J=7.4 Hz), 2.25 (3H, s, 2.23 (3H, s), 1.80-1.55 (4H, m), 1.00-0.90 (6H, m)

Reference Example 29

(E)-8-(3,4-Dimethylstyryl)-7-methyl-1,3-dipropylxanthine (Compound 32)

Substantially the same procedure as in Reference Example 1 was repeated using 6.50 g (17.8 mmol) of Compound 31 obtained in Reference Example 28 in place of Compound B. Then, the resultant crude crystals were recrystallized from ethanol/water to give 5.62 g (yield 83%) of Compound 32 as white needles.

Melting Point: 169.3°–170.3° C. Elemental Analysis: $C_{22}H_{28}N_4O_2$

Calcd. (%): C, 69.45; H, 7.42; N, 14.72

Found (%): C, 69.33; H, 7.42; N, 14.86 IR (KBr) $V_{max}$ (cm$^{-1}$): 1693, 1656 NMR (DMSO-$d_6$; 270 MHz) δ (ppm): 7.59 (1H, d, J=15.8 Hz), 7.58 (1H, s), 7.49 (1H, d, J=7.6 Hz), 7.26 (1H, d, J=15.8 Hz), 7.19 (1H, d, J=7.6 Hz), 4.02 (3H, s), 4.05-3.90 (2H, m), 3.84 (2H, t, J=7.4 Hz), 2.27 (3H, s), 2.25 (3H, s), 1.85-1.50 (4H, m), 1.00-0.85 (6H, m)

Reference Example 30

(E)-8-(3,5-Dimethoxystyryl)-1,3-dipropylxanthine (Compound 33)

Substantially the same procedure as in Reference Example 1 was repeated using 3.95 g (17.5 mmol) of 5,6-diamino-1,3-dipropyluracil and 4.0 g (19.2 mmol) of 3,5-dimethoxycinnamic acid. Then, the resultant crude crystals were recrystallized from dimethylformamide/water to give 3.78 g (yield 54%) of Compound 33 as a white powder.

Melting Point: 248.7°–250.3° C. Elemental Analysis: $C_{21}H_{26}N_4O_4$ Calcd. (%): C, 63.30; H, 6.58; N, 14.06 Found (%): C, 63.02; H, 6.71; N, 14.06 IR (KBr) $V_{max}$ (cm$^{-1}$): 1687, 1631, 1588, 1494 NMR (DMSO-$d_6$; 270 MHz) δ (ppm): 7.56 (1H, d, J=16.6 Hz), 7.08 (1H, d, J=16.6 Hz), 6.78 (2H, d, J=2.0 Hz), 6.50 (1H, t, J=2.0 Hz), 3.98 (2H, t, J=7.3 Hz), 3.85 (2H, t, J=7.3 Hz), 3.79 (6H, s), 1.80-1.50 (4H, m), 0.92-0.84 (6H, m)

Reference Example 31

(E)-8-(3,5-Dimethoxystyryl)-7-methyl-1,3-dipropylxanthine (Compound 34)

Substantially the same procedure as in Reference Example 1 was repeated using 3.23 g (8.27 mmol) of Compound 33 obtained in Reference Example 30 in place of Compound B. Then, the resultant crude crystals were recrystallized from acetonitrile to give 2.96 g (yield 87%) of Compound 34 as white needles.

Melting Point: 178.0°–178.2° C. Elemental Analysis: $C_{22}H_{28}N_4O_4$ Calcd. (%): C, 64.06; H, 6.84; N, 13.58 Found (%): C, 63.87; H, 7.11; N, 13.66 IR (KBr) $V_{max}$ (cm$^{-1}$): 1692, 1657, 1592 NMR (DMSO-$d_6$; 270 MHz) δ (ppm): 7.59 (1H, d, J=15.9 Hz), 7.35 (1H, d, J=15.9 Hz), 6.98 (2H, d, J=2.9 Hz), 6.51 (1H, t, J=2.9 Hz), 4.04 (3H, s), 4.10-3.95 (2H, m), 3.90-3.75 (2H, m), 3.80 (6H, s), 1.80-1.50 (4H, m), 1.00-0.80 (6H, m)

Reference Example 32

(E)-8-(3-Nitrostyryl)-1,3-dipropylxanthine (Compound 35)

Substantially the same procedure as in Reference Example 1 was repeated using 4.0 g (17.7 mmol) of 5,6-diamino-1,3-dipropyluracil and 3.8 g (19.5 mmol) of 3-nitrocinnamic acid. Then, the resultant crude crystals were recrystallized from toluene to give 3.86 g (yield 57%) of Compound 35 as pale yellow needles.

Melting Point: 256.5°–256.8° C. Elemental Analysis: $C_{19}H_{21}N_5O_4 \cdot 0.25C_6H_5CH_3$ Calcd. (%): C, 61.32; H, 5.70; N, 17.23 Found (%): C, 61.64; H, 5.94; N, 17.29 IR (KBr) $V_{max}$ (cm$^{-1}$): 1701, 1649, 1529, 1355 NMR (DMSO-$d_6$; 270 MHz) δ (ppm): 8.42 (1H, s), 8.19 (1H, d, J=8.0 Hz), 8.12 (1H, d, J=7.6 Hz), 7.80-7.65 (2H, m), 7.25 (1H, d, J=16.5 Hz), 4.00 (2H, t, J=7.2 Hz), 3.86 (2H, t, J=7.3 Hz), 1.80-1.55 (4H, m), 1.00-0.80 (6H, m)

Reference Example 33

(E)-7-Methyl-8-(3-nitrostyryl)-1,3-dipropylxanthine (Compound 36)

Substantially the same procedure as in Reference Example 1 was repeated using 3.20 g (8.36 mmol) of Compound 35 obtained in Reference Example 32 in place of Compound B. Then, the resultant crude crystals were recrystallized from toluene/cyclohexane to give 2.41 g (yield 73%) of Compound as yellow needles.

Melting Point: 218.2°–218.4° C. Elemental Analysis: $C_{20}H_{23}N_5O_4$ Calcd. (%): C, 60.44; H, 5.83; N, 17.62 Found (%): C, 59.94; H, 5.97; N, 17.43 IR (KBr) $V_{max}$ (cm$^{-1}$): 1699, 1662, 1521 NMR (DMSO-$d_6$; 270 MHz) δ (ppm): 8.70 (1H, m), 8.24 (1H, d, J=7.9 Hz), 8.19 (1H, dd, J=1.6, 7.6 Hz), 7.78 (1H, d, J=15.9 Hz), 7.71 (1H, t, J=7.9 Hz), 7.61 (1H, d, J=15.9 Hz), 4.08 (3H, s) 4.01 (2H, t, J=7.3 Hz), 3.85 (2H, t, J=7.3 Hz), 1.85-1.55 (4H, m), 0.91 (3H, t, J=7.5 Hz), 0.87 (3H, t, J=7.4 Hz)

Reference Example 34

(E)-8-(3-Fluorostyryl)-1,3-dipropylxanthine (Compound 37)

Substantially the same procedure as in Reference Example 1 was repeated using. 3.95 g (17.5 mmol) of 5,6-diamino-1,3-dipropyluracil and 3.19 g (19.2 mmol) of 3-fluorocinnamic acid. Then, the resultant crude crystals were recrystallized from dimethylformamide/water to give 4.67 g (yield 75%) of Compound 37 as a pale yellow powder.

Melting Point: 265.0°–265.9° C. Elemental Analysis: $C_{19}H_{21}N_4O_2F$ Calcd. (%): C, 64.03; H, 5.94; N, 15.72 Found (%): C, 64.02; H, 5.96; N, 15.46 IR (KBr) $V_{max}$ (cm$^{-1}$): 1701, 1646 NMR (DMSO-$d_6$; 270 MHz) δ (ppm): 7.63 (1H, d, J=16.3 Hz), 7.53-7.41 (3H, m), 7.23-7.15 (1H, m), 7.12 (1H, d, J=16.3 Hz), 3.99 (2H, t, J=7.0 Hz), 3.86 (2H, t, J=7.3 Hz), 1.80-1.50 (4H, m), 0.93-0.85 (6H, m)

Reference Example 35

(E)-8-(3-Fluorostyryl)-7-methyl-1,3-dipropylxanthine (Compound 38)

Substantially the same procedure as in Reference Example 1 was repeated using 2.92 g (8.19 mmol) of Compound 37 obtained in Reference Example 34 in place of Compound B. Then, the resultant crude crystals were recrystallized from toluene/cyclohexane to give 2.67 g (yield 88%) of Compound 38 as pale yellow needles.

Melting Point: 161.9°–162.0° C. Elemental Analysis: $C_{20}H_{23}N_4O_2F$ Calcd. (%): C, 64.85; H, 6.2.6; N, 15.12 Found (%): C, 64.61; H, 6.40; N, 14.86 IR (KBr) $V_{max}$ (cm$^{-1}$): 1693, 1656, 1544 NMR (DMSO-$d_6$; 270 MHz) δ (ppm): 7.80-7.60 (3H, m), 7.50-7.38 (2H, m), 7.19 (1H, dt, J=2.3, 8.3 Hz), 4.04 (3H, s), 4.00 (2H, t, J=7.3 Hz), 3.84 (2H, t, J=7.5 Hz), 1.80-1.55 (4H, m), 1.00-0.80 (6H, m)

Reference Example 36

(E)-8-(3-Chlorostyryl)-1,3-dipropylxanthine (Compound 39)

Substantially the same procedure as in Reference Example 1 was repeated using 3.95 g (17.5 mmol) of 5,6-diamino-1,3-dipropyluracil and 3.51 g (19.2 mmol) of 3-chlorocinnamic acid. Then, the resultant crude crystals were recrystallized from dimethylformamide/water to give 4.44 g (yield 67%) of Compound 39 as pale yellow crystals.

Melting Point: 258.9°–259.4° C. Elemental Analysis: $C_{19}H_{21}N_4O_2Cl$ Calcd. (%): C, 61.21; H, 5.68; N, 15.03 Found (%): C, 61.52; H, 5.73; N, 14.79 IR (KBr) $V_{max}$ (cm$^{-1}$): 1700, 1644, 1588, 1494 NMR (DMSO-$d_6$; 270 MHz) δ (ppm): 13.7 (1H, brs), 7.71-7.52 (3H, m), 7.48-7.39 (2H, m), 7.12 (1H, d, J=16.3 Hz), 3.99 (2H, t, J=7.0 Hz), 3.86 (2H, t, J=7.0 Hz), 1.80-1.50 (4H, m), 0.93-0.84 (6H, m)

Reference Example 37

(E)-8-(3-Chlorostyryl)-7-methyl-1,3-dipropylxanthine (Compound 40)

Substantially the same procedure as in Reference Example 1 was repeated using 2.85 g (7.66 mmol) of Compound 39 obtained in Reference Example 36 in place of Compound B. Then, the resultant crude crystals were recrystallized from ethanol to give 2.69 g (yield 91%) of Compound 40 as white needles.

Melting Point: 167.7°–167.9° C. Elemental Analysis: $C_{20}H_{23}N_4O_2Cl$ Calcd. (%): C, 62.0 g; H, 5.99; N, 14.48 Found (%): C, 62.00; H, 6.08; N, 14.27 IR (KBr) $V_{max}$ (cm$^{-1}$): 1691, 1657, 1543 NMR (DMSO-$d_6$; 270 MHz) δ (ppm): 7.99 (1H, s), 7.72 (1H, d, J=6.6 Hz), 7.63 (1H, d, J=15.8 Hz), 7.50-7.30 (3H, m), 4.05 (3H, s), 4.00 (2H, e, J=7.5 Hz), 3.84 (2H, t, J=7.4 Hz), 1.80-1.55 (4H, m), 1.00-0.80 (6H, m)

Reference Example 38

(E)-8-(2-Chlorostyryl)-1,3-dipropylxanthine (Compound 41)

Substantially the same procedure as in Reference Example 1 was repeated using 3.00 g (13.3 mmol) of 5,6-diamino-1,3-dipropyluracil and 2.67 g (14.6 mmol) of 2-chlorocinnamic acid. Then, the resultant crude crystals were recrystallized from toluene to give 3.72 g (yield 82%) of Compound 41 as white needles.

Melting Point: 269.4°–269.9° C. Elemental Analysis: $C_{19}H_{21}N_4O_2Cl$ Calcd. (%): C, 61.21; H, 5.68; N, 15.03 Found (%): C, 60.94; H, 5.69; N, 14.68 IR (KBr) $V_{max}$ (cm$^{-1}$): 1695, 1645, 1493 NMR (DMSO-$d_6$; 270 MHz) δ (ppm): 8.00-7.80 (2H, m), 7.55-7.50 (1H, m), 7.45-7.37 (2H, m), 7.12 (1H, d, J=16.5 Hz), 3.99 (2H, t, J=7.3 Hz), 3.86 (2H, t, J=7.4 Hz), 1.80-1.55 (4H, m), 1.00-0.80 (6H, m)

Reference Example 39

(E)-8-(2-Chlorostyryl)-7-methyl-1,3-dipropylxanthine (Compound 42)

Substantially the same procedure as in Reference Example 1 was repeated using 2.37 g (6.37 mmol) of Compound 41 obtained in Reference Example 38 in place of Compound B. Then, the resultant crude crystals were recrystallized from ethanol/water to give 1.88 g (yield 77%) of Compound 42 as yellow needles.

Melting Point 159.0°–159.9° C. Elemental Analysis: $C_{20}H_{23}N_4O_2Cl$ Calcd. (%): C, 62.09; H, 5.99; N, 14.48 Found (%): C, 61.75; H, 6.14; N, 14.45 IR (KBr) $V_{max}$ (cm$^{-1}$): 1696, 1650, 1544 NMR (DMSO-$d_6$; 270 MHz) δ (ppm): 8.10 (1H, dd, J=2.3, 7.3 Hz), 7.97 (1H, d, J=15.5 Hz), 7.55-7.50 (1H, m), 7.46-7.35 (3H, m), 4.05 (3H, s), 4.00 (2H, t, J=7.3 Hz), 3.84 (2H, t, J=7.3 Hz), 1.80-1.55 (4H, m), 1.00-0.80 (6H, m)

Reference Example 40

(E)-8-(2-Fluorostyryl)-1,3-dipropylxanthine (Compound 43)

Substantially the same procedure as in Reference Example 1 was repeated using 3.00 g (13.3 mmol) of 5,6-diamino-1,3-dipropyluracil and 2.43 g (14.6 mmol) of 2-fluorocinnamic acid. Then, the resultant crude crystals were recrystallized from dioxane/water to give 3.23 g (yield 68% of Compound 43 as white needles.

Melting Point: 258.8°–259.2° C. Elemental Analysis: $C_{19}H_{21}N_4O_2F$ Calcd. (%): C, 64.03; H, 5.94; N, 15.72 Found (%): C, 64.01; H, 6.11; N, 15.52 IR (KBr) $V_{max}$ ($cm^{-1}$): 1702, 1648 NMR (DMSO-$d_6$; 270 MHz) δ (ppm): 7.85-7.77 (2H, m), 7.46-7.32 (1H, m), 7.29-7.23 (2H, m), 7.16 (1H, d, J=16.5 Hz), 3.99 (2H, t, J=7.1 Hz), 3.86 (2H, t, J=7.3 Hz), 1.80-1.55 (4H, m), 1.00-0.80 (6H, m)

Reference Example 41

(E)-8-(2-Fluorostyryl)-7-methyl-1,3-dipropylxanthine (Compound 44)

Substantially the same procedure as in Reference Example 1 was repeated using 3.50 g (9.83 mmol) of Compound 43 obtained in Reference Example 40 in place of Compound B. Then, the resultant crude crystals were recrystallized from ethanol/water to give 1.23 g (yield 34%) of Compound 44 as white needles.

Melting Point: 155.5°–155.9° C. Elemental Analysis: $C_{20}H_{23}N_4O_2F$ Calcd. (%): C, 64.85; H, 6.26; N, 15.12 Found (%): C, 65.00; H, 6.44; N, 15.34 IR (KBr) $V_{max}$ ($cm^{-1}$): 1694, 1660 NMR (DMSO-$d_6$; 270 MHz) δ (ppm): 8.02 (1H, t, J=8.3 Hz), 7.75 (1H, d, J=15.5 Hz), 7.47-7.40 (2H, m), 7.40-7.25 (2H, m), 4.03 (3H, s), 4.00 (2H, t, J=7.4 Hz), 3.84 (2H, t, J=7.4 Hz), 1.80-1.55 (4H, m), 1.00-0.80 (6H, m)

Reference Example 42

(E)-8-(4-Methoxy-2,5-dimethylstyryl)-1,3-dipropylxanthine (Compound 45)

Substantially the same procedure as in Reference Example 1 was repeated using 2.5 g (11.1 mmol) of 5,6-diamino-1,3-dipropyluracil and 2.51 g (12.17 mmol) of 4-methoxy-2,5-dimethylcinnamic acid. Then, the resultant crude crystals were recrystallized from ethanol/water to give 1.98 g (yield 45%) of Compound 45 as white crystals.

Melting Point: 268.0°–269.2° C. Elemental Analysis: $C_{22}H_{28}N_4O_3$ Calcd. (%): C, 66.65; H, 7.11; N, 14.13 Found (%): C, 66.82; H, 7.34; N, 14.14 IR (KBr) ($cm^{-1}$): 1694, 1644, 1506, 1261 NMR (DMSO-$d_6$; 270 MHz) δ (ppm): 12.95 (1H, brs), 7.95 (1H, d, J=15.8 Hz), 7.42 (1H, s), 6.89 (1H, d, J=15.8 Hz), 6.66 (1H, s), 4.19-4.07 (4H, m), 3.86 (3H, s), 2.48 (3H, s), 2.21 (3H, s), 1.91-1.74 (4H, m), 1.02 (3H, t, J=6.9 Hz), 0.93 (3H, t, J=6.9 Hz)

Reference Example 43

(E)-8-(4-Methoxy-2,5-dimethylstyryl)-7-methyl-1,3-dipropylxanthine (Compound 46)

Substantially the same procedure as in Reference Example 1 was repeated using 973 mg (2.45 mmol) of Compound 45 obtained in Reference Example 42 in place of Compound B. Then, the resultant crude crystals were recrystallized from 2-propanol/water to give 966 mg (yield 96%) of Compound 46 as pale yellow needles.

Melting Point: 245.3°–246.3° C. Elemental Analysis: $C_{23}H_{30}N_4O_3$ Calcd. (%): C, 67.30; H, 7.36; N, 13.65 Found (%): C, 67.37; H, 7.51; N, 13.69 IR (KBr) $V_{max}$ ($cm^{-1}$): 1690, 1655, 1508, 1261 NMR (DMSO-$d_6$; 270 MHz) δ (ppm): 7.96 (1H, d, J=15.8 Hz), 7.41 (1H, s), 6.70 (1H, d, J=15.8 Hz), 6.66 (1H, s), 4.14-4.09 (2H, m), 4.05 (3H, s), 4.01-3.95 (2H, m), 2.48 (3H, s), 2.22 (3H, s), 1.91-1.77 (2H, m), 1.74-1.63 (2H, m), 1.03-0.94 (6H, m)

Reference Example 44

(Z)-8-(3,4-Dimethoxystyryl)-7-methyl-1,3-dipropylxanthine (Compound 47) (an about 6:4 mixture of Compound 47 and Compound 1)

Compound 1 (2.00 g, 4.85 mmol) obtained in Reference Example 1 was dissolved in 180 ml of chloroform, and the solution was irradiated with sunlight for 24 hours. After careful concentration of the reaction mixture, methanol was added thereto and deposited crystals were collected by filtration. The crystals were dried under reduced pressure to give 1.72 g (yield 86%) of a mixture of Compound 47 and Compound 1 as a pale yellow powder (The ratio of Compound 47 to Compound 1 was about 6:4 by NMR analysis).

Melting Point: 115.2°–119.4° C. Elemental Analysis: $C_{22}H_{28}N_4O_4$ Calcd. (%): C, 64.06; H, 6.84; N, 13.58 Found (%): C, 64.02; H, 6.82; N, 13.46 IR (KBr) $V_{max}$ ($cm^{-1}$): 1695, 1656, 1521 NMR (DMSO-$d_6$; 270 MHz) δ (ppm): 7.60 (1×4/10H, d, J=15.8 Hz), 7.40 (1×4/10H, d, J=2.0 Hz), 7.32-7.17 (2×4/10H+2×6/10H, m), 6.99 (1×4/10H, d, J=8.4 Hz), 6.94 (1×6/10H, d, J=12.7 Hz), 6.92 (1×6/10H, d, J=8.2 Hz), 6.39 (1×6/10H, d, J=12.7 Hz), 4.02 (3×4/10H, s), 4.10-3.80 (4H, m), 3.85 (3×4/10H, s), 3.80 (3×4/10H, s), 3.77 (6×6/10H, s), 3.64 (3×6/10H, s), 1.80-1.55 (4H, m), 1.00-0.85 (6H, m)

Reference Example 45

(E)-8-(4-Ethoxystyryl)-1,3-dipropylxanthine (Compound 48)

Substantially the same procedure as in Reference Example 1 was repeated using 3.0 g (13.3 mmol) of 5,6-diamino-1,3-dipropyluracil and 2.80 g (14.6 mmol) of 4-ethoxycinnamic acid. Then, the resultant crude crystals were recrystallized from dioxane to give 3.57 g (yield 70%) of Compound 48 as pale yellow needles.

Melting Point: 261.6°–262.0° C. Elemental Analysis: $C_{21}H_{26}N_4O_3$ Calcd. (%): C, 65.96; H, 6.85; N, 14.65 Found (%): C, 65.93; H, 7.13; N, 14.65 IR (KBr) $V_{max}$ ($cm^{-1}$): 1701, 1635, 1516, 1261 NMR (DMSO-$d_6$; 270 MHz) δ (ppm): 13.37 (1H, brs), 7.59 (1H, d, J=16.5 Hz), 7.55 (2H, d, J=8.6 Hz), 6.96 (2H, d, J=8.6 Hz), 6.88 (1H, d, J=16.5 Hz), 4.07 (2H, q, J=6.9 Hz), 3.99 (2H, t, J=7.3 Hz), 3.86 (2H, t, J=7.3 Hz), 1.73 (2H, m), 1.58 (2H, m), 1.34 (3H, t, J=6.9 Hz), 0.90 (3H, t, J=7.3 Hz), 0.87 (3H, t, J=7.3 Hz )

Reference Example 46

(E)-8-(4-Ethoxystyryl)-7-methyl-1,3-dipropylxanthine (Compound 49)

Substantially the same procedure as in Reference Example 1 was repeated using 2.0 g (5.23 mmol) of Compound 48 obtained in Reference Example 45 in place of Compound B. Then, the resultant crude crystals were recrystallized from hexane/ethyl acetate to give 1.72 g (yield 83%) of Compound 49 as pale green needles.

Melting Point: 174.7°–175.0° C. Elemental Analysis: $C_{22}H_{28}N_4O_3$ Calcd. (%): C, 66.65; H, 7.11; N, 14.13 Found (%): C, 66.60; H, 7.20; N, 14.27 IR (KBr) $V_{max}$ (cm$^{-1}$): 1702, 1660, 1515, 1252 NMR (CDCl$_3$; 270 MHz) δ (ppm): 7.74 (1H, d, J=15.8 Hz), 7.52 (2H, d, J=8.6 Hz), 6.92 (2H, d, J=8.6 Hz), 6.76 (1H, d, J=15.8 Hz), 4.09 (2H, t, J=7.6 Hz), 4.08 (2H, q, J=6.9 Hz), 4.04 (3H, s), 3.99 (2H, t, J=7.6 Hz), 1.44 (3H, t, J=6.9 Hz), 1.00 (3H, t, J=7.6 Hz), 0.97 (3H, t, J=7.6 Hz)

Reference Example 47

(E)-8-(4-Propoxystyryl)-1,3-dipropylxanthine (Compound 50)

Substantially the same procedure as in Reference Example 1 was repeated using 3.0 g (13.3 mmol) of 5,6-diamino-1,3-dipropyluracil and 3.01 g (14.6 mmol) of 4-propoxycinnamic acid. Then, the resultant crude crystals were recrystallized from dioxane/water to give 1.71 g (yield 33%) of Compound 50 as pale brown needles.

Melting Point: 248.3°–248.7° C. Elemental Analysis: $C_{22}H_{28}N_4O_3$ Calcd. (%): C, 66.65; H, 7.11; N, 14.13 Found (%): C, 66.50; H, 7.48; N, 14.25 IR (KBr) $V_{max}$ (cm$^{-1}$): 1694, 1649, 1514, 1253 NMR (DMSO-d$_6$; 270 MHz) δ (ppm): 13.34 (1H, brs), 7.58 (1H, d, J=16.5 Hz), 7.55 (2H, d, J=8.6 Hz), 6.99 (2H, d, J=8.6 Hz), 6.88 (1H, d, J=16.5 Hz), 4.01-3.95 (4H, m), 3.86 (2H, t, J=7.3 Hz), 1.78-1.70 (4H, m), 1.62-1.54 (2H, m), 0.98 (3H, t, J=7.3 Hz), 0.90 (3H, t, J=7.6 Hz), 0.87 (3H, t, J=7.6 Hz)

Reference Example 48

(E)-7-Methyl-8-(4-propoxystyryl)-1,3-dipropylxanthine (Compound 51)

Substantially the same procedure as in Reference Example 1 was repeated using 1.0 g (2.52 mmol) of Compound 50 obtained in Reference Example 47 in place of Compound B. Then, the resultant crude crystals were recrystallized from hexane/ethyl acetate to give 863 mg (yield 83%) of Compound 51 as pale yellow needles.

Melting Point: 172.6°–173.5° C. Elemental Analysis: $C_{23}H_{30}N_4O_3$ Calcd. (%): C, 67.30; H, 7.36; N, 13.65 Found (%): C, 67.15; H, 7.65; N, 13.58 IR (KBr) $V_{max}$ (cm$^{-1}$): 1699, 1658, 1514, 1252 NMR (CDCl$_3$; 270 MHz) δ (ppm): 7.74 (1H, d, J=15.8 Hz), 7.52 (2H, d, J=8.9 Hz), 6.92 (2H, d, J=8.9 Hz), 6.76 (1H, d, J=15.8 Hz), 4.13-3.94 (6H, m), 4.04 (3H, s), 1.90-1.62 (6H, m), 1.08-0.94 (9H, m)

Reference Example 49

(E)-8-(4-Butoxystyryl)-1,3-dipropylxanthine (Compound 52)

Substantially the same procedure as in Reference Example 1 was repeated using 3.0 g (13.3 mmol) of 5,6-diamino-1,3-dipropyluracil and 3.21 g (14.6 mmol) of 4-butoxycinnamic acid. Then, the resultant crude crystals were recrystallized from dioxane/water to give 3.47 g (yield 64% of Compound 52 as white needles.

Melting Point: 237.3°–238.9° C. Elemental Analysis: $C_{23}H_{30}N_4O_3$ Calcd. (%): C, 67.30; H, 7.36; N, 13.65 Found (%): C, 67.39; H, 7.45; N, 13.59 IR (KBr) $V_{max}$ (cm$^{-1}$): 1697, 1644, 1514, 1257 NMR (DMSO-d$_6$; 270 MHz) δ (ppm): 13.37 (1H, brs), 7.58 (1H, d, J=16.2 Hz), 7.55 (2H, d, J=8.6 Hz), 6.97 (2H, d, J=8.6 Hz), 6.88 (1H, d, J=16.2 Hz), 4.04-3.96 (4H, m), 3.86 (2H, t, J=7.3 Hz), 1.80-1.37 (8H, m), 0.97-0.84 (9H, m)

Reference Example 50

(E)-8-(4-Butoxystyryl)-7-methyl-1,3-dipropylxanthine (Compound 53)

Substantially the same procedure as in Reference Example 1 was repeated using 2.0 g (4.87 mmol) of Compound 52 obtained in Reference Example 49 in place of Compound B. Then, the resultant crude crystals were recrystallized from hexane/ethyl acetate to give 1.56 g (yield 75%) of Compound 53 as pale green needles.

Melting Point: 134.8°–135.6° C. Elemental Analysis: $C_{24}H_{32}N_4O_3$ Calcd. (%): C, 67.90; H, 7.59; N, 13.20 Found (%): C, 68.22; H, 7.88; N, 13.49 IR (KBr) $V_{max}$ (cm$^{-1}$): 1696, 1651, 1513, 1247 NMR (CDCl$_3$; 270 MHz) δ (ppm): 7.74 (1H, d, J=15.5 Hz), 7.52 (2H, d, J=8.6 Hz), 6.92 (2H, d, J=8.6 Hz), 6.76 (1H, d, J=15.5 Hz), 4.13-3.95 (6H, m), 4.04 (3H, s), 1.88-1.44 (8H, m), 1.03-0.94 (9H, m)

Reference Example 51

(E)-8-(3,4-Dihydroxystyryl)-7-methyl-1,3-dipropylxanthine (Compound 54)

Compound 1 (770 mg, 1.87 mmol) obtained in Reference Example 1 was dissolved in 15 ml of methylene chloride. To the solution was added 5.6 ml (5.6 mmol) of boron tribromide (1.0M methylene chloride solution) under ice cooling in argon atmosphere, and the mixture was stirred overnight at room temperature. Methanol was added thereto and the mixture was separated with chloroform-an aqueous solution of sodium bicarbonate. The organic layer was washed with a saturated aqueous solution of sodium chloride and dried over anhydrous sodium sulfate, followed by evaporation under reduced pressure. The residue was purified by silica gel column chromatography to give 550 mg (yield 77%) of Compound 54 as a yellow solid, which was then triturated with ether to give a yellow powder.

Melting Point: 250.1°–251.4° C. Elemental Analysis: $C_{20}H_{24}N_4O_4$ Calcd. (%): C, 62.49; H, 6.29; N, 14.57 Found (%): C, 62.27; H, 6.48; N, 14.74 IR (KBr) $V_{max}$ (cm$^{-1}$): 1680, 1640, 1543, 1306 NMR (DMSO-d$_6$; 270 MHz) δ (ppm): 9.31 (1H, brs), 8.95 (1H, brs), 7.49 (1H, d, J=15.8 Hz), 7.15 (1H, d, J=2.0 Hz), 7.04 (1H, dd, J=7.9, 2.0 Hz), 6.98 (1H, d, J=15.8 Hz), 6.78 (1H, d, J=7.9 Hz), 3.99 (2H, t, J=7.6 Hz), 3.98 (3H, s), 3.84 (2H, t, J=7.4 Hz), 1.73 (2H, m), 1.57 (2H, m), 0.90 (3H, t, J=7.4 Hz), 0.87 (3H, t, J=7.4 Hz)

Reference Example 52

(E)-8-(3,4-Diethoxystyryl)-7-methyl-1,3-dipropylxanthine (Compound 55)

Compound 54 (390 mg, 1.01 mmol) obtained in Reference Example 51 was dissolved in 10 ml of dimethylformamide. To the solution were added 0.20 ml (2.50 mmol) of ethyl iodide and 420 mg (3.04 mmol) of potassium carbonate, and the mixture was stirred overnight at room temperature. Water was added thereto to dissolve potassium carbonate and deposited crystals were collected by filtration. The collected crude crystals were recrystallized from hexane/ethyl acetate to give 237 mg (yield 53%) of Compound 55 as pale yellow needles.

Melting Point: 173.8°–174.0° C. Elemental Analysis: $C_{24}H_{32}N_4O_4$ Calcd. (%): C, 65.44; H, 7.32; N, 12.72 Found (%): C, 65.42; H, 7.48; N, 12.62 IR (KBr) $v_{max}$ (cm$^{-1}$): 1694, 1653, 1508, 1268 NMR (CDCl$_3$; 270 MHz) δ (ppm): 7.71(1H, d, J=15.5 Hz), 7.15 (1H, dd, J=8.3, 2.0 Hz), 7.10 (1H, d, J=2.0 Hz), 6.89 (1H, d, J=8.3 Hz), 6.74 (1H, d, J=15.5 Hz), 4.16 (2H, q, J=6.9 Hz), 4.14 (2H, q,: J=6.9 Hz), 4.08–3.95 (4H, m), 4.05 (3H, s), 1.91–1.76 (2H, m), 1.76–1.62 (2H, m), 1.49 (3H, t, J=6.9 Hz), 1.48 (3H, t, J=6.9 Hz), 1.00(3H, t, J=7.6 Hz), 0.97 (3H, t, J=7.6 Hz)

Reference Example 53

(E)-8-(3-Bromo-4-methoxystyryl)-1,3-dipropylxanthine (Compound 56)

Substantially the same procedure as in Reference Example 1 was repeated using 3.0 g (13.3 mmol) of 5,6-diamino-1,3-dipropyluracil and 3.75 g (14.6 mmol) of 3-bromo-4-methoxycinnamic acid. Then, the resultant crude crystals were recrystallized from dioxane to give 3.43 g (yield 58%) of Compound 56 as yellow needles.

Melting Point: 279.8°–280.6° C. Elemental Analysis: $C_{20}H_{23}N_4O_3Br$ Calcd. (%): C, 53.70; H, 5.18; N, 12.52 Found (%): C, 53.77; H, 5.20; N, 12.49 IR (KBr) $v_{max}$ (cm$^{-1}$): 1685, 1633, 1599, 1503, 1279 NMR (DMSO-d$_6$; 270 MHz) δ (ppm): 13.42 (1H, brs), 7.85 (1H, d, J=2.0 Hz), 7.61(1H, dd, J=8.4, 2.0 Hz), 7.55 (1H, d, J=16.3 Hz), 7.15 (1H, d, J=8.4 Hz), 6.94 (1H, d, J=16.3 Hz), 3.98 (2H, t, J=7.4 Hz), 3.89(3H, s), 3.86(2H, t, J=7.4 Hz), 1.80–1.52(4H, m), 0.89(6H, q, J=7.4 Hz)

Reference Example 54

(E)-8-(3-Bromo-4-methoxystyryl)-7-methyl-1,3-dipropylxanthine (Compound 57)

Substantially the same procedure as in Reference Example 1 was repeated using 750 mg (1.68 mmol) of Compound 56 obtained in Reference Example 53 in place of Compound B. Then, the resultant crude crystals were recrystallized from hexane/ethyl acetate to give 588 mg (yield 76%) of Compound 57 as pale yellow needles.

Melting Point: 209.4°–210.8° C. Elemental Analysis: $C_{21}H_{25}N_4O_3Br$ Calcd. (%): C, 54.67; H, 5.46; N, 12.14 Found (%): C, 54.47; H, 5.51; N, 11.91 IR (KBr) $v_{max}$ (cm$^{-1}$): 1693, 1656, 1542, 1500, 1264 NMR (CDCl$_3$; 270 MHz) δ (ppm): 7.83(1H, d, J=2.0 Hz), 7.68 (1H, d, J=15.8 Hz), 7.48(1H, dd, J=8.4, 2.0 Hz), 6.92 (1H, d, J=8.4 Hz), 6.78(1H, d, J=15.8 Hz), 4.13–4.07 (2H, m), 4.06 (3H, s), 4.01–3.97 (2H, m), 3.95 (3H, s), 1.90–3.65 (4H, m), 1.00 (3H, t, J=7.4 Hz), 0.97 (3H, t, J=7.4 Hz)

Reference Example 55

(E)-8-(2-Bromo-4,5-dimethoxystyryl)-1,3-dipropylxanthine (Compound 58)

Substantially the same procedure as in Reference Example 1 was repeated using 2.0 g (8.85 mmol) of 5,6-diamino-1,3-dipropyluracil and 2.80 g (9.75 mmol) of 2-bromo-4,5-dimethoxycinnamic acid. Then, the resultant crude crystals were recrystallized from dioxane to give 2.38 g (yield 56%) of Compound 58 as pale yellow needles.

Melting Point: 248.2°–249.5° C. Elemental Analysis: $C_{21}H_{25}N_4O_4Br$ Calcd. (%): C, 52.84; H, 5.28; N, 11.74 Found (%): C, 52.73; H, 5.31; N, 11.45 IR (KBr) $v_{max}$ (cm$^{-1}$): 1697, 1643, 1506, 1263 NMR (DMSO-d$_6$; 270 MHz) δ (ppm): 13.75(1H, brs), 7.81 (1H, d, J=16.3 Hz), 7.39(1H, s), 7.20(1H, s), 7.09 (1H, d, J=16.3 Hz), 4.00–3.82(4H, m), 3.86(3H, s), 3.82 (3H, s), 1.76–1.54 (4H, m), 0.92–0.85 (6H, m)

Reference Example 56

(E)-8-(2-Bromo-4,5-dimethoxystyryl)-7-methyl-1,3-dipropylxanthine (Compound 59)

Substantially the same procedure as in Reference Example 1 was repeated using 800 mg (1.68 mmol) of Compound 58 obtained in Reference Example 55 in place of Compound B. Then, the resultant crude crystals were recrystallized from dioxane to give 766 mg (yield 93%) of Compound 59 as yellow needles.

Melting Point: 228.8°–229.4° C. Elemental Analysis: $C_{22}H_{27}N_4O_4Br$ Calcd. (%): C, 53.78; H, 5.54; N, 11.40 Found (%): C, 53.76; H, 5.67; N, 11.16 IR (KBr) $v_{max}$ (cm$^{-1}$): 1688, 1650, 1509, 1266 NMR (CDCl$_3$; 270 MHz) δ (ppm): 8.01(1H, d, J=15.8 Hz), 7.11 (1H, s), 7.09 (1H, s), 6.75 (1H, d, J=15.8 Hz), 4.15–3.92 (4H, m), 4.08 (3H, s), 3.95 (3H, s), 3.92 (3H, s), 1.91–1.77 (2H, m), 1.74–1.63 (2H, m), 1.03–0.94 (6H, m)

Reference Example 57

(E)-8-(3-Bromo-4,5-dimethoxystyryl)-1,3-dipropylxanthine (Compound 60)

Substantially the same procedure as in Reference Example 1 was repeated using 1.5 g (6.64 mmol) of 5,6-diamino-1,3-dipropyluracil and 2.10 g (7.31 mmol) of 3-bromo-4,5-dimethoxycinnamic acid. Then, the resultant crude crystals were recrystallized from dioxane/water to give 2.11 g (yield 67%) of Compound 60 as white needles.

Melting Point: 276.7°–277.5° C. Elemental Analysis: $C_{21}H_{25}N_4O_4Br$ Calcd. (%): C, 52.84; H, 5.28; N, 11.74 Found (%): C, 52.72; H, 5.16; N, 11.56 IR (KBr) $v_{max}$ (cm$^{-1}$): 1701, 1650, 1562, 1498 NMR (DMSO-d$_6$; 270 MHz) δ (ppm): 13.44(1H, brs), 7.55 (1H, d, J=16.3 Hz), 7.39(1H, d, J=2.0 Hz), 7.36(1H, d, J=2.0 Hz), 7.07(1H, d, J=16.3 Hz), 3.99(2H, t, J=7.4 Hz), 3.91(3H, s), 3.86(2H, t, J=7.4 Hz), 3.78 (3H, s), 1.77–1.52(4H, m), 0.93–0.85(6H, m)

Reference Example 58

(E)-8-(3-Bromo-4,5-dimethoxystyryl)-7-methyl-1,3-dipropylxanthine (Compound 61)

Substantially the same procedure as in Reference Example 1 was repeated using 1.0 g (2.10 mmol) of Compound 60 obtained in Reference Example 57 in place of Compound B. Then, the resultant crude crystals were recrystallized from hexane/ethyl acetate to give 952 mg (yield 93%) of Compound 61 as pale yellow needles.

Melting Point: 180.9°–181.6° C. MS-EI m/e: 490, 492 IR (KBr) $v_{max}$ (cm$^{-1}$): 1691, 1648, 1542, 1493 NMR (CDCl$_3$; 270 MHz) δ (ppm): 7.68(1H, d, J=15.8 Hz), 7.42 (1H, d, J=2.0 Hz), 7.02 (1H, d, J=2.0 Hz), 6.80 (1H, d, J=15.8 Hz), 4.13–3.95 (4H, m), 4.08 (3H, s), 3.94(3H, s), 3.90(3H, s), 1.90–1.65(4H, m), 1.01 (3H, t, J=7.4 Hz), 0.97(3H, t, J=7.4 Hz)

Reference Example 59

(E)-8-[2-(4-Methoxynaphthyl)vinyl]-
1,3-dipropylxanthine (Compound 62)

Substantially the same procedure as in Reference Example 1 was repeated using 3.0 g (13.3 mmol) of 5,6-diamino-1,3-dipropyluracil and 3.33 g (14.6 mmol) of 3-(4-methoxynaphthyl)acrylic acid. Then, the resultant crude crystals were recrystallized from dioxane/water to give 3.12 g (yield 56%) of Compound 62 as yellow needles.

Melting Point: >280° C. Elemental Analysis: $C_{24}H_{26}N_4O_3$ Calcd. (%): C, 68.88; H, 6.26; N, 13.39 Found (%): C, 68.90; H, 6.38; N, 13.49 IR (KBr) $v_{max}$ (cm$^{-1}$): 1699, 1649, 1486, 1273 NMR (DMSO-$d_6$; 270 MHz) δ (ppm): 13.58 (1H, brs), 8.43 (1H, d, J=16.5 Hz), 8.36(1H, d, J=8.6 Hz), 8.24 (1H, d, J=8.6 Hz), 7.98 (1H, d, J=7.8 Hz), 7.70–7.54 (2H, m), 7.12–7.06(2H, m), 4.03(3H, s), 4.02–3.86 (4H, m), 1.79–1.56(4H, m), 0.92(3H, s), 0.89(3H, s)

Reference Example 60

(E)-8-[2-(4-Methoxynaphthyl)vinyl]-7-methyl-
1,3-dipropylxanthine (Compound 63)

Substantially the same procedure as in Reference Example 1 was repeated using 1.6 g (3.82 mmol) of Compound obtained in Reference Example 59 in place of Compound B. Then, the resultant crude crystals were recrystallized from ethyl acetate to give 1.25 g (yield 76%) of Compound 63 as pale yellow plates.

Melting Point: 212.6°–213.9° C. Elemental Analysis: $C_{25}H_{28}N_4O_3$ Calcd. (%): C, 69.43; H, 6.52; N, 12.95 Found (%): C, 69.46; H, 6.68; N, 12.95 IR (KBr) $v_{max}$ (cm$^{-1}$): 1701, 1650, 1486, 1439, 1267 NMR (CDCl$_3$; 270 MHz) δ (ppm): 8.52(1H, d, J=15.5 Hz), 8.34(1H, d, J=8.3 Hz), 8.23(1H, d, J=8.6 Hz), 7.77 (1H, d, J=8.3 Hz), 7.66–7.52(2H, m), 6.89(1H, d, J=15.5 Hz), 6.87 (1H, d, J=8.3 Hz), 4.18–4.11 (2H, m), 4.07 (3H, s), 4.06 (3H, s), 4.02–3.97 (2H, m), 1.95–1.64(4H, m), 1.03(3H, t, J=7.3 Hz), 0.98(3H, t, J=7.3 Hz)

Reference Example 61

(E)-8-(3-Hydroxy-4-methoxystyryl)-7-methyl-
1,3-dipropylxanthine (Compound 64)

Compound 54 (500 mg, 1.30 mmol) obtained in Reference Example 51 was dissolved in 10 ml of dimethylformamide. To the solution were added 0.40 ml (6.43 mmol) of methyl iodide and 400 mg (6.50 mmol) of lithium carbonate, and the mixture was stirred at 80° C. for 5 hours. Water was added thereto to dissolve lithium carbonate and deposited crystals were collected by filtration. The collected crude crystals were dissolved in chloroform, washed with a saturated aqueous solution of sodium chloride and dried over anhydrous sodium sulfate, followed by evaporation under reduced pressure. The residue was purified by silica gel column chromatography (eluent: chloroform), followed by recrystallization from hexane/ethyl acetate to give 162 mg (yield 31%) of Compound 64 as yellow grains.

Melting Point: 200.3°–203.6° C. MS-EI m/e: 398 IR (KBr) $v_{max}$ (cm$^{-1}$): 1683, 1642, 1512, 1278 NMR (DMSO-$d_6$; 270 MHz) δ (ppm): 8.98(1H, brs), 7.52 (1H, d, J=15.5 Hz), 7.22 (1H, d, J=2.0 Hz), 7.15 (1H, dd, J=8.3, 2.0 Hz), 7.06 (1H, d, J=15.5 Hz), 6.96 (1H, d, J=8.3 Hz), 4.02–3.97 (2H, m), 4.00 (3H, s), 3.84–3.82 (2H, m), 3.82 (3H, s), 1.80–1.50 (4H, m), 0.90 (3H, t, J=7.3 Hz), 0.87(3H, t, J=7.3 Hz)

Reference Example 62

(Z)-8-(3,4-Dimethoxystyryl)-7-methyl-
1,3-dipropylxanthine (Compound 65)

Compound 1 (1.00 g, 2.42 mmol) obtained in Reference Example 1 was dissolved in 1.6 L of methanol, and the solution was irradiated with sunlight for 5 hours. After evaporation under reduced pressure, the residue was purified by high performance liquid chromatography (column: YMC Pack ODS-A, SH-365-10, S-10; 30 mmØ×500 mm, flow rate: 90 ml/min, detection: UV 246 nm) to give 565 mg (yield 57%) of Compound 65 as white needles.

Melting Point: 126.9°–127.2° C. Elemental Analysis: $C_{22}H_{28}N_4O_4$ Calcd. (%): C, 64.06; H, 6.84; N, 13.58 Found (%): C, 64.12; H, 7.09; N, 13.54 IR (KBr) $v_{max}$ (cm$^{-1}$): 1696, 1654, 1542, 1521 NMR (270 MHz; DMSO-$d_6$) δ (ppm): 7.28 (1H, d, J=8.4 Hz), 7.20 (1H, S), 6.94 (1H, d, J=12.7 Hz), 6.92 (1H, d, J=8.4 Hz), 6.39(1H, d, J=12.7 Hz), 3.93 (2H, t, J=7.4 Hz), 3.84 (2H, t, J=6.9 Hz), 3.77(6H, s), 3.64 (3H, s), 1.75–1.50 (4H, m), 0.86 (3H, t, J=7.4 Hz), 0.85 (3H, t, J=7.4 Hz)

Reference Example 63

(E)-8-(3,4-Dimethoxystyryl)-7-ethyl-
1,3-dipropylxanthine (Compound 66)

Substantially the same procedure as in Reference Example 1 was repeated using 1.5 g (3.77 mmol) of Compound B obtained in Reference Example 1 and 0.60 ml (7.54 mmol) of ethyl iodide. Then, the resultant crude crystals were recrystallized from ethanol/water to give 1.38 g (yield 87%) of Compound 66 as white needles.

Melting Point: 107.6°–107.9° C. Elemental Analysis: $C_{23}H_{30}N_4O_4$ Calcd. (%): C, 64.77; H, 7.09; N, 13.14 Found (%): C, 64.81; H, 7.28; N, 13.21 IR (KBr) $v_{max}$ (cm$^{-1}$): 1695, 1655, 1515, 1265 NMR (270MHz; CDCl$_3$) δ (ppm): 7.63 (1H, d, J=15.8 Hz), 7.42 (1H, d, J=1.7 Hz), 7.32(1H, dd, J=8.6, 1.7 Hz), 7.23 (1H, d, J=15.8 Hz), 6.99 (1H, d, J=8.6Hz), 4.51 (2H, q, J=6.9 Hz), 3.99(2H, t, J=7.2 Hz), 3.87–3.80 (2H, m), 3.85(3H, s), 3.80(3H; s), 1.80–1.45(4H, m), 1.33 (3H, t, J=6.9 Hz), 0.94–0.85 (6H, m)

Reference Example 64

(E)-8-(3,4-Dimethoxystyryl)-7-propargyl-
1,3-dipropylxanthine (Compound 67)

Substantially the same procedure as in Reference Example 1 was repeated using 1.5 g (3.77 mmol) of Compound B obtained in Reference Example 1 and 0.67 ml (7.54 mmol) of propargyl bromide. Then, the resultant crude crystals were recrystallized from cyclohexane/toluene to give 1.35 g (yield 82%) of Compound 67 as a yellow powder.

Melting Point: 153.4°–154.8° C. Elemental Analysis: $C_{24}H_{28}N_4O_4$ Calcd. (%): C, 66.04; H, 6.47; N, 12.84 Found (%): C, 66.18; H, 6.74.; N, 12.87 IR (KBr) $v_{max}$ (cm$^{-1}$): 1684, 1647, 1510, 1270 NMR (270 MHz; CDCl$_3$) δ (ppm): 7.66(1H, d, J=15.7 Hz), 7.41(1H, d, J=1.3 Hz), 7.32 (1H, dd, J=8.5, 1.3 Hz), 7.26 (1H, d, J=15.7 Hz), 7.02 (1H, d, J=8.5 Hz), 5.43 (2H, d, J=2.0 Hz), 4.00(2H, t, J=7.3 Hz), 3.87–3.81 (2H, m), 3.85(3H, s), 3.81(3H, s), 3.48(1H, t, J=2.0 Hz), 1.80–1.45(4H, m), 0.94–0.85(6H, m)

Reference Example 65

(E)-8-[3,4-Bis(methoxymethoxy)styryl]-7-methyl-1,3-dipropylxanthine (Compound 68)

Compound 54 (300 mg, 0.78 mmol) obtained in Reference Example 51 was dissolved in 6 ml of tetrahydrofuran. To the solution were added 1.64 ml (9.41 mmol) of diisopropylethylamine and 1.64 ml (7.12 mmol) of chloromethylmethyl ether under ice-cooling in a stream of argon, and the mixture was heated under reflux for 3 hours. Ice was added to the reaction solution and the mixture was separated with chloroform-a saturated aqueous saline solution. The organic layer was dried over anhydrous sodium sulfate, followed by evaporation under reduced pressure. The residue was purified by silica gel column chromatography (eluent: hexane/ethyl acetate) and recrystallized from hexane/ethyl acetate to give 211 mg (yield 57%) of Compound 68 as white needles.

Melting Point: 172.2.°–172.6° C. Elemental Analysis: $C_{24}H_{32}N_4O_6$ Calcd. (%): C, 61.01; H, 6.82; N, 11.86 Found (%): C, 61.16; H, 7.00; N, 11.88 IR (KBr) $v_{max}$ (cm$^{-1}$): 1688, 1658, 1509, 1267 NMR (270 MHz; CDCl$_3$) δ (ppm): 7.22 (1H, d, J=15.8 Hz), 7.39 (1H, d, J=1.3Hz), 7.25–7.16(2H, m), 6.77(1H, d, J=15.8 Hz), 5.30 (2H, s), 5.28 (2H, s), 4.13–3.95 (4H, m), 4.04 (3H, s), 3.56 (3H, s), 3.54 (3H, s), 1.91–1.61 (4H, m), 1.00(3H, t, J=7.6Hz), 0.97(3H, t, J=7.6Hz)

Reference Example 66

(E)-1,3-Diallyl-8-(3,4-dimethoxystyryl)xanthine (Compound 69)

Substantially the same procedure as in Reference Example 1 was repeated using 2.9 g (13.1 mmol) of 1,3-diallyl-5,6-diaminouracil and 2.99 g (14.4 mmol) of 3,4-dimethoxycinnamic acid. Then, the resultant crude crystals were recrystallized from dioxane/water to give 2.80 g (yield) of Compound 69 as pale yellow flocculent precipitates.

Melting Point: 251.6°–252.4° C. Elemental Analysis: $C_{21}H_{22}N_4O_3$ Calcd. (%): C, 63.95; H, 5.62; N, 14.20 Found (%): C, 63.67; H, 5.61; N, 14.14 IR (KBr) $v_{max}$ (cm$^{-1}$): 1698, 1644, 1516 NMR (270 MHz; DMSO-d$_6$) δ (ppm): 13.50 (1H, brs), 7.58 (1H, d, J=16.3 Hz), 7.27 (1H, d; J=2.0 Hz), 7.13 (1H, dd, J=8.4, 2.0 Hz), 6.99 (1H, d, J=8.4 Hz), 6.96 (1H, d, J=16.3 Hz), 6.07–5.82 (2H, m), 5.20–5.01 (4H, m), 4.68–4.45(4H, m), 3.82 (3H, s), 3.79 (3H, s)

Reference Example 67

(E)-1,3-Diallyl-8-(3,4-dimethoxystyryl)-7-methylxanthine (Compound 70)

Substantially the same procedure as in Reference Example 1 was repeated using 2.30 g (5.84 mmol) of Compound 69 obtained in Reference Example 66 in place of Compound B. Then, the resultant crude crystals were recrystallized from ethanol to give 1.85 g (yield 78%) of Compound 70 as pale yellow flocculent precipitates.

Melting Point: 159.5°–160.0° C. Elemental Analysis: $C_{22}H_{24}N_4O_3$ Calcd. (%): C, 64.69; H, 5.92; N, 13.72 Found (%): C, 64.50; H, 6.03; N, 13.71 IR (KBr) $v_{max}$ (cm$^{-1}$): 1698, 1658, 1515, 1265 NMR (270 MHz; DMSO-d$_6$) δ (ppm): 7.60(1H, d, J=15.3 Hz), 7.42(1H, d, J=1.5 Hz), 7.29(1H, dd, J=8.4, 1.5 Hz), 7.21(1H, d, J=15.3 Hz), 6.99(1H, d, J=8.4Hz), 6.05–5.78 (2H, m), 5.20–5.01 (4H, m), 4.68–4.45 (4H, m), 4.03(3H, s), 3.84(3H, s), 3.80(3H, s)

Reference Example 68

(E)-8-(3,4-Dimethoxystyryl)-1,3-dipropyl-2-thioxanthine (Compound 71)

Substantially the same procedure as in Reference Example 1 was repeated using 4.00 g (16.5 mmol) of 5,6-diamino-1,3-dipropyl-2-thiouracil and 3.79 g (18.2 mmol) of 3,4-dimethoxycinnamic acid. Then, the resultant crude crystals were recrystallized from dioxane/water to give 3.16 g (yield 46%) of Compound 71 as yellow needles.

Melting Point: 273.2°–272.4° C. Elemental Analysis: $C_{21}H_{26}N_4O_3S$ Calcd. (%): C, 60.85; H, 6.32; N, 13.52 Found (%): C, 60.85; H, 6.49; N, 13.64 IR (KBr) $v_{max}$ (cm$^{-1}$): 1675, 1515 NMR (270 MHz; DMSO-d$_6$) δ (ppm): 7.64 (1H, d, J=16.5 Hz), 7.30(1H, s), 7.15(1H, d, J=8.2 Hz), 7.02 (1H, d, J=16.5 Hz), 6.99(1H, d, J=8.2 Hz), 4.56 (2H, t, J=7.6 Hz), 4.45 (2H, t, J=7.6 Hz), 3.83 (3H, s), 3.80 (3H, s), 1.85–1.60 (4H, m), 0.98–0.82 (6H, m)

Reference Example 69

(E)-8-(3,4-Dimethoxystyryl)-7-methyl-1,3-dipropyl-2-thioxanthine (Compound 72)

Substantially the same procedure as in Reference Example 1 was repeated using 3.00 g (7.25 mmol) of Compound 71 obtained in Reference Example 68 in place of Compound B. Then, the resultant crude crystals were recrystallized from toluene/ethanol to give 1.79 g (yield 58%) of Compound 72 as a pale yellow powder.

Melting Point: 137.3°–139.2° C. Elemental Analysis: $C_{22}H_{28}N_4O_3S$ Calcd. (%): C, 61.66; H, 6.59; N, 13.07 Found (%): C, 61.44; H, 6.71; N, 13.05 IR (KBr) $v_{max}$ (cm$^{-1}$): 1684, 1515, 1438 NMR (270 MHz; DMSO-d$_6$) δ (ppm): 7.67(1H, d, J=15.7 Hz), 7.44(1H, d, J=1.3 Hz), 7.33(1H, dd, J=8.3, 1.3 Hz), 7.24(1H, d, J=15.7 Hz), 7.00(1H, d, J=8.3 Hz), 4.56 (2H, t, J=7.6 Hz), 4.42(2H, t, J=7.6 Hz), 4.06(3H, s), 3.85(3H, s), 3.81(3H, s), 1.85–1.60(4H, m), 0.98–0.82 (6H, m)

Reference Example 70

(E)-8-(3,4-Dimethoxystyryl)-1,3-diethylxanthine (Compound 73)

3,4-Dimethoxycinnamic acid (1.39 g, 6.67 mmol) and 3-(3-diethylaminopropyl)-1-ethylcarbodiimide hydrochloride (1.74 g, 9.09 mmol) were added to a mixture of dioxane (40 ml) and water (20 ml) containing 5,6-diamino-1,3-diethyluracil [J. Am. Chem. Soc., 73, 114 (1953)] (1.20 g, 6.06 mmol). The resultant solution was stirred at room temperature for 2 hours at pH 5.5. After neutralization, the reaction solution was extracted three times with 50 ml of chloroform. The combined extract was washed with a saturated aqueous solution of sodium chloride and dried over anhydrous sodium sulfate, followed by evaporation under reduced pressure.

To the residue were added 10 ml of dioxane and 15 ml of an aqueous 1N sodium hydroxide solution, followed by heating under reflux for 20 minutes. After cooling, the solution was neutralized and 20 ml of chloroform was added thereto. The organic layer was separated and the aqueous layer was extracted twice with 20 ml of chloroform. The combined extract was washed with a saturated aqueous solution of sodium chloride and dried over anhydrous sodium sulfate, followed by evaporation under reduced pressure. The residue was purified by silica gel column chromatography (eluent: 2% methanol/chloroform), followed by recrystallization from toluene to give 1.06 g (yield 47%) of Compound 73 as pale yellow needles.

Melting Point: 268.8°–269.1° C. Elemental Analysis: $C_{19}H_{22}N_4O_4$ Calcd. (%): C, 61.61; H, 5.98; N, 15.12 Found (%): C, 61.99; H, 6.00; N, 14.91 IR (KBr) $v_{max}$ (cm$^{-1}$): 1694, 1641, 1514, 1492 NMR (270 MHz; DMSO-d$_6$) δ (ppm): 13.35(1H, brs), 7.59 (1H, d, J=16.2 Hz), 7.27(1H, d, J=1.4 Hz), 7.14(1H, dd, J=8.2, 1.4 Hz), 6.99(1H, d, J=8.2 Hz), 6.96(1H, d, J=16.2 Hz), 4.06(2H, q, J=7.0 Hz), 3.91(2H, q, J=7.0 Hz), 3.83(3H, s), 3.79(3H, s), 1.26(3H, t, J=7.0 Hz), 1.14 (3H, t, J=7.0 Hz)

Reference Example 71

(E)-8-(3,4-Dimethoxystyryl)-1,3-diethyl-7-methylxanthine (Compound 74)

Substantially the same procedure as in Reference Example 1 was repeated using 1.20 g (3.24 mmol) of Compound 73 obtained in Reference Example 70 in place of Compound B. Then, the resultant crude crystals were purified by silica gel column chromatography (eluent: 40% ethyl acetate/hexane), followed by recrystallization from 2-propanol to give 840 mg (yield 68%) of Compound 74 as pale yellow needles.

Melting Point: 190.4°–191.3° C. Elemental Analysis: $C_{20}H_{24}N_4O_4$ Calcd. (%): C, 62.48; H, 6.29; N, 14.57 Found (%): C, 62.52; H, 6.53; N, 14.56 IR (KBr) $v_{max}$ (cm$^{-1}$): 1697, 1655, 1518 NMR (270 MHz; CDCl$_3$) δ (ppm): 7.74(1H, d, J=15.5 Hz), 7.18 (1H, dd, J=8.3, 1.9 Hz), 7.08(1H, d, J=1.9 Hz), 6.89 (1H, d, J=8.3 Hz), 6.77 (1H, d, J=15.5 Hz), 4.21 (2H, q, J=6.9 Hz), 4.09(2H, q, J=6.9 Hz), 4.06 (3H, s), 3.96 (3H, s), 3.93 (3H, s), 1.39 (3H, t, J=6.9 Hz), 1.27(3H, t, J=6.9 Hz)

Reference Example 72

(E)-8-(2,3-Dimethoxystyryl)-1,3-diethylxanthine (Compound 75)

Substantially the same procedure as in Reference Example 70 was repeated using 2.0 g (10.1 mmol) of 5,6-diamino-1,3-diethyluracil and 2.52 g (12.1 mmol) of 2,3-dimethoxycinnamic acid. Then, the resultant crude crystals were recrystallized from dimethylsulfoxide/water to give 1.72 g (yield 46%) of Compound 75 as a white powder.

Melting Point: 287.5°–289.4° C. Elemental Analysis: $C_{19}H_{22}N_4O_4$ Calcd. (%): C, 61.61; H, 5.98; N, 15.12 Found (%): C, 61.56; H, 6.11; N, 14.83 IR (KBr) $v_{max}$ (cm$^{-1}$): 1697, 1656, 1500 NMR (270 MHz; DMSO-d$_6$) δ (ppm): 13.64(1H, brs), 7.84 (1H, d, J=16.8 Hz), 7.29(1H, dd, J=7.6, 1.7 Hz), 7.15–7.00 (3H, m), 4.07 (2H, q, J=7.0Hz), 3.94 (2H, q, J=7.0 Hz), 3.83 (3H, s), 3.79(3H, s), 1.26(3H, t, J=7.0 Hz), 1.14 (3H, t, J=7.0 Hz)

Reference Example 73

(E)-8-(2,3-Dimethoxystyryl)-1,3-diethyl-7-methylxanthine (Compound 76)

Substantially the same procedure as in Reference Example 1 was repeated using 1.60 g (4.32 mmol) of Compound 75 obtained in Reference Example 72 in place of Compound B. Then, the resultant crude crystals were recrystallized from cyclohexane/toluene to give 1.21 g (yield 73%) of Compound 76 as a pale yellow powder.

Melting Point: 194.9°–195.6° C. Elemental Analysis: $C_{20}H_{24}N_4O_4$ Calcd. (%): C, 62.48; H, 6.29; N, 14.57 Found (%): C, 62.67; H, 6.48; N, 14.31 IR (KBr) $v_{max}$ (cm$^{-1}$): 1694, 1660, 1272 NMR (270 MHz; CDCl$_3$) δ (ppm): 8.00(1H, d, J=16.8 Hz), 7.19(1H, dd, J=7.9, 1.3 Hz), 7.15–7.00(2H, m), 6.93 (1H, dd, J=7.9, 1.3 Hz), 4.26(2H, q, J=6.9 Hz), 4.09 (2H, q, J=6.9 Hz), 4.05(3H, s), 3.91(3H, s), 3.90 (3H, s), 1.39 (3H, t, J=6.9 Hz), 1.27 (3H, t, J=6.9 Hz)

Reference Example 74

(E)-8-(2,4-Dimethoxystyryl)-1,3-diethylxanthine (Compound 77)

Substantially the same procedure as in Reference Example 70 was repeated using 2.50 g (12.6 mmol) of 5,6-diamino-1,3-diethyluracil and 2.89 g (13.9 mmol) of 2,4-dimethoxycinnamic acid. Then, the resultant crude crystals were recrystallized from dimethylformamide/ethanol to give 0.92 g (yield 20%) of Compound 77 as yellow crystals.

Melting Point: 278.7°–279.8° C. Elemental Analysis: $C_{19}H_{22}N_4O_4$ Calcd. (%): C, 61.61; H, 5.98; N, 15.12 Found (%): C, 61.65; H, 5.95; N, 14.74 IR (KBr) $v_{max}$ (cm$^{-1}$): 1698, 1640, 1509, 1292 NMR (270 MHz; DMSO-d$_6$) δ (ppm): 13.43 (1H, brs), 7.77 (1H, d, J=16.8 Hz), 7.54 (1H, d, J=8.4 Hz), 6.95 (1H, d, J=16.8 Hz), 6.63 (1H, d, J=2.5 Hz), 6.60 (1H, dd, J=8.4, 2.5 Hz), 4.06(2H, q, J=6.9 Hz), 3.93 (2H, q, J=6.9 Hz), 3.89 (3H, s), 3.82 (3H, s), 1.25 (3H, t, J=6.9 Hz), 1.13 (3H, t, J=6.9 Hz)

Reference Example 75

(E)-8-(2,4-Dimethoxystyryl)-1,3-diethyl-7-methylxanthine (Compound 78)

Substantially the same procedure as in Reference Example 1 was repeated using 400 mg (1.08 mmol) of Compound 77 obtained in Reference Example 74 in place of Compound B. Then, the resultant crude crystals were recrystallized from hexane/ethyl acetate to give 335 mg (yield 81%) of Compound as yellow needles.

Melting Point: 195.9°–196.7° C. Elemental Analysis: $C_{20}H_{24}N_4O_4$ Calcd. (%): C, 62.48; H, 6.29; N, 14.57 Found (%): C, 62.29; H, 6.51; N, 14.66 IR (KBr) $v_{max}$ (cm$^{-1}$): 1693, 1654, 1603, 1294 NMR (270 MHz; CDCl$_3$) δ (ppm): 7.93(1H, d, J=15.8 Hz), 7.48(1H, d, J=8.3 Hz), 6.97(1H, d, J=15.8 Hz), 6.53 (1H, dd, J=8.3, 2.0 Hz), 6.49(1H, d, J=2.0 Hz), 4.22 (2H, q, J=6.9Hz), 4.08(2H, q, J=6.9Hz), 4.02(3H, s), 3.92(3H, s), 3.86(3H, s), 1.38(3H, t, J=6.9 Hz), 1.26 (3H, t, J=6.9 Hz)

Reference Example 76

(E)-1,3-Diethyl-8-(2,3,4-trimethoxystyryl)xanthine (Compound 79)

Substantially the same procedure as in Reference Example 70 was repeated using 2.5 g (12.6 mmol) of 5,6-diamino-1,3-diethyluracil and 2.3 g (13.9 mmol) of 2,3,4-trimethoxycinnamic acid. Then, the resultant crude crystals were recrystallized from dioxane/water to give 2.85 g (yield 57% of Compound 79 as white crystals.

Melting Point: 276.3°–277.0° C. Elemental Analysis: $C_{20}H_{24}N_4O_5$ Calcd. (%): C, 59.99; H, 6.04; N, 13.99 Found (%): C, 60.26; H, 6.24; N, 14.28 IR (KBr) $v_{max}$ (cm$^{-1}$): 1696, 1655, 1500 NMR (270 MHz; CDCl$_3$) δ (ppm): 12.3 9 (1H, brs), 7.88(1H, d, J=16.3 Hz), 7.30(1H, d, J=8.4 Hz), 7.09 (1H, d, J=16.3 Hz), 6.73 (1H, d, J=8.4 Hz), 4.26 (2H, q, J=6.9 Hz), 4.20 (2H, q, J=6.9 Hz), 3.96 (3H, s), 3.92 (3H, s), 3.91(3H, s), 1.41 (3H, t, J=6.9 Hz), 1.29 (3H, t, J=6.9 Hz)

Reference Example 77

(E)-1,3-Diethyl-7-methyl-8-(2,3,4-trimethoxystyryl)xanthine (Compound 80)

Substantially the same procedure as in Reference Example 1 was repeated using 1.5 g (3.75 mmol) of Compound 79 obtained in Reference Example 76 in place of Compound B. Then, the resultant crude crystals were recrystallized from hexane/ethyl acetate to give 1.32 g (yield 85%) of Compound as colorless needles.

Melting Point: 152.9°–154.3° C. Elemental Analysis: $C_{21}H_{26}N_4O_5$ Calcd. (%): C, 60.86; H, 6.32; N, 13.52 Found (%): C, 61.04; H, 6.44; N, 13.79 IR (KBr) $v_{max}$ (cm$^{-1}$): 1695, 1655, 1498, 1289 NMR (270 MHz; CDCl$_3$) δ (ppm): 7.88(1H, d, J=15.8 Hz), 7.28(1H, d, J=8.9 Hz), 7.01(1H, d, J=15.8Hz), 6.72 (1H, d, J=8.9 Hz), 4.22(2H, q, J=6.9 Hz), 4.09(2H, q, J=6.9 Hz), 4.04(3H, s), 3.97(3H, s), 3.91(3H, s), 3.90(3H, s), 1.38(3H, t, J=6.9 Hz), 1.27(3H, t, J=6.9 Hz)

Reference Example 78

(E)-1,3-Diethyl-8-(4-methoxy-2,3-dimethylstyryl)xanthine (Compound 81)

Substantially the same procedure as in Reference Example 70 was repeated using 2.5 g (12.6 mmol) of 5,6-diamino-1,3-diethyluracil and 2.9 g (13.9 mmol) of 4-methoxy-2,3-dimethylcinnamic acid. Then, the resultant crude crystals were recrystallized from ethanol/water to give 0.80 g (yield 17%) of Compound 81 as white crystals.

Melting Point: >280.0° C. Elemental Analysis: $C_{20}H_{24}N_4O_3$ Calcd. (%): C, 65.20; H, 6.56; N, 15.21 Found (%): C, 65.24; H, 6.61; N, 15.29 IR (KBr) $v_{max}$ (cm$^{-1}$): 1697, 1642, 1496, 1270 NMR (270 MHz; DMSO-d$_6$) δ (ppm): 13.52(1H, brs), 7.93 (1H, d, J=15.8 Hz), 7.56(1H, d, J=8.2 Hz), 6.89(1H, d, J=8.2 Hz), 6.82(1H, d, J=15.8 Hz), 4.06(2H, q, J=6.9 Hz), 3.94(2H, q, J=6.9 Hz), 3.81(3H, s), 2.33 (3H, s), 2.13 (3H, s), 1.26 (3H, t, J=6.9 Hz), 1.14 (3H, t, J=6.9 Hz)

Reference Example 79

(E)-1,3-Diethyl-8-(4-methoxy-2,3-dimethylstyryl)-7-methylxanthine (Compound 82)

Substantially the same procedure as in Reference Example 1 was repeated using 500 mg (1.36 mmol) of Compound 81 obtained in Reference Example 78 in place of Compound B. Then, the resultant crude crystals were recrystallized from hexane/ethyl acetate to give 493 mg (yield 95%) of Compound 82 as pale yellow needles.

Melting Point: 207.7°–208.3° C. Elemental Analysis: $C_{21}H_{26}N_4O_3$ Calcd. (%): C, 65.95; H, 6.85; N, 14.65 Found (%): C, 66.24; H, 6.99; N, 14.69 IR (KBr) $v_{max}$ (cm$^{-1}$): 1698, 1651, 1267 NMR (270 MHz; CDCl$_3$) δ (ppm): 8.08(1H, d, J=15.2 Hz), 7.46(1H, d, J=8.9 Hz), 6.77(1H, d, J=8.9 Hz), 6.67 (1H, d, J=15.2Hz), 4.22(2H, q, J=6.9 Hz), 4.09(2H, q, J=6.9 Hz), 4.03(3H, s), 3.86(3H, s), 2.40(3H, s), 2.21(3H, s), 1.39(3H, t, J=6.9 Hz), 1.26(3H, t, J=6.9 Hz)

Reference Example 80

(E)-1,3-Diethyl-8-(4-methoxy-2,5-dimethylstyryl)xanthine (Compound 83)

Substantially the same procedure as in Reference Example 70 was repeated using 2.5 g (12.6 mmol) of 5,6-diamino-1,3-diethyluracil and 2.9 g (13.9 mmol) of 4-methoxy-2,5-dimethylcinnamic acid. Then, the resultant crude crystals were recrystallized from dioxane/water to give 2.43 g (yield 52%) of Compound 83 as white crystals.

Melting Point: >280.0° C. Elemental Analysis: $C_{20}H_{24}N_4O_3$ Calcd. (%): C, 65.20; H, 6.56; N, 15.21 Found (%): C, 64.83; H, 6.56; N, 15.43 IR (KBr) $v_{max}$ (cm$^{-1}$): 1690, 1646, 1510, 1265 NMR 270 MHz; DMSO-d$_6$) δ (ppm): 13.52(1H, brs), 7.82 (1H, d, J=16.3 Hz), 7.54(1H, s), 6.86(1H, d, J=16.3 Hz), 6.82 (1H, s), 4.06 (2H, q, J=6.9 Hz), 3.94 (2H, q, J=6.9 Hz), 3.81(3H, s), 2.41(3H, s), 2.14 (3H, s), 1.25 (3H, t, J=6.9 Hz), 1.14 (3H, t, J=6.9 Hz)

Reference Example 81

(E)-1,3-Diethyl-8-(4-methoxy-2,5-dimethylstyryl)-7-methylxanthine (Compound 84)

Substantially the same procedure as in Reference Example 1 was repeated using 1.10 g (2.98 mmol) of Compound 83 obtained in Reference Example 80 in place of Compound B. Then, the resultant crude crystals were recrystallized from ethyl acetate to give 0.76 g (yield 67%) of Compound 84 as yellow needles.

Melting Point: 235.4°–236.1° C. Elemental Analysis: $C_{21}H_{26}N_4O_3$ Calcd. (%): C, 65.95; H, 6.85; N, 14.65 Found (%): C, 65.56; H, 6.93; N, 14.64 IR (KBr) $v_{max}$ (cm$^{-1}$): 1689, 1657, 1510, 1263 NMR (270 MHz; CDCl$_3$) δ (ppm): 7.97(1H, d, J=15.5 Hz), 7.42(1H, s), 6.71(1H, d, J=15.5 Hz), 6.66(1H, s), 4.22(2H, q, J=6.9 Hz), 4.09(2H, q, J=6.9 Hz), 4.05 (3H, s), 3.86(3H, s), 2.48(3H, s), 2.23(3H, s), 1.38 (3H, t, J=6.9 Hz), 1.26 (3H, t, J=6.9 Hz)

Reference Example 82

(E)-8-(2,4-Dimethoxy-3-methylstyryl)-1,3-diethylxanthine (Compound 85)

Substantially the same procedure as in Reference Example 70 was repeated using 2.0 g (10.1 mmol) of 5,6-diamino-1,3-diethyluracil and 2.04 g (9.19 mmol) of 2,4-dimethoxy-3-methylcinnamic acid. Then, the resultant crude crystals were recrystallized from dioxane/water to give 1.22 g (yield 32%) of Compound 85 as a yellow powder.

Melting Point: >275.0° C. Elemental Analysis: $C_{20}H_{24}N_4O_4$ Calcd. (%): C, 62.48; H, 6.29; N, 14.57 Found (%): C, 62.28; H, 6.42; N, 14.22 IR (KBr) $v_{max}$ (cm$^{-1}$): 1696, 1635, 1592, 1499 NMR (270 MHz; DMSO-d$_6$) δ (ppm): 7.75(1H, d, J=16.5 Hz), 7.58(1H, d, J=8.8 Hz), 6.99(1H, d, J=16.5 Hz), 6.85 (1H, d, J=8.8 Hz), 4.04(2H, q, J=6.9 Hz), 3.95(2H, q, J=6.9 Hz), 3.83(3H, s), 3.70(3H, s), 2.09(3H, s), 1.26 (3H, t, J=6.9 Hz), 1.14 (3H, t, J=6.9 Hz)

Reference Example 83

(E)-8-(2,4-Dimethoxy-3-methylstyryl)-1,3-diethyl-7-methylxanthine (Compound 86)

Substantially the same procedure as in Reference Example 1 was repeated using 700 mg (1.82 mmol) of Compound obtained in Reference Example 82 in place of Compound B. Then, the resultant crude crystals were recrystallized from cyclohexane/toluene to give 610 mg (yield 84%) of Compound as pale yellow needles.

Melting Point: 196.1°–196.8° C. Elemental Analysis: $C_{21}H_{26}N_4O_4$ Calcd. (%): C, 63.30; H, 6.57; N, 14.06 Found (%): C, 63.32; H, 6.74; N, 14.13 IR (KBr) $\nu_{max}$ (cm$^{-1}$): 1695, 1649, 1498 NMR (270 MHz; CDCl$_3$) δ (ppm): 7.81(1H, d, J=15.8 Hz), 7.78(1H, d, J=8.6 Hz), 7.23(1H, d, J=15.8 Hz), 6.87 (1H, d, J=8.6 Hz), 4.07(2H, q, J=6.9 Hz), 4.01(3H, s), 3.92(2H, q, J=6.9 Hz), 3.85(3H, s), 3.70(3H, s), 2.10(3H, s), 1.27(3H, t, J=6.9 Hz), 1.13(3H, t, J=6.9 Hz)

Reference Example 84

(E)-1,3-Diethyl-8-(3,4-methylenedioxystyryl)xanthine (Compound 87)

Substantially the same procedure as in Reference Example 70 was repeated using 2.0 g (10.1 mmol) of 5,6-diamino-1,3-diethyluracil and 2.33 g (12.1 mmol) of 3,4-methylenedioxycinnamic acid. Then, the resultant crude crystals were recrystallized from dimethylformamide/water to give 1.34 g (yield 38%) of Compound 87 as a yellowish green powder.

Melting Point: >275.0° C. Elemental Analysis: $C_{18}H_{18}N_4O_4$ Calcd. (%): C, 61.01; H, 5.11; N, 15.81 Found (%): C, 61.16; H, 5.03; N, 15.80 IR (KBr) $\nu_{max}$ (cm$^{-1}$): 1685, 1638, 1499 NMR (270 MHz; DMSO-d$_6$) δ (ppm): 7.55(1H, d, J=16.3 Hz), 7.30(1H, s), 7.08(1H, d, J=8.9 Hz), 6.96(1H, d, J=8.9 Hz), 6.90(1H, d, J=16.3 Hz), 6.07(2H, s), 4.05 (2H, q, J=6.9 Hz), 3.93(2H, q, J=6.9 Hz), 1.25(3H, t, J=6.9 Hz), 1.10 (3H, t, J=6.9 Hz)

Reference Example 85

(E)-1,3-Diethyl-7-methyl-8-(3,4-methylenedioxystyryl)xanthine (Compound 88)

Substantially the same procedure as in Reference Example 1 was repeated using 1.35 g (3.81 mmol) of Compound 87 obtained in Reference Example 84 in place of Compound B. Then, the resultant crude crystals were recrystallized from cyclohexane/toluene to give 940 mg (yield 67%) of Compound as yellow needles.

Melting Point: 219.4°–219.6° C. Elemental Analysis: $C_{19}H_{20}N_4O_4$ Calcd. (%): C, 61.94; H, 5.47; N, 15.20 Found (%): C, 62.09; H, 5.41; N, 15.16 IR (KBr) $\nu_{max}$ (cm$^{-1}$): 1687, 1657, 1569, 1498, 1443 NMR (270 MHz; CDCl$_3$) δ (ppm): 7.70(1H, d, J=15.5 Hz), 7.10 (1H, d, J=1.6 Hz), 7.06(1H, dd, J=8.0, 1.6 Hz), 6.84 (1H, d, J=8.0 Hz), 6.73(1H, d, J=15.5 Hz), 6.02 (2H, s), 4.21 (2H, q, J=6.9 Hz), 4.09 (2H, q, J=6.9 Hz), 4.04(3H, s), 1.38(3H, t, J=6.9 Hz), 1.26 (3H, t, J=6.9 Hz)

Reference Example 86

(E)-8-[2-(1,4-Benzodioxan-6-yl)vinyl]-1,3-diethylxanthine (Compound 89)

Substantially the same procedure as in Reference Example 70 was repeated using 2.85 g (14.4 mmol) of 5,6-diamino-1,3-diethyluracil and 2.70 g (13.1 mmol) of 3-(1,4-benzodioxan-6-yl)acrylic acid. Then, the resultant crude crystals were recrystallized from dioxane/water to give 2.45 g (yield 51%) of Compound 89 as a pale yellow powder.

Melting Point: >300° C. Elemental Analysis: $C_{19}H_{20}N_4O_4$ Calcd. (%): C, 61.94; H, 5.47; N, 15.20 Found (%): C, 61.97; H, 5.62; N, 15.07 IR (KBr) $\nu_{max}$ (cm$^{-1}$): 1682, 1637, 1511, 1310 NMR (270 MHz; DMSO-d$_6$) δ (ppm): 7.51(1H, d, J=16.2 Hz), 7.10–7.03(2H, m), 6.89(1H, d, J=7.9 Hz), 6.87(1H, d, J=16.2 Hz), 4.27 (4H, s), 4.05 (2H, q, J=6.9 Hz), 3.93(2H, q, J=6.9 Hz), 1.22(3H, t, J=6.9 Hz), 1.13 (3H, t, J=6.9 Hz)

Reference Example 8.7

(E)-8-[2-(1,4-Benzodioxan-6-yl)vinyl]-1,3-diethyl-7-methylxanthine (Compound 90)

Substantially the same procedure as in Reference Example 1 was repeated using 2.00 g (5.43 mmol) of Compound 89 obtained in Reference Example 86 in place of Compound B. Then, the resultant crude crystals were recrystallized from ethanol/2-propanol to give 1.58 g (yield 76%) of Compound 90 as yellow needles.

Melting Point: 233.1°–233.6° C. Elemental Analysis: $C_{20}H_{22}N_4O_4$ Calcd. (%): C, 62.81; H, 5.79; N, 14.65 Found (%): C, 62.55; H, 5.80; N, 14.60 IR (KBr) $\nu_{max}$ (cm$^{-1}$): 1689, 1654, 1509 NMR (270 MHz; CDCl$_3$) δ (ppm): 7.67(1H, d, J=15.8 Hz), 7.15–7.05(2H, m), 6.88(1H, d, J=8.3 Hz), 6.75(1H, d, J=15.8 Hz), 4.30 (4H, s), 4.21 (2H, q, J=6.9 Hz), 4.08(2H, q, J=6.9 Hz), 4.03(3H, s), 1.39(3H, t, J=6.9 Hz), 1.35 (3H, t, J=6.9 Hz)

Reference Example 88

(E)-8-(2,3,4-Trimethoxystyryl)theophylline (Compound 91)

Substantially the same procedure as in Reference Example 70 was repeated using 5.00 g (29.4 mmol) of 5,6-diamino-1,3-dimethyluracil and 7.71 g (32.4 mmol) of 2,3,4-trimethoxycinnamic acid. Then, the resultant crude crystals were recrystallized from 2-propanol/water to give 3.78 g (yield 35%) of Compound 91 as an ocher powder.

Melting Point: 264.8°–266.1° C. Elemental Analysis: $C_{18}H_{20}N_4O_5$ Calcd. (%): C, 58.05; H, 5.41; N, 15.04 Found (%): C, 58.28; H, 5.38; N, 15.20 IR (KBr) $\nu_{max}$ (cm$^{-1}$): 1697, 1651, 1505, 1297 NMR (270 MHz; CDCl$_3$) δ (ppm): 12.78(1H, s), 7.91(1H, d, J=16.8 Hz), 7.28 (1H, d, J=9.4 Hz), 7.13 (1H, d, J=16.8 Hz), 6.73 (1H, d, J=9.4 Hz), 3.95 (3H, s), 3.92 (3H, s), 3.90 (3H, s), 3.69 (3H, s), 3.54 (3H, s)

Reference Example 89

(E)-8-(2,3,4-Trimethoxystyryl)caffeine (Compound 92)

Substantially the same procedure as in Reference Example 1 was repeated using 2.00 g (5.38 mmol) of Compound 91 obtained in Reference Example 88 in place of Compound B. Then, the resultant crude crystals were recrystallized from cyclohexane/toluene to give 1.68 g (yield 81%) of Compound as a pale yellow powder.

Melting Point: 186.7°–187.9° C. Elemental Analysis: $C_{19}H_{22}N_4O_5$ Calcd. (%): C, 59.06; H, 5.74; N, 14.50 Found (%): C, 59.27; H, 5.72; N, 14.60 IR (KBr) $\nu_{max}$ (cm$^{-1}$): 1694, 1655, 1596, 1544, 1501, 1295 NMR (270 MHz; CDCl$_3$) δ (ppm): 7.90(1H, d, J=16.3 Hz), 7.28(1H, d, J=7.9 Hz), 7.01(1H, d, J=16.3 Hz), 6.72 (1H, d, J=7.9 Hz), 4.04(3H, s), 3.97(3H, s), 3.91 (3H, s), 3.90(3H, s), 3.64(3H, s), 3.42(3H, s)

Reference Example 90

(E)-8-(4-Methoxy-2,3-dimethylstyryl)theophylline (Compound 93)

Substantially the same procedure as in Reference Example 70 was repeated using 1.74 g (10.2 mmol) of 5,6-diamino-1,3-dimethyluracil and 2.42 g (11.8 mmol) of 4-methoxy-2,3-dimethylcinnamic acid. Then, the resultant crude crystals were recrystallized from acetonitrile to give 750 mg (yield 22%) of Compound 93 as a white powder.

Melting Point: >275° C. Elemental Analysis: $C_{18}H_{20}N_4O_3$ Calcd. (%): C, 63.51; H, 5.92; N, 16.46 Found (%): C, 63.56; H, 5.82; N, 16.30 IR (KBr) $v_{max}$ (cm$^{-1}$): 1703, 1634, 1593 NMR (270 MHz; DMSO-d$_6$) δ (ppm): 13.45 (1H, s), 7.93 (1H, d, J=16.2 Hz), 7.53(1H, d, J=8.9 Hz), 6.88(1H, d, J=8.9 Hz), 6.79(1H, d, J=16.2 Hz), 3.80(3H, s), 3.75 (3H, s), 3.25(3H, s), 2.32(3H, s), 2.12(3H, s)

Reference Example 91

(E)-8-(4-Methoxy-2,3-dimethylstyryl)caffeine (Compound 94)

Substantially the same procedure as in Reference Example 1 was repeated using 500 mg (1.47 mmol) of Compound 93 obtained in Reference Example 90 in place of Compound B. Then, the resultant crude crystals were recrystallized from toluene to give 280 mg (yield 54%) of Compound 94 as a pale yellow powder.

Melting Point: >275° C. Elemental Analysis: $C_{19}H_{22}N_4O_3$ Calcd. (%): C, 64.39; H, 6.25; N, 15.80 Found (%): C, 64.44; H, 6.27; N, 16.11 IR (KBr) $v_{max}$ (cm$^{-1}$): 1694, 1650, 1544, 1491, 1435 NMR (270 MHz; CDCl$_3$) δ (ppm): 7.96(1H, d, J=15.5 Hz), 7.73(1H, d, J=8.6 Hz), 7.07(1H, d, J=15.5 Hz), 6.90 (1H, d, J=8.6 Hz), 4.02(3H, s), 3.82(3H, s), 3.48 (3H, s), 3.29(3H, s), 2.32(3H, s), 2.13(3H, s)

Reference Example 92

(E)-8-(3,4-Methylenedioxystyryl)theophylline (Compound 95)

Substantially the same procedure as in Reference Example 70 was repeated using 5.0 g (29.4 retool) of 5,6-diamino-1,3-dimethyluracil and 6.78 g (35.3 mmol) of 3,4-methylenedioxycinnamic acid. Then, the resultant crude crystals were recrystallized from dimethylformamide/water to give 1.20 g (yield 13%) of Compound 95 as a pale yellow powder.

Melting Point: >275 ° C Elemental Analysis: $C_{16}H_{14}N_4O_4$ Calcd. (%): C, 58.99; H, 4.32; N, 17.16 Found (%): C, 58.84; H, 4.30; N, 16.97 IR (KBr) $v_{max}$ (cm$^{-1}$): 1692, 1642, 1499 NMR (270 MHz; DMSO-d$_6$) δ (ppm): 7.57(1H, d, J=16.1 Hz), 7.09(1H, s), 7.07(1H, d, J=7.9 Hz), 6.92(1H, d, J=7.9 Hz), 6.88(1H, d, J=16.1 Hz), 6.07(2H, s), 3.47 (3H, s), 3.30(3H, s)

Reference Example 93

(E)-8-(3,4-Methylenedioxystyryl)caffeine (Compound 96)

Substantially the same procedure as in Reference Example 1 was repeated using 2.32 g (7.13 mmol) of Compound 95 obtained in Reference Example 92 in place of Compound B. Then, the resultant crude crystals were recrystallized from dioxane to give 1.54 g (yield 64%) of Compound 96 as yellow needles.

Melting Point: >300° C. Elemental Analysis: $C_{17}H_{16}N_4O_4$ Calcd. (%): C, 59.99; H, 4.73; N, 16.46 Found (%): C, 59.98; H, 4.66; N, 16.38 IR (KBr) $v_{max}$ (cm$^{-1}$): 1702, 1663, 1545, 1506 NMR (270 MHz; CDCl$_3$) δ (ppm): 7.72(1H, d, J=15.3 Hz), 7.10(1H, d, J=1.5 Hz), 7.06(1H, dd, J=7.9, 1.5 Hz), 6.84(1H, d, J=7.9 Hz), 6.73(1H, d, J=15.3 Hz), 6.03 (2H, s), 4.05(3H, s), 3.63(3H, s), 3.42(3H, s)

Reference Example 94

(E)-8-(2,3-Dimethoxystyryl)theophylline (Compound 97)

Substantially the same procedure as in Reference Example 70 was repeated using 2.50 g (14.7 mmol) of 5,6-diamino-1,3-dimethyluracil and 3.37 g (16.2 mmol) of 2,3-dimethoxycinnamic acid. Then, the resultant crude crystals were recrystallized from ethanol/water to give 1.03 g (yield of Compound 97 as pale yellow needles.

Melting Point: 289.2°–290.5° C. Elemental Analysis: $C_{17}H_{18}N_4O_4$ Calcd. (%): C, 59.64; H, 5.29; N, 16.36 Found (%): C, 59.42; H, 5.12; N, 16.65 IR (KBr) $v_{max}$ (cm$^{-1}$): 1700, 1649, 1499, 1476, 1273 NMR(270 MHz; DMSO-d$_6$) δ (ppm): 13.60 (1H, brs), 7.84 (1H, d, J=16.8 Hz), 7.26(1H, d, J=6.9 Hz), 7.15–7.00 (3H, m), 3.83(3H, s), 3.79(3H, s), 3.48(3H, s), 3.26 (3H, s)

Reference Example 95

(E)-8-(2,3-Dimethoxystyryl)caffeine (Compound 98)

Substantially the same procedure as in Reference Example 1 was repeated using 1.10 g (3.22 mmol) of Compound 97 obtained in Reference Example 94 in place of Compound B. Then, the resultant crude crystals were recrystallized from toluene to give 570 mg (yield 50%) of Compound 98 as yellow needles.

Melting Point: 233.6°–236.7° C. Elemental Analysis: $C_{18}H_{20}N_4O_4$ Calcd. (%): C, 60.66; H, 5.65; N, 15.72 Found (%): C, 60.21; H, 5.74; N, 16.13 IR (KBr) $v_{max}$ (cm$^{-1}$): 1688, 1645, 1545, 1480 NMR (270 MHz; DMSO-d$_6$) δ (ppm): 7.91 (1H, d, J=16.0 Hz), 7.52 (1H, dd, J=7.6, 1.7 Hz), 7.32(1H, d, J=16.0 Hz), 7.10–7.05 (2H, m), 4.03 (3H, s), 3.84 (3H, S), 3.79 (3H, s), 3.48 (3H, s), 3.24(3H, s)

Reference Example 96

(E)-8-(2,4-Dimethoxystyryl)theophylline (Compound 99)

Substantially the same procedure as in Reference Example 70 was repeated using 1.0 g (5.88 mmol) of 5,6-diamino-1,3-dimethyluracil and 1.35 g (6.48 mmol) of 2,4-dimethoxycinnamic acid. Then, the resultant crude crystals were recrystallized from dimethylformamide to give 221 mg (yield 11%) of Compound 99 as pale yellow grains.

Melting Point: >280° C. Elemental Analysis: $C_{17}H_{18}N_4O_4$ Calcd. (%): C, 59.64; H, 5.29; N, 16.36 Found (%): C, 59.51; H, 5.34; N, 16.58 IR (KBr) $v_{max}$ (cm$^{-1}$): 1705, 1650, 1607, 1505 NMR (270 MHz; DMSO-d$_6$) δ (ppm): 13.40(1H, brs), 7.78 (1H, d, J=16.5 Hz), 7.53 (1H, d, J=8.3 Hz), 6.93 (1H, d, J=16.5 Hz), 6.63(1H, d, J=2.3 Hz), 6.60(1H, dd, J=8.3, 2.3 Hz), 3.89(3H, s), 3.82(3H, s), 3.47(3H, s), 3.25 (3H, s)

Reference Example 97

(E)-8-(2,4-Dimethoxystyryl)caffeine (Compound 100)

Substantially the same procedure as in Reference Example 1 was repeated using 700 mg (2.05 mmol) of Compound 99 obtained in Reference Example 96 in place of Compound B. Then, the resultant crude crystals were recrystallized from dioxane to give 621 mg (yield 85%) of Compound 100 as yellow needles.

Melting Point: 241.5°–242.1° C. Elemental Analysis: $C_{18}H_{20}N_4O_4$ Calcd. (%): C, 60.66; H, 5.65; N, 15.72 Found (%): C, 60.49; H, 5.61; N, 15.69 IR (KBr) $v_{max}$ (cm$^{-1}$): 1685, 1650, 1602, 1434 NMR (270 MHz; CDCl$_3$) δ (ppm): 7.95 (1H, d, J=15.8 Hz), 7.48 (1H, d, J=8.6 Hz), 6.98(1H, d, J=15.8 Hz), 6.54 (1H, dd, J=8.6, 2.3 Hz), 6.49(1H, d, J=2.3 Hz), 4.03 (3H, s), 3.92(3H, s), 3.86(3H, s), 3.64(3H, s), 3.42 (3H, s)

Reference Example 98

(E)-8-(4-Methoxy-2,5-dimethylstyryl)theophylline (Compound 101)

Substantially the same procedure as in Reference Example 70 was repeated using 1.0 g (5.88 mmol) of 5,6-diamino-1,3-dimethyluracil and 1.33 g (6.45 mmol) of 4-methoxy-2,5-dimethylcinnamic acid. Then, the resultant crude crystals were recrystallized from dimethylformamide to give 393 mg (yield 20%) of Compound 101 as pale yellow grains.

Melting Point: >280° C. Elemental Analysis: $C_{18}H_{20}N_4O_3$ Calcd. (%): C, 63.51; H, 5.92; N, 16.46 Found (%): C, 63.59; H, 6.10; N, 16.23 IR (KBr) $v_{max}$ (cm$^{-1}$): 1703, 1648, 1509, 1260 NMR (270 MHz; DMSO-d$_6$) δ (ppm): 13.48(1H, brs), 7.81 (1H, d, J=16.2 Hz), 7.50(1H, s), 6.82(1H, d, J=16.2 Hz), 6.81(1H, s), 3.81(3H, s), 3.46(3H, s), 3.25(3H, s), 2.40(3H, s), 2.14(3H, s)

Reference Example 99

(E)-8-(4-Methoxy-2,5-dimethylstyryl)caffeine (Compound 102)

Substantially the same procedure as in Reference Example 1 was repeated using 300 mg (0.88 mmol) of Compound 101 obtained in Reference Example 98 in place of Compound B. Then, the resultant crude crystals were recrystallized from dioxane to give 211 mg (yield. 68%) of Compound 102 as yellow needles.

Melting Point: >280° C. MS-EI m/e: 354 (M$^+$), 339 (M$^+$—CH$_3$) IR (KBr) $v_{max}$ (cm$^{-1}$): 1692, 1653, 1508 NMR (270 MHz; CDCl$_3$) δ (ppm): 8.00(1H, d, J=15.3 Hz), 7.42(1H, s), 6.72(1H, d, J=15.3 Hz), 6.66(1H, s), 4.06 (3H, s), 3.86 (3H, s), 3.64 (3H, s), 3.42 (3H, s), 2.49(3H, s), 2.23(3H, s)

Reference Example 100

(E)-8-(2,4-Dimethoxy-3-methylstyryl)theophylline (Compound 103)

Substantially the same procedure as in Reference Example 70 was repeated using 1.0 g (5.88 mmol) of 5,6-diamino-1,3-dimethyluracil and 1.44 g (6.45 mmol) of 2,4-dimethoxy-3-methylcinnamic acid. Then, the resultant crude crystals were recrystallized from dioxane to give 581 mg (yield 28%) of Compound 103 as pale yellow needles.

Melting Point: >280° C. Elemental Analysis: $C_{18}H_{20}N_4O_4$ Calcd. (%): C, 60.67; H, 5.65; N, 15.72 Found (%): C, 60.34; H, 5.77; N, 15.64 IR (KBr) $v_{max}$ (cm$^{-1}$): 1695, 1653, 1499, 1270 NMR (270 MHz; DMSO-d$_6$) δ (ppm): 13.52(1H, brs), 7.75 (1H, d, J=16.2 Hz), 7.55(1H, d, J=8.3 Hz), 6.96(1H, d, J=16.2 Hz), 6.84(1H, d, J=8.3 Hz), 3.83(3H, s), 3.70(3H, s), 3.47(3H, s), 3.25(3H, s), 2.09(3H, s)

Reference Example 101

(E)-8-(2,4-Dimethoxy-3-methylstyryl)caffeine (Compound 104)

Substantially the same procedure as in Reference Example 1 was repeated using 300 mg (0.84 mmol) of Compound 103 obtained in Reference Example 100 in place of Compound B. Then, the resultant crude crystals were recrystallized from methylene chloride/ether to give 239 mg (yield 77%) of Compound 104 as white needles.

Melting Point: 252.7°–253.5° C. Elemental Analysis: $C_{19}H_{22}N_4O_4$ Calcd. (%): C, 61.61; H, 5.98; N, 15.13 Found (%): C, 61.40; H, 6.06; N, 15.17 IR (KBr) $v_{max}$ (cm$^{-1}$): 1692, 1651, 1505 NMR (270 MHz; CDCl$_3$) δ (ppm): 7.92(1H, d, J=15.8 Hz), 7.42 (1H, d, J=8.9 Hz), 6.99(1H, d, J=15.8 Hz), 6.70 (1H, d, J=8.9 Hz), 4.04(3H, s), 3.88(3H, s), 3.78 (3H, s), 3 64 (3H, s), 3.42(3H, s), 2.19(3H, s)

Reference Example 102

(E)-8-(2-Chloro-3,4-dimethoxystyryl)-1,3-diethylxanthine (Compound 105)

Substantially the same procedure as in Reference Example 70 was repeated using 2.00 g (10.1 mmol) of 5,6-diamino-1,3-diethyluracil and 2.94 g (12.1 mmol) of 2-chloro-3,4-dimethoxycinnamic acid. Then, the resultant crude crystals were recrystallized from 2-propanol/water to give 2.19 g (yield 54%) of Compound 105 as pale yellow needles.

Melting Point: 278.0°–280.9° C. Elemental Analysis: $C_{19}H_{21}ClN_4O_4$ Calcd. (%): C, 56.36; H, 5.22; N, 13.83 Found (%): C, 56.13; H, 5.21; N, 13.67 IR (KBr) $v_{max}$ (cm$^{-1}$): 1705, 1642, 1499 NMR (270 MHz; DMSO-d$_6$) δ (ppm): 7.88(1H, d, J=16.3 Hz), 7.64 (1H, d, J=8.9 Hz), 7.13(1H, d, J=8.9 Hz), 7.00 (1H, d, J=16.3 Hz), 4.06(2H, q, J=7.1 Hz), 3.98–3.88 (2H, m), 3.88(3H, s), 3.77(3H, s), 1.26(3H, t, J=7.1 Hz), 1.14 (3H, t, J=6.9 Hz)

Reference Example 103

(E)-8-(2-Chloro-3,4-dimethoxystyryl)-1,3-diethyl-7-methylxanthine (Compound 106)

Substantially the same procedure as in Reference Example 1 was repeated using 1.80 g (4.45 mmol) of Compound 105 obtained in Reference Example 102 in place of Compound B. Then, the resultant crude crystals were recrystallized from 2-propanol/water to give 1.20 g (yield 64%) of Compound 106 as yellow needles.

Melting Point: 204.6°–205.4° C. Elemental Analysis: $C_{20}H_{23}ClN_4O_4$ Calcd. (%): C, 57.34; H, 5.53; N, 13.37 Found (%): C, 57.46; H, 5.67; N, 13.10 IR (KBr) $v_{max}$ (cm$^{-1}$): 1696, 1657, 1496, 1439, 1292 NMR (270 MHz; DMSO-d$_6$) δ (ppm): 7.92(1H, d, J=15.8 Hz), 7.86(1H, d, J=8.9 Hz), 7.29(1H, d, J=15.8 Hz), 7.16 (1H, d, J=8.9 Hz), 4.11–4.03(2H, m), 4.03(3H, s), 3.96–3.90(2H, m), 3.90(3H, s), 3.77(3H, s), 1.26 (3H, t, J=6.9 Hz), 1.13(3H, t, J=6.9 Hz)

Reference Example 104

(E)-8-(2-Chloro-3,4-dimethoxystyryl)theophylline (Compound 107)

2-Chloro-3,4-dimethoxycinnamic acid (3.93 g, 16.2 mmol) was dissolved in 57 ml of pyridine. To the solution was added 1.26 ml (17.6 mmol) of thionyl chloride under ice cooling, and the mixture was stirred at 60° C. for 1.5 hours. Methylene chloride (58 ml) containing 2.50 g (14.7 mmol) of 5,6-diamino-1,3-dimethyluracil was added dropwise to the solution under ice cooling, and the reaction solution was stirred at room temperature for further 40 minutes. The deposited crystals were collected by filtration and the obtained crude crystals were dissolved in a mixture of 68 ml of an aqueous 2N sodium hydroxide solution, 68 ml of dioxane, and 34 ml of water, followed by heating under reflux for 30 minutes. After cooling, the solution was neutralized with a concentrated aqueous solution of hydrochloric acid, and the deposited crystals were collected by filtration. The collected crystals were washed with water, dried, and recrystallized from dimethylformamide/water to give 1.55 g (yield 30%) of Compound 107 as pale yellow needles.

Melting Point: 241.6°–24.2.6 ° C. Elemental Analysis: $C_{17}H_{17}ClN_4O_4$ Calcd. (%): C, 54.18; H, 4.54; N, 14.86 Found (%): C, 54.31; H, 4.54; N, 14.43 IR (KBr) $v_{max}$ (cm$^{-1}$): 1704, 1653, 1496, 1300 NMR (270 MHz; DMSO-d$_6$) δ (ppm): 7.88(1H, d, J=16.2 Hz), 7.62 (1H, d, J=8.9 Hz), 7.13 (1H, d, J=8.9 Hz), 6.97 (1H, d, J=16.2 Hz), 3.88(3H, s), 3.77(3H, s), 3.47 (3H, s), 3.25(3H, s)

Reference Example 105

(E)-8-(2-Chloro-3,4-dimethoxystyryl)caffeine (Compound 108)

Substantially the same procedure as in Reference Example 1 was repeated using 1.0 g (2.66 mmol) of Compound obtained in Reference Example 104 in place of Compound B. Then, the resultant crude crystals were recrystallized from toluene to give 840 mg (yield 81%) of Compound 108 as a yellow powder.

Melting Point: 284.6°–288.0° C. Elemental Analysis: $C_{18}H_{19}ClN_4O_4$ Calcd. (%): C, 55.31; H, 4.59; N, 14.33 Found (%): C, 55.40; H, 4.83; N, 14.09 IR (KBr) $v_{max}$ (cm$^{-1}$): 1688, 1650, 1493, 1290 NMR (270 MHz; CDCl$_3$) δ (ppm): 8.10(1H, d, J=15.8 Hz), 7.43 (1H, d, J=8.8 Hz), 6.88 (1H, d, J=8.8 Hz), 6.83 (1H, d, J=15.8 Hz), 4.06(3H, s), 3.93(3H, s), 3.90 (3H, s), 3.64(3H, s), 3.42(3H, s)

Reference Example 106

(E)-8-(2,5-Dimethylstyryl)-1,3-diethylxanthine (Compound 109)

Substantially the same procedure as in Reference Example 70 was repeated using 3.00 g (15.1 mmol) of 5,6-diamino-1,3-diethyluracil and 3.20 g (18.2 mmol) of 2,5-dimethylcinnamic acid. Then, the resultant crude crystals were recrystallized from ethanol/toluene to give 2.56 g (yield 50%) of Compound 109 as white needles.

Melting Point: 281.8°–282.5° C. Elemental Analysis: $C_{19}H_{22}N_4O_2 \cdot 0.5H_2O$ Calcd. (%): C, 66.46; H, 6.97; N, 15.50 Found (%): C, 66.77; H, 6.82; N, 15.72 IR (KBr) $v_{max}$ (cm$^{-1}$): 1706, 1639, 1503 NMR (270 MHz; DMSO-d$_6$) δ (ppm): 7.84(1H, d, J=16.3 Hz), 7.53(1H, s), 7.13(1H, d,, J=7.4 Hz), 7.06(1H, d, J=7.4 Hz), 7.00(1H, d, J=16.3 Hz), 4.06(2H, q, J=7.1 Hz), 3.94 (2H, q, J=7.1 Hz), 2.37 (3H, s), 2.30 (3H, s), 1.26(3H, t, J=7.1 Hz), 1.14 (3H, t, J=7.1 Hz)

Reference Example 107

(E)-8-(2,5-Dimethylstyryl)-1,3-diethyl-7-methylxanthine (Compound 110)

Substantially the same procedure as in Reference Example 1 was repeated using 2.00 g (5.92 mmol) of Compound 109 obtained in Reference Example 106 in place of Compound B. Then, the resultant crude crystals were recrystallized from toluene/cyclohexane to give 1.29 g (yield 62%) of Compound 110 as white needles.

Melting Point: 190.3°–190.7° C. Elemental Analysis: $C_{20}H_{24}N_4O_2$ Calcd. (%): C, 68.16; H, 6.86; N, 15.89 Found (%): C, 68.15; H, 7.02; N, 15.65 IR (KBr) $v_{max}$ (cm$^{-1}$): 1698, 1657 NMR (270 MHz; CDCl$_3$) δ (ppm): 7.86(1H, d, J=15.8 Hz), 7.71(1H, s), 7.23(1H, d, J=15.8 Hz), 7.15(1H, d, J=7.9 Hz), 7.09 (1H, d, J=7.9 Hz), 4.11–4.04 (2H, m), 4.04 (3H, s), 3.92(2H, q, J=6.9 Hz), 2.37(3H, s), 2.32 (3H, s), 1.26(3H, t, J=6.9 Hz), 1.13(3H, t, J=6.9 Hz)

Reference Example 108

(E)-8-(3,4-Difluorostyryl)-1,3-diethylxanthine (Compound 111)

Substantially the same procedure as in Reference Example 70 was repeated using 2.50 g (12.6 mmol) of 5,6-diamino-1,3-diethyluracil and 2.79 g (15.2 mmol) of 3,4-difluorocinnamic acid. Then, the resultant crude crystals were recrystallized from dioxane/water to give 2.12 g (yield 49%) of Compound 111 as gray plates.

Melting Point: >300° C. Elemental Analysis: $C_{17}H_{16}F_2N_4O_2$ Calcd. (%): C, 58.95; H, 4.65; N, 16.17 Found (%): C, 59.25; H, 4.59; N, 16.42 IR (KBr) $v_{max}$ (cm$^{-1}$): 1688, 1640, 1519 NMR (270 MHz; DMSO-d$_6$) δ (ppm): 7.78(1H, dd, J=11.4, 7.1 Hz), 7.60(1H, d, J=16.3 Hz), 7.50–7.45(2H, m), 7.07(1H, d, J=16.3 Hz), 4.06(2H, q, J=7.0 Hz), 3.94 (2H, q, J=7.1 Hz), 1.26(3H, t, J=7.0 Hz), 1.14(3H, t, J=7.1 Hz)

Reference Example 109

(E)-8-(3,4-Difluorostyryl)-1,3-diethyl-7-methylxanthine (Compound 112)

Substantially the same procedure as in Reference Example 1 was repeated using 1.70 g (4.91 mmol) of Compound 111 obtained in Reference Example 108 in place of Compound B. Then, the resultant crude crystals were recrystallized from toluene/cyclohexane to give 1.29 g (yield 73%) of Compound 112 as yellow needles. Melting Point: 208.5°–210.8° C. Elemental Analysis: $C_{18}H_{18}F_2N_4O_2$ Calcd. (%): C, 59.99; H, 5.03; N, 15.54 Found (%): C, 60.09; H, 5.04; N, 15.19 IR (KBr) $v_{max}$ (cm$^{-1}$): 1688, 1652, 1545, 1520, 1441 NMR (270 MHz; DMSO-d$_6$) δ (ppm): 8.02(1H, ddd, J=12.4, 7.7, 2.0 Hz), 7.65–7.60(1H, m), 7.61(1H, d, J=15.8 Hz), 7.54–7.43 (1H, m), 7.40 (1H, d, J=15.8 Hz), 4.08–4.04 (2H, m), 4.04 (3H, s), 3.92 (2H, q, J=6.9 Hz), 1.26(3H, t, J=6.9 Hz), 1.13 (3H, t, J=6.9 Hz)

Reference Example 110

(E)-8-(3-Bromo-4-methoxystyryl)-1,3-diethylxanthine (Compound 113)

Substantially the same procedure as in Reference Example 70 was repeated using 2.00 g (10.1 mmol) of 5,6-diamino-1,3-diethyluracil and 2.72 g (10.6 mmol) of 3-bromo-methoxycinnamic acid. Then, the resultant crude crystals were recrystallized from dioxane to give 726 mg (yield 17%) of Compound 113 as pale brown needles.

Melting Point: >280° C. Elemental Analysis: $C_{18}H_{19}BrN_4O_3$ Calcd. (%): C, 51 57; H, 4 57; N, 13.36 Found (%): C, 51.33; H, 4.56; N, 13.17 IR (KBr) $\nu_{max}$ (cm$^{-1}$): 1694, 1648, 1506, 1281, 1260 NMR (270 MHz; DMSO-$d_6$) δ (ppm): 13.52(1H, brs), 7.87 (1H, d, J=2.0 Hz), 7.63(1H, dd, J=8.4, 2.0 Hz), 7.56 (1H, d, J=16.3 Hz), 7.16(1H, d, J=8.4 Hz), 6.95(1H, d, J=16.3 Hz), 4.06 (2H, q, J=6.9 Hz), 3.93 (2H, q, J=6.9 Hz), 3.89 (3H, s), 1.26 (3H, t, J=6.9 Hz), 1.14 (3H, t, J=6.9 Hz)

Reference Example 111

(E)-8-(3-Bromo-4-methoxystyryl)-1,3-diethyl-7-methylxanthine (Compound 114)

Substantially the same procedure as in Reference Example 1 was repeated using 400 mg (0.95 mmol) of Compound 113 obtained in Reference Example 110 in place of Compound B. Then, the resultant crude crystals were recrystallized from dioxane/water to give 332 mg (yield 80%) of Compound as pale yellow needles.

Melting Point: 219.1°–223.7° C. Elemental Analysis: $C_{19}H_{21}BrN_4O_3$ Calcd. (%): C, 52.67; H, 4.88; N, 12.93 Found (%): C, 52.79; H, 4.97; N, 12.70 IR (KBr) $\nu_{max}$ (cm$^{-1}$): 1686, 1651, 1541, 1501, 1435 NMR (270 MHz; CDCl$_3$) δ (ppm): 7.83(1H, d, J=2.0 Hz), 7.69(1H, d, J=15.8 Hz), 7.48(1H, dd, J=8.4, 2.0 Hz), 6.92(1H, d, J=8.4 Hz), 6.78(1H, d, J=15.8 Hz), 4.21 (2H, q, J=6.9 Hz), 4.09(2H, q, J=6.9 Hz), 4.06(3H, s), 3.95 (3H, s), 1.38 (3H, t, J=6.9 Hz), 1.26 (3H, t, J=6.9 Hz)

Reference Example 112

(E)-8-(3-Bromo-4-methoxystyryl)theophylline (Compound 115)

Substantially the same procedure as in Reference Example 70 was repeated using 2.00 g (11.8 mmol) of 5,6-diamino-1,3-dimethyluracil and 3.32 g (12.9 mmol) of 3-bromo-4-methoxycinnamic acid. Then, the resultant crude crystals were recrystallized from dimethylformamide to give 2.00 g (yield 43%) of Compound 115 as a pale yellow powder.

Melting Point: >280° C. Elemental Analysis: $C_{16}H_{15}BrN_4O_3$ Calcd. (%): C, 49.12; H, 3.86; N, 14.32 Found (%): C, 49.16; H, 3.80; N, 14.06 IR (KBr) $\nu_{max}$ (cm$^{-1}$): 1691, 1644, 1598, 1499, 1257 NMR (270 MHz; DMSO-$d_6$) δ (ppm): 13.41(1H, brs), 7.84 (1H, d, J=2.0 Hz), 7.61(1H, dd, J=8.4, 2.0 Hz), 7.56 (1H, d, J=16.3 Hz), 7.15(1H, d, J=8.4 Hz), 6.92(1H, d, J=16.3 Hz), 3.89(3H, s), 3.47 (3H, s), 3.26(3H, s)

Reference Example 113

(E)-8-(3-Bromo-4-methoxystyryl)caffeine (Compound 116)

Substantially the same procedure as in Reference Example 1 was repeated using 1.00 g (2.56 mmol) of Compound obtained in Reference Example 112 in place of Compound B. Then, the resultant crude crystals were recrystallized from dioxane to give 877 mg (yield. 85%) of Compound 116 as a yellow powder.

Melting Point: 283.3°–283.4° C. Elemental Analysis: $C_{17}H_{17}BrN_4O_3$ Calcd. (%): C, 50.39; H, 4.23; N, 13.83 Found (%): C, 50.04; H, 4.00; N, 13.49 IR (KBr) $\nu_{max}$ (cm$^{-1}$): 1693, 1654, 1500 NMR (270 MHz; CDCl$_3$) δ (ppm): 7.82(1H, d, J=2.0 Hz), 7.70 (1H, d, J=15.8 Hz), 7.47(1H, dd, J=8.4, 2.0 Hz), 6.92 (1H, d, J=8.4 Hz), 6.78(1H, d, J=15.8 Hz), 4.07 (3H, s), 3.95(3H, s), 3.62(3H, s), 3.42(3H, s)

Reference Example 114

(E)-8-(2-Bromo-4,5-dimethoxystyryl)-1,3-diethylxanthine (Compound 117)

Substantially the same procedure as in Reference Example 70 was repeated using 3.00 g (15.1 mmol) of 5,6-diamino-1,3-diethyluracil and 4.78 g (17.2 mmol) of 2-bromo-4,5-dimethoxycinnamic acid. Then, the resultant crude crystals were recrystallized from dioxane to give 3.34 g (yield 49%) of Compound 117 as pale yellow needles.

Melting Point: >285° C. Elemental Analysis: $C_{19}H_{21}BrN_4O_4$ Calcd. (%): C,50.79; H, 4.71; N, 12.47 Found (%): C,50.49; H, 4.64; N, 12.36 IR (KBr) $\nu_{max}$ (cm$^{-1}$): 1693, 1621, 1509, 1260 NMR (270 MHz; DMSO-$d_6$) δ (ppm): 13.65 (1H, brs), 7.81 (1H, d, J=16.3 Hz), 7.37(1H, s), 7.20(1H, s), 7.06 (1H, d, J=16.3 Hz), 4.07 (2H, q, J=6.9 Hz), 3.95 (2H, q, J=6.9 Hz), 3.86 (3H, s), 3.82 (3H, s), 1.27 (3H, t, J=6.9 Hz), 1.15 (3H, t, J=6.9 Hz)

Reference Example 115

(E)-8-(2-Bromo-4,5-dimethoxystyryl)-1,3-diethyl-7-methylxanthine (Compound 118)

Substantially the same procedure as in Reference Example 1 was repeated using 1.50 g (3.34 mmol) of Compound 117 obtained in Reference Example 114 in place of Compound B. Then, the resultant crude crystals were recrystallized from hexane/ethyl acetate to give 1.43 g (yield 92%) of Compound 118 as yellow needles.

Melting Point: 234.2°–234.9° C. Elemental Analysis: $C_{20}H_{23}BrN_4O_4$ Calcd. (%): C, 51.85; H, 5.00; N, 12.09 Found (%): C, 51.96; H, 4.95; N, 11.90 IR (KBr) $\nu_{max}$ (cm$^{-1}$): 1688, 1648, 1504, 1307, 1261 NMR (270 MHz; CDCl$_3$) δ (ppm): 8.01(1H, d, J=15.8 Hz), 7.11 (1H, s), 7.09(1H, s), 6.76(1H, d, J=15.8 Hz), 4.22 (2H, q, J=6.9 Hz), 4.09 (2H, q, J=6.9 Hz), 4.08 (3H, s), 3.95 (3H, s), 3.92(3H, s), 1.39(3H, t, J=6.9 Hz), 1.27 (3H, t, J=6.9 Hz)

Reference Example 116

(E)-8-(4,5-Dimethoxy-2-nitrostyryl)-1,3-diethylxanthine (Compound 119)

Substantially the same procedure as in Reference Example 70 was repeated using 1.50 g (7.57 mmol) of 5,6-diamino-1,3-diethyluracil and 2.11 g (8.33 mmol) of 4,5-dimethoxy-2-nitrocinnamic acid. Then, the resultant crude crystals were recrystallized from dioxane to give 1.22 g (yield 39%) of Compound 119 as orange needles.

Melting Point: 283.6°–284.2° C. Elemental Analysis: $C_{19}H_{21}N_5O_6$ Calcd. (%): C, 54.94; H, 5.09; N, 16.86 Found (%): C, 54.90; H, 5.07; N, 16.88 IR (KBr) $v_{max}$ (cm$^{-1}$): 1692, 1641, 1520 NMR (270 MHz; DMSO-d$_6$) δ (ppm): 7.99(1H, d, J=16.3 Hz), 7.61(1H, s), 7.38(1H, s), 7.15(1H, d, J=16.3 Hz), 4.06 (2H, q, J=6.9 Hz), 3.98 (3H, s), 3.95 (2H, q, J=6.9 Hz), 3.89(3H, s), 1.26(3H, t, J=6.9 Hz), 1.15 (3H, t, J=6.9 Hz)

Reference Example 117

(E)-8-(4,5-Dimethoxy-2-nitrostyryl)-1,3-diethyl-7-methylxanthine (Compound 120)

Substantially the same procedure as in Reference Example 1 was repeated using 822 mg (1.98 mmol) of Compound 119 obtained in Reference Example 116 in place of Compound B. Then, the resultant crude crystals were recrystallized from ethyl acetate to give 762 mg (yield 90%) of Compound 120 as orange needles.

Melting Point: 246.3°–246.8° C. Elemental Analysis: $C_{20}H_{23}N_5O_6$ Calcd. (%): C, 55.94; H, 5.40; N, 16.31 Found (%): C, 55.98; H, 5.42; N, 16.43 IR (KBr) $v_{max}$ (cm$^{-1}$): 1692, 1657, 1519, 1273 NMR (270 MHz; CDCl$_3$) δ (ppm): 8.27(1H, d, J=15.8 Hz), 7.66(1H, s), 7.03(1 H, s), 6.77(1H, d, J=15.8 Hz), 4.21 (2H, q, J=6.9 Hz), 4.10 (3H, s), 4.09 (2H, q, J=6.9 Hz), 4.05(3H, s), 4.00(3H, s), 1.37(3H, t, J=6.9 Hz), 1.27 (3H, t, J=6.9 Hz)

Reference Example 118

(E)-1,3-Diethyl-8-(3-methoxy-2-nitrostyryl)xanthine (Compound 121)

Substantially the same procedure as in Reference Example 70 was repeated using 2.50 g (12.6 mmol) of 5,6-diamino-1,3-diethyluracil and 3.10 g (13.9 mmol) of 3-methoxy-2-nitrocinnamic acid. Then, the resultant crude crystals were recrystallized from dioxane/water to give 2.28 g (yield 47%) of Compound 121 as orange needles.

Melting Point: >285° C. Elemental Analysis: $C_{18}H_{19}N_5O_5$ Calcd. (%): C, 56.10; H, 4.97; N, 18.17 Found (%): C, 56.37; H, 4.88; N, 17.85 IR (KBr) $v_{max}$ (cm$^{-1}$): 1695, 1640, 1533 NMR (270 MHz; DMSO-d$_6$) δ (ppm): 13.88 (1H, brs), 7.60–7.56 (2H, m), 7.39(1H, d, J=16.3 Hz), 7.32(1H, dd, J=6.9, 3.0 Hz), 7.21(1H, d, J=16.3 Hz), 4.05 (2H, q, J=6.9 Hz), 3.94 (2H, q, J=6.9 Hz), 3.91 (3H, s), 1.25 (3H, t, J=6.9 Hz), 1.14(3H, t, J=6.9 Hz)

Reference Example 119

(E)-1,3-Diethyl-8-(3-methoxy-2-nitrostyryl)-7-methyl-xanthine (Compound 122)

Substantially the same procedure as in Reference Example 1 was repeated using 688 mg (1.79 mmol) of Compound obtained in Reference Example 118 in place of Compound B. Then, the resultant crude crystals were recrystallized from ethyl acetate to give 623 mg (yield 87%) of Compound as yellow needles.

Melting Point: 258.4°–2.59.9° C. Elemental Analysis: $C_{19}H_{21}N_5O_5$ Calcd. (%): C, 57.14; H, 5.30; N, 17.53 Found (%): C, 57.26; H, 5.34; N, 17.26 IR (KBr) $v_{max}$ (cm$^{-1}$): 1697, 1546, 1530 NMR (270 MHz; CDCl$_3$) δ (ppm) : 7.62 (1H, d, J=15.3 Hz), 7.46 (1H, dd, J=8.4, 7.9 Hz), 7.30 (1H, d, J=7.9 Hz), 7.05 (1H, d, J=8.4 Hz), 6.95(1H, d, J=15.3 Hz), 4.19 (2H, q, J=6.9 Hz), 4.08 (2H, q, J=6.9 Hz), 4.05 (3H, s), 3.94(3H, s), 1.36(3H, t, J=6.9 Hz), 1.26(3H, t, J=6.9 Hz)

Reference Example 120

(E)-8-(4-Ethoxystyryl)-1,3-diethylxanthine (Compound 123)

Substantially the same procedure as in Reference Example 70 was repeated using 3.00 g (15.1 mmol) of 5,6-diamino-1,3-diethyluracil and 3.20 g (16.7 mmol) of 4-ethoxycinnamic acid. Then, the resultant crude crystals were recrystallized from dioxane to give 2.97 g (yield 55%) of Compound 123 as pale yellow needles.

Melting Point: 296.7°–298.6° C. Elemental Analysis: $C_{19}H_{22}N_4O_3$ Calcd. (%): C, 64.39; H, 6.25; N, 15.81 Found (%): C, 64.54; H, 6.52; N, 15.80 IR (KBr) $v_{max}$ (cm$^{-1}$): 1695, 1647, 1516, 1250 NMR (270 MHz; DMSO-d$_6$) δ (ppm): 13.36(1H, brs), 7.59 (1H, d, J=16.2 Hz), 7.55(2H, d, J=8.6 Hz), 6.96(2H, d, J=8.6 Hz), 6.88(1H, d, J=16.2 Hz), 4.11–4.04(4H, m), 3.94(2H, q, J=6.9 Hz), 1.34(3H, t, J=6.9 Hz), 1.26(3H, t, J=6.9 Hz), 1.14(3H, t, J=6.9 Hz)

Reference Example 121

(E)-8-(4-Ethoxystyryl)-1,3-diethyl-7-methylxanthine (Compound 124)

Substantially the same procedure as in Reference Example 1 was repeated using 1.60 g (4.52 mmol) of Compound 123 obtained in Reference Example 120 in place of Compound B. Then, the resultant crude crystals were recrystallized from ethyl acetate to give 1.47 g (yield 88%) of Compound 124 as pale green needles.

Melting Point: 185.3°–185.7° C. Elemental Analysis: $C_{20}H_{24}N_4O_3$ Calcd. (%): C, 65.20; H, 6.56; N, 15.21 Found (%): C, 65.28; H, 6.85; N, 15.18 IR (KBr) $v_{max}$ (cm$^{-1}$): 1693, 1666, 1515, 1248 NMR (270 MHz; CDCl$_3$) δ (ppm): 7.74(1H, d, J=15.8 Hz), 7.52 (2H, d, J=8.6 Hz), 6.92 (2H, d, J=8.6 Hz), 6.77 (1H, d, J=15.8 Hz), 4.21(2H, q, J=6.9 Hz), 4.12–4.01 (4H, m), 4.04(3H, s), 1.44(3H, t, J=6.9 Hz), 1.38 (3H, t, J=7.6 Hz), 1.26 (3H, t, J=6.9 Hz)

Reference Example 122

(E)-1,3-Diethyl-8-(4-propoxystyryl)xanthine (Compound 125)

Substantially the same procedure as in Reference Example 70 was repeated using 3.00 g (15.1 mmol) of 5,6-diamino-1,3-diethyluracil and 3.43 g (16.6 mmol) of 4-propoxycinnamic acid. Then, the resultant crude crystals were recrystallized from dioxane/water to give 3.02 g (yield 54%) of Compound 125 as pale yellow needles.

Melting Point: >270° C. Elemental Analysis: $C_{20}H_{24}N_4O_3$ Calcd. (%): C, 65.20; H, 6.56; N, 15.21 Found (%): C, 64.91; H, 6.79; N, 15.14 IR (KBr) $v_{max}$ (cm$^{-1}$): 1695, 1656, 1515, 1250 NMR (270MHz; DMSO-d$_6$) δ (ppm): 13.38(1H, brs), 7.59 (1H, d, J=16.5 Hz), 7.55 (2H, d, J=8.6 Hz), 6.97 (2H, d, J=8.6 Hz), 6.87(1H, d, J=16.5 Hz), 4.07(2H, q, J=7.3 Hz), 4.00–3.90(4H, m), 1.81–1.67(2H, m), 1.26 (3H, t, J=6.9 Hz), 1.14(3H, t, J=6.9 Hz), 0.98(3H, t, J=7.3 Hz)

Reference Example 123

(E)-1,3-Diethyl-7-methyl-8-(4-propoxystyryl)xanthine (Compound 126)

Substantially the same procedure as in Reference Example 1 was repeated using 1.70 g (4.61 mmol) of Compound 125 obtained in Reference Example 122 in place of Compound B. Then, the resultant crude crystals were recrystallized from hexane/ethyl acetate to give 1.37 g (yield 78%) of Compound 126 as pale yellow needles.

Melting Point: 155.7°–156.5° C. Elemental Analysis: $C_{21}H_{26}N_4O_3$ Calcd. (%): C, 65.92; H, 6.85; N, 14.65 Found (%): C, 65.72; H, 7.05; N, 14.59 IR (KBr) $v_{max}$ (cm$^{-1}$): 1696, 1665, 1513, 1246 NMR (270 MHz; CDCl$_3$) δ (ppm): 7.74 (1H, d, J=15.8 Hz), 7.52 (2H, d, J=8.6 Hz), 6.92 (2H, d, J=8.6 Hz), 6.77 (1H, d, J=15.8 Hz), 4.21(2H, q, J=6.9Hz), 4.09(2H, q, J=6.9 Hz), 4.04 (3H, s), 3.97 (2H, t, J=6.6 Hz), 1.90–1.77 (2H, m), 1.38 (3H, t, J=6.9 Hz), 1.26(3H, t, J=6.9 Hz), 1.05(3H, t, J=7.3 Hz)

Reference Example 124

(E)-1,3-Diethyl-8-(3-fluorostyryl)xanthine (Compound 127)

Substantially the same procedure as in Reference Example 70 was repeated using 3.00 g (15.1 mmol) of 5,6-diamino-1,3-diethyluracil and 2.77 g (16.7 retool) of 3-fluorocinnamic acid. Then, the resultant crude crystals were recrystallized from dioxane/water to give 1.96 g (yield 40% of Compound 127 as a pale yellow powder.

Melting Point: >270° C. Elemental Analysis: $C_{17}H_{17}FN_4O_2$ Calcd. (%): C, 62.19; H, 5.22; N, 17.06 Found (%): C, 61.90; H, 5.21; N, 17.15 IR (KBr) $v_{max}$ (cm$^{-1}$): 1692, 1622, 1501 NMR (270 MHz; CF$_3$COOD) δ (ppm): 11.6 (1H, brs), 8.05 (1H, d, J=16.5 Hz), 7.56–7.46(2H, m), 7.38 (1H, d, J=9.2 Hz), 7.29–7.22 (1H, m), 7.19(1H, d, J=16.5 Hz), 4.43–4.03 (4H, m), 1.52 (3H, t, J=7.3 Hz), 1.41 (3H, t, J=6.9 Hz)

Reference Example 125

(E)-1,3-Diethyl-8-(3-fluorostyryl)-7-methylxanthine (Compound 128)

Substantially the same procedure as in Reference Example 1 was repeated using 1.80 g (5.49 mmol) of Compound 127 obtained in Reference Example 124 in place of Compound B. Then, the resultant crude crystals were recrystallized from toluene/cyclohexane to give 1.04 g (yield 55%) of Compound 128 as white needles. Melting Point: 178.2°–179.4° C. Elemental Analysis: $C_{18}H_{19}FN_4O_2.0.25H_2O$ Calcd. (%): C, 62.33; H, 5.67; N, 16.15 Found (%): C, 62.19; H, 5.63; N, 16.26 IR (KBr) $v_{max}$ (cm$^{-1}$): 1694, 1650 NMR (270 MHz; DMSO-d$_6$) δ (ppm). 7.75(1H, dd, J=10.1, 2.0 Hz), 7.66(1H, d, J=15.8 Hz), 7.63–7.60(1H, m), 7.50–7.42(1H, m), 7.44(1H, d, J=15.8 Hz), 7.19(1H, dt, J=2.0, 8.3 Hz), 4.10–4.05(2H, m), 4.05(3H, s), 3.92(2H, q, J=7.0 Hz), 1.26(3H, t, J=7.1 Hz), 1.13 (3H, t, J=7.0 Hz)

Reference Example 126

(E)-8-(3,5-Dimethoxystyryl)-1,3-diethylxanthine (Compound 129)

Substantially the same procedure as in Reference Example 70 was repeated using 3.00 g (15.1 mmol) of 5,6-diamino-1,3-diethyluracil and 3.48 g (16.7 mmol) of 3,5-dimethoxy-cinnamic acid. Then, the resultant crude crystals were recrystallized from ethanol/water to give 2.74 g (yield 49%) of Compound 129 as a white powder.

Melting Point: >270° C. Elemental Analysis: $C_{19}H_{22}N_4O_4.0.5H_2O$ Calcd. (%): C, 60.15; H, 6.11; N, 14.77 Found (%): C, 60.41; H, 6.15; N, 15.02 IR (KBr) $v_{max}$ (cm$^{-1}$): 1686, 1638, 1587 NMR (270 MHz; DMSO-d$_6$) δ (ppm): 7.57(1H, d, J=16.5 Hz), 7.07(1H, d, J=16.5 Hz), 6.79(2H, d, J=2.0 Hz), 6.50 (1H, t, J=2.0 Hz), 4.06(2H, q, J=7.0 Hz), 3.94(2H, q, J=6.9 Hz), 3.79(6H, s), 1.26(3H, t, J=7.0 Hz), 1.14(3H, t, J=6.9 Hz)

Reference Example 127

(E)-8-(3,5-Dimethoxystyryl)-1,3-diethyl-7-methyl-xanthine (Compound 130)

Substantially the same procedure as in Reference Example 1 was repeated using 3.00 g (8.11 mmol) of Compound 129 obtained in Reference Example 126 in place of Compound B. Then, the resultant crude crystals were recrystallized from toluene/cyclohexane to give 2.28 g (yield 73%) of Compound 130 as yellow needles.

Melting Point: 184.2°–185.3° C. Elemental Analysis: $C_{20}H_{24}N_4O_4$ Calcd. (%): C,62.49; H, 6.29; N, 14.57 Found (): C,62.66; H, 6.48; N,14.65 IR (KBr) $v_{max}$ (cm$^{-1}$): 1690, 1659, 1595 NMR (270 MHz; DMSO-d$_6$) δ (ppm): 7.60 (1H, d, J=15.7 Hz), 7.35(1H, d, J=15.7 Hz), 6.98(2H, d, J=2.2 Hz), 6.51 (1H, t, J=2.2 Hz), 4.11–4.01 (2H, m), 4.05 (3H, s), 3.92(2H, q, J=7.0 Hz), 3.80(6H, s), 1.26 (3H, t, J=7.1 Hz), 1.13 (3H, t, J=7.0 Hz)

Reference Example 128

(E)-8-(3-Chlorostyryl)-1,3-diethylxanthine (Compound 131)

Substantially the same procedure as in Reference Example 70 was repeated using 3.50 g (17.7 mmol) of 5,6-diamino-1,3-diethyluracil and 3.55 g (19.4 mmol) of 3-chlorocinnamic acid. Then, the resultant crude crystals were recrystallized from dioxane/water to give 2.57 g (yield 42%) of Compound 131 as white plates.

Melting Point: >280° C. Elemental Analysis: $C_{17}H_{17}ClN_4O_2$ Calcd. (%): C, 59.22; H, 4.97; N, 16.25 Found (%): C, 59.12; H, 5.01; N, 16.30 IR (KBr) $v_{max}$ (cm$^{-1}$): 1689, 1640, 1490 NMR (270 MHz; CF$_3$COOD) δ (ppm): 8.35(1H, d, J=16.4 Hz), 8.01(1H, s), 7.52–7.36(3H, m), 7.14(1H, d, J=16.4 Hz), 4.37–4.23 (4H, m), 1.45 (3H, t, J=6.8 Hz), 1.34(3H, t, J=6.9 Hz)

Reference Example 129

(E)-8-(3-Chlorostyryl)-1,3-diethyl-7-methylxanthine (Compound 132)

Substantially the same procedure as in Reference Example 1 was repeated using 3.00 g (8.72 mmol) of Compound 131 obtained in Reference Example 128 in place of Compound B. Then, the resultant crude crystals were recrystallized from ethanol/water to give 1.41 g (yield 45%) of Compound 132 as a pale yellow powder.

Melting Point: 134.0°–134.4° C. Elemental Analysis: $C_{18}H_{19}ClN_4O_2.H_2O$ Calcd. (%): C, 57.37; H, 5.62; N, 14.87 Found (%): C, 57.67; H, 5.51; N, 14.92 IR (KBr) $v_{max}$ (cm$^{-1}$): 1688, 1656, 1545 NMR (270 MHz; DMSO-d$_6$) δ (ppm): 7.98(1H, s), 7.72(1H, t, J=2.0 Hz), 7.63(1H, d, J=15.8 Hz), 7.49–7.39(3H, m), 4.11–4.03 (2H, m), 4.05 (3H, s), 3.92 (2H, q, J=6.9 Hz), 1.26 (3H, t, J=6.9 Hz), 1.13 (3H, t, J=6.9 Hz)

Reference Example 130

(E)-1,3-Diethyl-8-(α-methylstyryl)xanthine (Compound 133)

Substantially the same procedure as in Reference Example 70 was repeated using 2.00 g (10.1 mmol) of 5,6-diamino-1,3-diethyluracil and 1.80 g (11.1 mmol) of α-methylcinnamic acid. Then, the resultant crude crystals were recrystallized from ethanol/water to give 1.63 g (yield 15%) of Compound 133 as white needles.

Melting Point: 250.8°–252.0° C. Elemental Analysis: $C_{18}H_{20}N_4O_2$ Calcd. (%): C, 66.65; H, 6.21; N, 17.27 Found (%): C, 66.62; H, 6.30; N, 17.31 IR (KBr) $v_{max}$ (cm$^{-1}$): 1696, 1657, 1493 NMR (270 MHz; DMSO-d$_6$) δ (ppm): 13.44(1H, brs), 7.61 (1H, d, J=1.3 Hz), 7.49–7.30(6H, m), 4.07(2H, q, J=7.0 Hz), 3.95(2H, q, J=6.9 Hz), 2.31(3H, d, J=1.3 Hz), 1.26(3H, t, J=7.0 Hz), 1.14 (3H, t, J=6.9 Hz)

Reference Example 131

(E)-1,3-Diethyl-7-methyl-8-(α-methylstyryl)xanthine (Compound 134)

Substantially the same procedure as in Reference Example 1 was repeated using 1.00 g (3.09 mmol) of Compound 133 obtained in Reference Example 130 in place of Compound B. Then, the resultant crude crystals were recrystallized from ethanol/2-propanol to give 800 mg (yield 77%) of Compound 134 as white needles.

Melting Point: 137.2°–139.3° C. Elemental Analysis: $C_{19}H_{22}N_4O_2$ Calcd. (%): C, 67.44; H, 6.55; N, 16.56 Found (%): C, 67.01; H, 6.73; N, 16.62 IR (KBr) $v_{max}$ (cm$^{-1}$): 1699, 1654, 1537 NMR (270 MHz; DMSO-d$_6$) δ (ppm): 7.52–7.32 (SH, m), 7.00 (1H, d, J=1.3 Hz), 4.04(2H, q, J=7.2 Hz), 4.00(3H, s), 3.94(2H, q, J=6.9 Hz), 2.29(3H, d, J=1.3 Hz), 1.24(3H, t, J=7.2 Hz), 1.13(3H, t, J=6.9 Hz)

Reference Example 132

(E)-1,3-Diethyl-8-(4-trifluoromethylstyryl)xanthine (Compound 135)

Substantially the same procedure as in Reference Example 70 was repeated using 2.20 g (11.2 mmol) of 5,6-diamino-1,3-diethyluracil and 2.66 g (12.3 mmol) of 4-trifluoromethyl-cinnamic acid. Then, the resultant crude crystals were recrystallized from dioxane/water to give 2.09 g (yield 49%) of Compound 135 as a white powder.

Melting Point: >280° C. Elemental Analysis: $C_{18}H_{17}F_3N_4O_2$ Calcd. (%): C, 57.14; H, 4.53; N, 14.81 Found (%): C, 57.25; H, 4.51; N, 14.82 IR (KBr) $v_{max}$ (cm$^{-1}$): 1696, 1654, 1637, 1324 NMR (270 MHz; DMSO-d$_6$) δ (ppm): 7.86 (2H, d, J=8.1 Hz), 7.76(2H, d, J=8.1 Hz), 7.70(1H, d, J=16.5 Hz), 7.20 (1H, d, J=16.5 Hz), 4.07(2H, q, J=7.1 Hz), 3.94(2H, q, J=7.0 Hz), 1.26(3H, t, J=7.1 Hz), 1.14(3H, t, J=7.0 Hz)

Reference Example 133

(E)-1,3-Diethyl-7-methyl-8-(4-trifluoromethylstyryl)xanthine (Compound 136)

Substantially the same procedure as in Reference Example 1 was repeated using 1.30 g (3.44 mmol) of Compound 135 obtained in Reference Example 132 in place of Compound B. Then, the resultant crude crystals were recrystallized from toluene/cyclohexane to give 990 mg (yield 73%) of Compound 136 as yellow needles.

Melting Point: 207.8°–209.0° C. Elemental Analysis: $C_{19}H_{19}F_3N_4O_2$ Calcd. (%): C, 58.16; H, 4.88; N, 14.28 Found (%): C, 58.22; H, 4.84; N, 14.32 IR (KBr) $v_{max}$ (cm$^{-1}$): 1700, 1667, 1325 NMR (270 MHz; DMSO-d$_6$) δ (ppm): 8.03(2H, d, J=8.3 Hz), 7.76(2H, d, J=8.3 Hz), 7.73(1H, d, J=15.8 Hz), 7.53 (1H, d, J=15.8 Hz), 4.11–4.03 (2H, m), 4.09 (3H, s), 3.92 (2H, q, J=7.0 Hz), 1.27 (3H, t, J=6.9 Hz), 1.13 (3H, t, J=7.0 Hz)

Reference Example 134

(E)-1,3-Diethyl-8-(α-fluorostyryl)xanthine (Compound 137)

Substantially the same procedure as in Reference Example 70 was repeated using 1.08 g (5.47 mmol) of 5,6-diamino-1,3-diethyluracil and 1.00 g (6.02 mmol) of α-fluorocinnamic acid. Then, the resultant crude crystals were recrystallized from dioxane/water to give 1.04 g (yield 58%) of Compound 137 as white plates.

Melting Point: >280° C. Elemental Analysis: $C_{17}H_{17}FN_4O_2$ Calcd. (%): C, 62.19; H, 5.22; N, 17.06 Found (%): C, 62.28; H, 5.22; N, 17.07 IR (KBr) $v_{max}$ (cm$^{-1}$): 1695, 1644, 1506 NMR (270 MHz; DMSO-d$_6$) δ (ppm): 7.68(2H, d, J=6.9 Hz), 7.47–7.35(3H, m), 6.93(1H, d, J=36.3 Hz), 4.06(2H, q, J=6.9 Hz), 3.94(2H, q, J=7.0 Hz), 1.26(3H, t, J=6.9 Hz), 1.14 (3H, t, J=7.0 Hz)

Reference Example 135

(E)-1,3-Diethyl-8-(α-fluorostyryl)-7-methylxanthine (Compound 138)

Substantially the same procedure as in Reference Example 1 was repeated using 800 mg (2.44 mmol) of Compound 137 obtained in Reference Example 134 in place of Compound B. Then, the resultant crude crystals were recrystallized from toluene/cyclohexane to give 550 mg (yield 66%) of Compound 138 as a white powder.

Melting Point: 153.5°–155.5° C. Elemental Analysis: $C_{18}H_{19}FN_4O_2$ Calcd. (%): C, 63.15; H, 5.59; N, 16.36 Found (%): C, 63.25; H, 5.66; N, 16.44 IR (KBr) $v_{max}$ (cm$^{-1}$): 1696, 1662, 1539 NMR (270 MHz; CDCl$_3$) δ (ppm): 7.68–7.65(2H, m), 7.47–7.31(3H, m), 6.89(1H, d, J=39.3 Hz), 4.13–4.05(2H, m), 4.21 (3H, s), 4.09 (2H, q, J=7.1 Hz), 1.37 (3H, t, J=7.1 Hz), 1.27 (3H, t, J=7.1 Hz)

Reference Example 136

(E)-1,3-Diethyl-8-(3-methoxystyryl)xanthine (Compound 139)

Substantially the same procedure as in Reference Example 70 was repeated using 2.50 g (12.6 mmol) of 5,6-diamino-1,3-diethyluracil and 2.48 g (13.9 mmol) of 3-methoxycinnamic acid. Then, the resultant crude crystals were recrystallized from dimethylformamide/water to give 2.10 g (yield 49%) of Compound 139 as a white powder.

Melting Point: 270.6°–272.5° C. Elemental Analysis: $C_{18}H_{20}N_4O_3$ Calcd. (%): C, 63.52; H, 5.92; N, 16.46 Found (%): C, 63.20; H, 6.01; N, 16.34 IR (KBr) $v_{max}$ (cm$^{-1}$): 1686, 1634, 1500 NMR (270 MHz; DMSO-d$_6$) δ (ppm): 7.61(1H, d, J=16.4 Hz), 7.34 (1H, t, J=7.9 Hz), 7.20–7.18 (2H, m), 7.07 (1H, d, J=16.4 Hz), 6.92 (1H, d, J=8.6 Hz), 4.06 (2H, q, J=7.0 Hz), 3.94 (2H, q, J=6.8 Hz), 1.26(3H, t, J=7.0 Hz), 1.14 (3H, t, J=6.8 Hz)

Reference Example 137

(E)-1,3-Diethyl-8-(3-methoxystyryl)-7-methylxanthine (Compound 140)

Substantially the same procedure as in Reference Example 1 was repeated using 1.70 g (5.00 mmol) of Compound 139 obtained in Reference Example 136 in place of Compound B. Then, the resultant crude crystals were recrystallized from toluene/cyclohexane to give 1.10 g (yield 62%) of Compound 140 as pale yellow needles.

Melting Point: 153.4°–154.8° C. Elemental Analysis: $C_{19}H_{22}N_4O_3$ Calcd. (%): C, 64.39; H, 6.26; N, 15.81 Found (%): C, 64.34; H, 6.38; N, 15.82 IR (KBr) $v_{max}$ (cm$^{-1}$): 1692, 1656, 1541 NMR (270 MHz; DMSO-d$_6$) δ (ppm): 7.64 (1H, d, J=15.8 Hz), 7.40–7.30 (4H, m), 6.97–6.92(1H, m), 4.31–4.05(2H, m), 4.05 (3H, s), 3.92 (2H, q, J=7.0 Hz), 1.26 (3H, t, J=7.1 Hz), 1.13 (3H, t, J=7.0 Hz)

Reference Example 138

(E)-8-(4-Bromostyryl)-1,3-diethylxanthine (Compound 141)

Substantially the same procedure as in Reference Example 70 was repeated using 2.20 g (11.1 mmol) of 5,6-diamino-1,3-diethyluracil and 2.78 g (12.2 mmol) of 4-bromocinnamic acid. Then, the resultant crude crystals were recrystallized from tetrahydrofuran/water to give 930 mg (yield 22%) of Compound 141 as yellow columns.

Melting Point: >270° C. Elemental Analysis: $C_{17}H_{17}BrN_4O_2$ Calcd. (%): C, 52.46; H, 4.40; N, 14.39 Found (%): C, 52.41; H, 4.28; N, 14.43 IR (KBr) $v_{max}$ (cm$^{-1}$): 1686, 1619, 1496 NMR (270 MHz; DMSO-d$_6$) δ (ppm): 7.63–7.18 (4H, m), 7.60 (1H, d, J=16.2 Hz), 7.07(1H, d, J=16.2 Hz), 4.06(2H, q, J=6.9 Hz), 3.94(2H, q, J=6.8 Hz), 1.26(3H, t, J=6.9 Hz), 1.14 (3H, t, J=6.8 Hz)

Reference Example 139

(E)-8-(4-Bromostyryl)-1,3-diethyl-7-methylxanthine (Compound 142)

Substantially the same procedure as in Reference Example 1 was repeated using 1.80 g (4.63 mmol) of Compound 141 obtained in Reference Example 138 in place of Compound B. Then, the resultant crude crystals were recrystallized from toluene/ethanol to give 660 mg (yield 35%) of Compound 142 as pale yellow needles.

Melting Point: 198.5°–198.9° C. Elemental Analysis: $C_{18}H_{19}^{Br}N_4O_2 \cdot 0.25H_2O$ Calcd. (%): C, 53.02; H, 4.82; N, 13.74 Found (%): C, 53.09; H, 4.62; N, 13.79 IR (KBr) $v_{max}$ (cm$^{-1}$): 1691, 1662, 1543 NMR (270 MHz; DMSO-d$_6$) δ (ppm): 7.78(2H, d, J=7.6 Hz), 7.67–7.61 (3H, m), 7.41 (1H, d, J=16.2 Hz), 4.11–4.04 (2H, m), 4.04(3H, s), 3.92(2H, q, J=6.7 Hz), 1.26 (3H, t, J=6.8 Hz), 1.13(3H, t, J=6.7 Hz)

Reference Example 14

(E)-1,3-Diethyl-8-(3-trifluoromethoxystyryl)xanthine (Compound 143)

Substantially the same procedure as in Reference Example 70 was repeated using 1.00 g (5.05 mmol) of 5,6-diamino-1,3-diethyluracil and 1.29 g (5.56 mmol) of 3-trifluoromethoxy-cinnamic acid. Then, the resultant crude crystals were recrystallized from dioxane/water to give 1.19 g (yield 60%) of Compound 143 as white needles.

Melting Point: 266.4°–267.3° C. Elemental Analysis: $C_{18}H_{17}F_3N_4O_3$ Calcd. (%): C, 54.83; H, 4.34; N, 14.21 Found (%): C, 54.79; H, 4.22; N, 14.20 IR (KBr) $v_{max}$ (cm$^{-1}$): 1697, 1658, 1500, 1262 NMR (270 MHz; DMSO-d$_6$) δ (ppm): 13.57 (1H, brs), 7.67 (1H, d, J=16.5 Hz), 7.66(1H, d, J=7.9 Hz), 7.63(1H, s), 7.55(1H, t, J=7.9 Hz), 7.34(1H, d, J=7.9 Hz), 7.14 (1H, d, J=16.5 Hz), 4.07 (2H, q, J=6.9 Hz), 3.94 (2H, q, J=6.9 Hz), 1.27(3H, t, J=6.9 Hz), 1.14(3H, t, J=6.9 Hz)

Reference Example 141

(E)-1,3-Diethyl-7-methyl-8-(3-trifluoromethoxystyryl)xanthine (Compound 144)

Substantially the same procedure as in Reference Example 1 was repeated using 700 mg (1.78 mmol) of Compound 143 obtained in Reference Example 140 in place of Compound B. Then, the resultant crude crystals were recrystallized from ethyl acetate to give 329 mg (yield 45%) of Compound 144 as white needles.

Melting Point: 178.7°–179.3° C. Elemental Analysis: $C_{19}H_{19}F_3N_4O_3$ Calcd. (%): C, 55.88; H, 4.69; N, 13.72 Found (%): C, 56.27; H, 4.68; N, 13.67 IR (KBr) $v_{max}$ (cm$^{-1}$): 1694, 1660, 1265, 1213 NMR (270 MHz; CDCl$_3$) δ (ppm): 7.77(1H, d, J=15.8 Hz), 7.53–7.20(4H, m), 6.93(1H, d, J=15.8 Hz), 4.21(2H, q, J=6.9 Hz), 4.09(2H, q, J=6.9 Hz), 4.08(3H, s), 1.38 (3H, t, J=6.9 Hz), 1.27 (3H, t, J=6.9 Hz)

Reference Example 142

(E)-1,3-Diethyl-8-(4-methoxymethoxystyryl)xanthine (Compound 145)

Substantially the same procedure as in Reference Example 70 was repeated using 4.00 g (20.2 mmol) of 5,6-diamino-1,3-diethyluracil and 4.62 g (22.2 mmol) of 4-methoxymethoxy-cinnamic acid. Then, the resultant crude crystals were recrystallized from dioxane/water to give 4.80 g (yield 64%) of Compound 145 as pale yellow needles.

Melting Point: 270.2°–271.4° C. Elemental Analysis: $C_{19}H_{22}N_4O_4$ Calcd. (%): C, 61.61; H, 5.98; N, 15.13 Found (%): C, 61.97; H, 5.98; N, 15.05 IR (KBr) $v_{max}$ (cm$^{-1}$): 1695, 1641, 1510, 1238 NMR (270 MHz; DMSO-d$_6$) δ (ppm): 13.40 (1H, brs), 7.60 (1H, d, J=16.5 Hz), 7.57(2H, d, J=8.6 Hz), 7.06(2H, d, J=8.6 Hz), 6.90(1H, d, J=16.5 Hz), 5.23(2H, s), 4.07(2H, q, J=6.9 Hz), 3.94(2H, q, J=6.9 Hz), 3.39 (3H, s), 1.26 (3H, t, J=6.9 Hz), 1.14 (3H, t, J=6.9 Hz)

Reference Example 143

(E)-1,3-Diethyl-8-(4-methoxymethoxystyryl)-7-methylxanthine (Compound 146)

Substantially the same procedure as in Reference Example 1 was repeated using 3.50 g (9.45 mmol) of Compound 154 obtained in Reference Example 142 in place of Compound B. Then, the resultant crude crystals were recrystallized from hexane/ethyl acetate to give 3.39 g (yield 93%) of Compound 146 as pale yellow plates.

Melting Point: 163.9°–164.7° C. Elemental Analysis: $C_{20}H_{24}N_4O_4$ Calcd. (%): C, 62.49; H, 6.29; N, 14.57 Found (%): C, 62.21; H, 6.27; N, 14.58 IR (KBr) $\nu_{max}$ (cm$^{-1}$): 1688, 1651, 1510, 1238 NMR (270 MHz; CDCl$_3$) δ (ppm): 7.75(1H, d, J=15.8 Hz), 7.53(2H, d, J=8.6 Hz), 7.07(2H, d, J=8.6 Hz), 6.79 (1H, d, J=15.8 Hz), 5.21(2H, s), 4.21(2H, q, J=6.9 Hz), 4.09(2H, q, J=6.9 Hz), 4.05(3H, s), 3.50 (3H, s), 1.38 (3H, t, J=6.9 Hz), 1.26 (3H, t, J=6.9 Hz)

Reference Example 144

(E)-8-(4-Butoxystyryl)-1,3-diethylxanthine (Compound 147)

Substantially the same procedure as in Reference Example 70 was repeated using 3.00 g (15.1 mmol) of 5,6-diamino-1,3-diethyluracil and 3.67 g (16.7 mmol) of 4-butoxycinnamic acid. Then, the resultant crude crystals were recrystallized from dioxane/water to give 3.04 g (yield of Compound 147 as pale yellow needles.

Melting Point: 257.9°–261.3° C. Elemental Analysis: $C_{21}H_{26}N_4O_3$ Calcd. (%): C, 65.95; H, 6.85; N, 14.65 Found (%): C, 65.90; H, 7.21; N, 14.60 IR (KBr) $\nu_{max}$ (cm$^{-1}$): 1695, 1645, 1515, 1248 NMR (270 MHz; DMSO-d$_6$) δ (ppm): 13.32(1H, brs), 7.59 (1H, d, J=16.5 Hz), 7.55(2H, d, J=8.9 Hz), 6.97(2H, d, J=8.9 Hz), 6.87 (1H, d, J=16.5 Hz), 4.10–3.90 (6H, m), 1.76–1.66 (2H, m), 1.51–1.40 (2H, m), 1.26 (3H, t, J=6.9 Hz), 1.14 (3H, t, J=6.9 Hz), 0.94 (3H, t, J=7.3 Hz)

Reference Example 145

(E)-8-(4-Butoxystyryl)-1,3-diethyl-7-methylxanthine (Compound 148)

Substantially the same procedure as in Reference Example 1 was repeated using 1.50 g (3.92 mmol) of Compound 147 obtained in Reference Example 144 in place of Compound B. Then, the resultant crude crystals were recrystallized from hexane/ethyl acetate to give 982 mg (yield 63%) of Compound 148 as pale yellow needles.

Melting Point: 123.4°–1.23.6° C. Elemental Analysis: $C_{22}H_{28}N_4O_3$ Calcd. (%): C, 66.65; H, 7.11; N, 14.13 Found (%): C, 66.81; H, 7.31; N, 14.01 IR (KBr) $\nu_{max}$ (cm$^{-1}$): 1693, 1665, 1513, 1251 NMR (270 MHz; CDCl$_3$) δ (ppm): 7.74(1H, d, J=15.8 Hz), 7.52 (2H, d, J=8.9 Hz), 6.92 (2H, d, J=8.9 Hz), 6.76 (1H, d, J=15.8 Hz), 4.21(2H, q, J=6.9 Hz), 4.09(2H, q, J=6.9 Hz), 4.04 (3H, s), 4.02 (2H, q, J=6.6 Hz), 1.84–1.74(2H, m), 1.58–1.44(2H, m), 1.38(3H, t, J=6.9 Hz), 1.26(3H, t, J=6.9 Hz), 0.99(3H, t, J=7.3 Hz)

Reference Example 146

(E)-1,3-Diethyl-8-(4-fluorostyryl)xanthine (Compound 149)

Substantially the same procedure as in Reference Example 70 was repeated using 2.50 g (12.6 mmol) of 5,6-diamino-1,3-diethyluracil and 2.31 g (13.9 mmol) of 4-fluorocinnamic acid. Then, the resultant crude crystals were recrystallized from tetrahydrofuran/water to give 2.00 g (yield 51%) of Compound 149 as colorless columns.

Melting Point: >270° C. Elemental Analysis: $C_{17}H_{17}FN_4O_2$ Calcd. (%): C, 62.19; H, 5.22; N, 17.06 Found (%): C, 62.02; H, 5.12; N, 17.02 IR (KBr) $\nu_{max}$ (cm$^{-1}$): 1689, 1560, 1508 NMR (270 MHz; DMSO-d$_6$) δ (ppm): 8.06(1H, d, J=16.3 Hz), 7.72 (2H, dd, J=8.6, 5.2 Hz), 7.21 (2H, t, J=8.6 Hz), 7.10(1H, d, J=16.3 Hz), 4.43–4.30(4H, m), 1.53(3H, t, J=7.2 Hz), 1.41(3H, t, J=7.2 Hz)

Reference Example 147

(E)-1,3-Diethyl-8-(4-fluorostyryl)-7-methylxanthine (Compound 150)

Substantially the same procedure as in Reference Example 1 was repeated using 1.80 g (5.18 mmol) of Compound 149 obtained in Reference Example 146 in place of Compound B. Then, the resultant crude crystals were recrystallized from toluene/cyclohexane to give 510 mg (yield 29%) of Compound 150 as white needles.

Melting Point: 182.0°–182.5° C. Elemental Analysis: $C_{18}H_{19}FN_4O_2$ Calcd. (%): C, 63.15; H, 5.59; N, 16.36 Found (%): C, 63.18; H, 5.61; N, 16.40 IR (KBr) $\nu_{max}$ (cm$^{-1}$): 1687, 1654, 1514 NMR (270 MHz; DMSO-d$_6$) δ (ppm): 7.88(2H, dd, J=8.1, 5.8 Hz), 7.67(1H, d, J=15.8 Hz), 7.41–7.24(3H, m), 4.11–4.03 (2H, m), 4.03 (3H, s), 3.92 (2H, q, J=6.8 Hz), 1.26(3H, t, J=6.9 Hz), 1.13(3H, t, J=6.8 Hz)

Reference Example 148

(E)-1,3-Diethyl-8-(4-methylstyryl)xanthine (Compound 151)

Substantially the same procedure as in Reference Example 70 was repeated using 3.00 g (15.1 mmol) of 5,6-diamino-1,3-diethyluracil and 2.70 g (16.7 mmol) of 4-methylcinnamic acid. Then, the resultant crude crystals were recrystallized from dioxane to give 2.64 g (yield 54%) of Compound 151 as pale yellow needles.

Melting Point: >280° C. Elemental Analysis: $C_{18}H_{20}N_4O_2$ Calcd. (%): C, 66.65; H, 6.21; N, 17.27 Found (%): C, 66.53; H, 6.27; N, 17.14 IR (KBr) $\nu_{max}$ (cm$^{-1}$): 1692, 1644, 1518, 1490 NMR (270 MHz; DMSO-d$_6$) δ (ppm): 13.53 (1H, brs), 7.62 (1H, d, J=16.5 Hz), 7.52(2H, d, J=7.9 Hz), 7.24(2H, d, J=7.9 Hz), 6.98(1H, d, J=16.5 Hz), 4.07(2H, q, J=6.9 Hz), 3.94(2H, q, J=6.9 Hz), 2.33(3H, s), 1.26 (3H, t, J=6.9 Hz), 1.14(3H, t, J=6.9 Hz)

Reference Example 149

(E)-1,3-Diethyl-7-methyl-8-(4-methylstyryl)xanthine (Compound 152)

Substantially the same procedure as in Reference Example 1 was repeated using 1.50 g (4.62 mmol) of Compound obtained in Reference Example 148 in place of Compound B. Then, the resultant crude crystals were recrystallized from dioxane/water to give 1.39 g (yield 89%) of Compound as yellow needles.

Melting Point: 170.8°–171.5° C. Elemental Analysis: $C_{19}H_{22}N_4O_2$ Calcd. (%): C, 67.44; H, 6.55; N, 16.56 Found (%): C, 67.58; H, 6.65; N, 16.68 IR (KBr) $\nu_{max}$ (cm$^{-1}$): 1687, 1650, 1542, 1516 NMR (270 MHz; CDCl$_3$) δ (ppm): 7.77(1H, d, J=15.8 Hz), 7.48 (2H, d, J=8.3 Hz), 7.21 (2H, d, J=8.3 Hz), 6.87 (1H, d, J=15.8 Hz), 4.22(2H, q, J=6.9 Hz), 4.09(2H, q, J=6.9 Hz), 4.05(3H, s), 2.39(3H, s), 1.38(3H, t, J=6.9 Hz), 1.26 (3H, t, J=6.9 Hz)

Reference Example 150

(E)-8-[3,5-Bis(trifluoromethyl)styryl]-1,3-diethylxanthine (Compound 153)

Substantially the same procedure as in Reference Example 70 was repeated using 3.00 g (15.1 mmol) of 5,6-diamino-1,3-diethyluracil and 4.73 g (16.7 mmol) of 3,5-bis(trifluoromethyl) cinnamic acid. Then, the resultant crude crystals were recrystallized from dioxane to give 4.09 g (yield 61%) of Compound 153 as pale yellow needles.

Melting Point: >280° C. Elemental Analysis: $C_{19}H_{16}F_6N_4O_2$ Calcd. (%): C, 51.13; H, 3.61; N, 12.55 Found (%): C, 50.96; H, 3.40; N, 12.52 IR (KBr) $v_{max}$ (cm$^{-1}$): 1694, 1649, 1495, 1287 NMR (270 MHz; DMSO-$d_6$) δ (ppm): 13.75(1H, brs), 8.35 (2H, s), 8.05(1H, s), 7.80(1H, d, J=16.5 Hz), 7.40 (1H, d, J=16.5 Hz), 4.08(2H, q, J=6.9 Hz), 3.94(2H, q, J=6.9 Hz), 1.27(3H, t, J=6.9 Hz), 1.14(3H, t, J=6.9 Hz)

Reference Example 151

(E)-8-[3,5-Bis(trifluoromethyl)styryl]-1,3-diethyl-7-methylxanthine (Compound 154)

Substantially the same procedure as in Reference Example 1 was repeated using 2.00 g (4.68 mmol) of Compound 153 obtained in Reference Example 150 in place of Compound B. Then, the resultant crude crystals were recrystallized from dioxane/water to give 1.43 g (yield 69%) of Compound as pale green needles.

Melting Point: 204.9°–205.1° C. MS-EI m/e: 460 (M$^+$) IR (KBr) $v_{max}$ (cm$^{-1}$): 1699, 1653, 1546, 1282 NMR (270 MHz; DMSO-$d_6$) δ (ppm): 8.55(2H, s), 8.01(1H, s), 7.85(1H, d, J=15.8 Hz), 7.72(1H, d, J=15.8 Hz), 4.09(3H, s), 4.08(2H, q, J=6.9 Hz), 3.93(2H, q, J=6.9 Hz), 1.28(3H, t, J=6.9 Hz), 1.14(3H, t, J=6.9 Hz)

Reference Example 152

(E)-8-(3,5-Difluorostyryl)-1,3-diethylxanthine (Compound 155)

Substantially the same procedure as in Reference Example 70 was repeated using 3.00 g (15.1 mmol) of 5,6-diamino-1,3-diethyluracil and 3.06 g (16.6 mmol) of 3,5-difluorocinnamic acid. Then, the resultant crude crystals were recrystallized from dioxane/water to give 3.30 g (yield 63% of Compound 155 as pale yellow plates.

Melting Point: >280° C. Elemental Analysis: $C_{17}H_{16}F_2N_4O_2$ Calcd. (%): C, 58.96; H, 4.65; N, 16.18 Found (%): C, 58.82; H, 4.65; N, 16.07 IR (KBr) $v_{max}$ (cm$^{-1}$): 1686, 1634, 1589, 1489 NMR (270 MHz; DMSO-$d_6$) δ (ppm): 13.66 (1H, brs), 7.60 (1H, d, J=16.5 Hz), 7.36(2H, dd, J=8.6, 2.0 Hz), 7.20(1H, dt, J=9.2, 2.0 Hz), 7.16(1H, d, J=16.5 Hz), 4.07 (2H, q, J=6.9 Hz), 3.94 (2H, q, J=6.9 Hz), 1.26 (3H, t, J=6.9 Hz), 1.14(3H, t, J=6.9 Hz)

Reference Example 153

(E)-8-(3,5-Difluorostyryl)-1,3-diethyl-7-methylxanthine (Compound 156)

Substantially the same procedure as in Reference Example 1 was repeated using 2.00 g (5.78 mmol) of Compound 155 obtained in Reference Example 152 in place of Compound B. Then, the resultant crude crystals were recrystallized from hexane/ethyl acetate to give 1.80 g (yield 87%) of Compound 156 as pale yellow needles.

Melting Point: 177.0°–178.6° C. MS-EI m/e: 360 (M$^+$) IR (KBr) $v_{max}$ (cm$^{-1}$): 1683, 1619, 1593, 1543 NMR (270 MHz; CDCl$_3$) δ (ppm): 7.70(1H, d, J=15.5 Hz), 7.09 (2H, dd, J=8.3, 2.0 Hz), 6.91(1H, d, J=15.5 Hz), 6.81 (1H, dt, J=8.6, 2.0 Hz), 4.21 (2H, q, J=6.9 Hz), 4.09 (2H, q, J=6.9 Hz), 4.08 (3H, s), 1.38 (3H, t, J=6.9 Hz), 1.27 (3H, t, J=6.9 Hz)

Reference Example 154

(E)-1,3-Diethyl-8-(2-methoxystyryl)xanthine (Compound 157)

Substantially the same procedure as in Reference Example 70 was repeated using 2.5 g (12.6 mmol) of 5,6-diamino-1,3-diethyluracil and 2.48 g (13.9 mmol) of 2-methoxycinnamic acid. Then, the resultant crude crystals were recrystallized from tetrahydrofuran/water to give 990 mg (yield 24%) of Compound 157 as yellow grains.

Melting Point: >270° C. Elemental Analysis: $C_{18}H_{20}N_4O_3$ Calcd. (%): C, 63.52; H, 5.92; N, 16.46 Found (%): C, 63.28; H, 5.86; N, 16.43 IR (KBr) $v_{max}$ (cm$^{-1}$): 1694, 1640, 1501 NMR (270 MHz; DMSO-$d_6$) δ (ppm): 7.85(1H, d, J=16.8 Hz), 7.62 (1H, d, J=7.6 Hz), 7.34(1H, t, J=7.6 Hz), 7.11–6.98 (3H, m), 4.07 (2H, q, J=7.0 Hz), 3.97–3.89 (2H, m), 3.89(3H, s), 1.26(3H, t, J=7.0 Hz), 1.14(3H, t, J=6.9 Hz)

Reference Example 155

(E)-1,3-Diethyl-8-(2-methoxystyryl)-7-methylxanthine (Compound 158)

Substantially the same procedure as in Reference Example 1 was repeated using 1.5 g (4.41 mmol) of Compound obtained in Reference Example 154 in place of Compound B. Then, the resultant crude crystals were recrystallized from ethanol/water to give 800 mg (yield 51%) of Compound 158 as yellow needles.

Melting Point: 189.6°–190.0° C. Elemental Analysis: $C_{19}H_{22}N_4O_3$ Calcd. (%): C, 64.39; H, 6.26; N, 15.81 Found (%): C, 64.18; H, 6.25; N, 15.77 IR (KBr) $v_{max}$ (cm$^{-1}$): 1697, 1649 NMR (270 MHz; DMSO-$d_6$) δ (ppm): 7.94(1H, d, J=15.8 Hz), 7.88 (1H, dd, J=7.9, 1.5 Hz), 7.41–7.34 (1H, m), 7.31 (1H, d, J=15.8 Hz), 7.10(1H, d, J=7.9 Hz), 7.02(1H, t, J=7.4 Hz), 4.11–4.02(2H, m), 4.02(3H, s), 3.96–3.90(2H, m), 3.90(3H, s), 1.29(3H, t, J=7.2 Hz), 1.13 (3H, t, J=7.2 Hz)

Reference Example 156

(E)-1,3-Diethyl-8-(3-nitrostyryl)xanthine (Compound 159)

Substantially the same procedure as in Reference Example 70 was repeated using 2.5 g (12.6 mmol) of 5,6-diamino-1,3-diethyluracil and 2.68 g (13.9 mmol) of 3-nitrocinnamic acid. Then, the resultant crude crystals were recrystallized from dioxane/water to give 2.01 g (yield 30%) of Compound 159 as a yellow powder.

Melting Point: >270° C. Elemental Analysis: $C_{17}H_{17}N_5O_4 \cdot 0.25C_4H_8O_2$ Calcd. (%): C, 57.29; H, 5.07; N, 18.56 Found (%): C, 57.38; H, 5.06; N, 18.63 IR (KBr) $v_{max}$ (cm$^{-1}$): 1688, 1640, 1530 NMR (270 MHz; DMSO-$d_6$) δ (ppm): 8.42(1H, d, J=1.7 Hz), 8.18(1H, dd, J=8.3, 1.7 Hz), 8.12(1H, d, J=7.9 Hz), 7.75 (1H, d, J=16.5 Hz), 7.71 (1H, t, J=7.9 Hz), 7.24 (1H, d, J=16.5 Hz), 4.08(2H, q, J=7.0 Hz), 3.94(2H, q, J=7.0 Hz), 1.27(3H, t, J=7.0 Hz), 1.14(3H, t, J=7.0 Hz)

Reference Example 157

(E)-1,3-Diethyl-7-methyl-8-(3-nitrostyryl)xanthine (Compound 160)

Substantially the same procedure as in Reference Example 1 was repeated using 700 mg (1.97 mmol) of Compound 159 obtained in Reference Example 156 in place of Compound B. Then, the resultant crude crystals were recrystallized from acetonitrile to give 340 mg (yield 47%) of Compound 160 as a yellow powder.

Melting Point: 250.5°–251.7° C. Elemental Analysis: $C_{18}H_{19}N_5O_4$ Calcd. (%): C, 58.53; H, 5.18; N, 18.96 Found (%): C, 58.47; H, 5.13; N, 18.89 IR (KBr) $v_{max}$ (cm$^{-1}$): 1699, 1666, 1524 NMR (270 MHz; DMSO-d$_6$) δ (ppm): 8.72(1H, s), 8.25(1H, d, J=7.9 Hz), 8.19(1H, d, J=7.4 Hz), 7.79(1H, d, J=15.8 Hz), 7.72(1H, t, J=7.9 Hz), 7.63(1H, d, J=15.8 Hz), 4.12–4.05 (2H, m), 4.08 (3H, s), 3.93 (2H, q, J=7.2 Hz), 1.27 (3H, t, J=7.2 Hz), 1.13 (3H, t, J=7.2Hz)

Reference Example 158

(E)-8-(3-Bromostyryl)-1,3-diethylxanthine (Compound 161)

Substantially the same procedure as in Reference Example 70 was repeated using 2.0 g (10.1 mmol) of 5,6-diamino-1,3-diethyluracil and 2.52 g (11.1 mmol) of 3-bromocinnamic acid. Then, the resultant crude crystals were recrystallized from tetrahydrofuran/water to give 2.01 g (yield 37%) of Compound 161 as pale green plates.

Melting Point: >270° C. Elemental Analysis: $C_{17}H_{17}BrN_4O_2$ Calcd. (%): C, 52.46; H, 4.40; N, 14.39 Found (%): C, 52.54; H, 4.44; N, 14.37 IR (KBr) $v_{max}$ (cm$^{-1}$): 1683, 1636, 1492 NMR (270 MHz; CF$_3$COOD) δ (ppm): 7.99 (1H, d, J=16.6 Hz), 7.84 (1H, s), 7.70(1H, d, J=7.9 Hz), 7.62 (1H, d, J=7.9 Hz), 7.40 (1H, t, J=7.9 Hz), 7.19 (1H, d, J=16.6 Hz), 4.40–4.30(4H, m), 1.53(3H, t, J=7.2 Hz), 1.41 (3H, t, J=7.2 Hz)

Reference Example 159

(E)-8-(3-Bromostyryl)-1,3-diethyl-7-methylxanthine (Compound 162)

Substantially the same procedure as in Reference Example 1 was repeated using 2.5 g (6.43 mmol) of Compound 161 obtained in Reference Example 158 in place of Compound B. Then, the resultant crude crystals were recrystallized from toluene/cyclohexane to give 600 mg (yield 69%) of Compound 162 as a yellow powder.

Melting Point: 187.3°–188.2° C. Elemental Analysis: $C_{18}H_{19}BrN_4O_2$ Calcd. (%): C, 53.61; H, 4.75; N, 13.89 Found (%): C, 53.83; H, 4.63; N, 13.70 IR (KBr) $v_{max}$ (cm$^{-1}$): 1694, 1654 NMR (270 MHz; DMSO-d$_6$) δ (ppm): 8.13(1H, s), 7.76(1H, d, J=7.6 Hz), 7.63(1H, d, J=15.8 Hz), 7.54(1H, d, J=8.9 Hz), 7.46(1H, d, J=15.8 Hz), 7.37(1H, t, J=8.2 Hz), 4.11–4.03 (2H, m), 4.05 (3H, s), 3.92 (2H, q, J=6.9 Hz), 1.26(3H, t, J=6.9 Hz), 1.13 (3H, t, J=6.9 Hz)

Reference Example 160

(E)-1,3-Diethyl-8-(3-trifluoromethylstyryl)xanthine (Compound 163)

Substantially the same procedure as in Reference Example 70 was repeated using 2.50 g (12.6 mmol) of 5,6-diamino-1,3-diethyluracil and 3.0 g (13.9 mmol) of 3-trifluoromethyl-cinnamic acid. Then, the resultant crude crystals were recrystallized from acetonitrile/water to give 2.07 g (yield 44%) of Compound 163 as white needles.

Melting Point: >270° C. Elemental Analysis: $C_{18}H_{17}F_3N_4O_2$ Calcd. (%): C, 57.14; H, 4.53; N, 14.81 Found (%): C, 57.15; H, 4.47; N, 14.65 IR (KBr) $v_{max}$ (cm$^{-1}$): 1691, 1641, 1495, 1334 NMR (270 MHz; DMSO-d$_6$) δ (ppm): 13.65 (1H, brs), 7.99–7.95 (2H, m), 7.76–7.63(3H, m), 7.21(1H, d, J=1 6.1 Hz), 4.07 (2H, q, J=6.9 Hz), 3.94 (2H, q, J=6.7 Hz), 1.27 (3H, t, J=6.9 Hz), 1.14 (3H, t, J=6.7 Hz)

Reference Example 161

(E)-1,3-Diethyl-7-methyl-8-(3-trifluoromethylstyryl)xanthine (Compound 164)

Substantially the same procedure as in Reference Example 1 was repeated using 1.70 g (4.50 mmol) of Compound obtained in Reference Example 160 in place of Compound B. Then, the resultant crude crystals were recrystallized from toluene/cyclohexane to give 1.14 g (yield 65%) of Compound 164 as a pale yellow powder.

Melting Point: 214.8°–215.3° C. Elemental Analysis: $C_{19}H_{19}F_3N_4O_2$ Calcd. (%): C, 58.16; H, 4.88; N, 14.28 Found (%): C, 58.13; H, 4.90; N, 14.22 IR (KBr) $v_{max}$ (cm$^{-1}$): 1697, 1664 NMR (270 MHz; DMSO-d$_6$) δ (ppm): 8.26(1H, s), 8.09(1H, d, J=7.4Hz), 7.75 (1H, d, J=15.8 Hz), 7.69–7.62 (2H, m), 7.56 (1H, d, J=15.8 Hz), 4.12–4.00 (2H, m), 4.07 (3H, s), 3.92 (2 H, q, J=6.9 Hz), 1.27(3H, t, J=6.9 Hz), 1.13 (3H, t, J=6.9 Hz)

Reference Example 162

(E)-8-(2-Bromo-4,5-methylenedioxystyryl)-1,3-diethylxanthine (Compound 165)

Substantially the same procedure as in Reference Example 70 was repeated using 2.50 g (12.6 mmol) of 5,6-diamino-1,3-diethyluracil and 3.77 g (13.9 mmol) of 2-bromo-4,5-methylenedioxycinnamic acid. Then, the resultant crude crystals were recrystallized from dimethylsulfoxide/water to give 2.01 g (yield 38%) of Compound 165 as a yellow powder.

Melting Point: >270° C. Elemental Analysis: $C_{18}H_{17}BrN_4O_4 \cdot 0.25H_2O$ Calcd. (%): C, 49.39; H, 4.03; N, 12.80 Found (%): C, 49.42; H, 3.75; N, 12.67 IR (KBr) $v_{max}$ (cm$^{-1}$): 1691, 1651, 1497 NMR (270 MHz; DMSO-d$_6$) δ (ppm): 7.78(1H, d, J=8.2 Hz), 7.48(1H, s), 7.30(1H, s), 6.97(1H, d, J=8.2 Hz), 6.13(2H, s), 4.05(2H, q, J=6.9 Hz), 3.93(2H, q, J=6.9 Hz), 1.24(3H, t, J=6.9 Hz), 1.13(3H, t, J=6.9 Hz)

Reference Example 163

(E)-8-(2-Bromo-4,5-methylenedioxystyryl)-1,3-diethyl-7-methylxanthine (Compound 166)

Substantially the same procedure as in Reference Example 1 was repeated using 2.20 g (5.08 mmol) of Compound 165 obtained in Reference Example 162 in place of Compound B. Then, the resultant crude crystals were recrystallized from toluene/cyclohexane to give 1.17 g (yield 52%) of Compound 166 as a pale yellow powder.

Melting Point: 255.1°–256.0° C. Elemental Analysis: $C_{19}H_{19}BrN_4O_4$ Calcd. (%): C, 51.02; H, 4.28; N, 12.53 Found (%): C, 50.94; H, 4.15; N, 12.39 IR (KBr) $v_{max}$ (cm$^{-1}$): 1693, 1651 NMR (270 MHz; DMSO-d$_6$) δ (ppm): 7.87(1H, d, J=15.8 Hz), 7.77(1H, s), 7.30(1H, d, J=15.8 Hz), 7.32(1H, s), 6.15 (2H, s), 4.10–4.03 (2H, m), 4.03 (3H, s), 3.92 (2H, q, J=6.8 Hz), 1.26(3H, t, J=7.2 Hz), 1.13(3H, t, J=6.8 Hz)

Reference Example 164

(E)-1,3-Diethyl-8-(2-fluorostyryl)xanthine (Compound 167)

Substantially the same procedure as in Reference Example 70 was repeated using 2.70 g (13.6 mmol) of 5,6-diamino-1,3-diethyluracil and 2.49 g (15.0 mmol) of 2-fluorocinnamic acid. Then, the resultant crude crystals were recrystallized from dioxane/water to give 1.81 g (yield of Compound 167 as a white powder.

Melting Point: >270° C. Elemental Analysis: $C_{17}H_{17}FN_4O_2$ Calcd. (%): C, 62.19; H, 5.22; N, 17.06 Found (%): C, 62.31; H, 5.23; N, 17.09 IR (KBr) $v_{max}$ (cm$^{-1}$): 1687, 1650, 1557, 1498, 1451 NMR (270 MHz; DMSO-d$_6$) δ (ppm): 7.81(1H, t, J=7.9 Hz), 7.72(1H, d, J=16.3 Hz), 7.42–7.25(3H, m), 7.15(1H, d, J=16.3 Hz), 4.07(2H, q, J=6.9 Hz), 3.94(2H, q, J=6.9 Hz), 1.26(3H, t, J=6.9 Hz), 1.14(3H, t, J=6.9 Hz)

Reference Example 165

(E)-1,3-Diethyl-8-(2-fluorostyryl)-7-methylxanthine (Compound 168)

Substantially the same procedure as in Reference Example 1 was repeated using 1.30 g (3.96 mmol) of Compound 167 obtained in Reference Example 164 in place of Compound B. Then, the resultant crude crystals were recrystallized from toluene/cyclohexane to give 440 mg (yield 32%) of Compound 168 as white needles.

Melting Point: 184.1°–184.6° C. Elemental Analysis: $C_{18}H_{19}FN_4O_2$ Calcd. (%): C, 63.15; H, 5.59; N, 16.36 Found (%): C, 63.01; H, 5.61; N, 16.27 IR (KBr) $v_{max}$ (cm$^{-1}$): 1697, 1668, 1541 NMR (270 MHz; DMSO-d$_6$) δ (ppm): 8.04(1H, t, J=8.4 Hz), 7.77 (1H, d, J=15.8 Hz), 7.47–7.43 (1H, m), 7.45 (1H, d, J=15.8 Hz), 7.35–7.27 (2H, m), 4.11–4.04 (2H, m), 4.04(3H, s), 3.92(2H, q, J=7.0 Hz), 1.26(3H, t, J=6.9 Hz), 1.13 (3H, t, J=7.0 Hz)

Reference Example 166

(E)-8-[4-(N,N-Dimethylamino)styryl]-1,3-diethylxanthine (Compound 169)

Substantially the same procedure as in Reference Example 70 was repeated using 3.00 g (15.1 mmol) of 5,6-diamino-1,3-diethyluracil and 3.30 g (17.3 mmol) of 4-(N,N-dimethylamino) cinnamic acid. Then, the resultant crude crystals were recrystallized from dioxane to give 2.78 g (yield 52%) of Compound 169 as yellow needles.

Melting Point: >300° C. Elemental Analysis: $C_{19}H_{23}N_5O_2$ Calcd. (%): C, 64.57; H, 6.56; N, 19.82 Found (%): C, 64.78; H, 6.73; N, 19.94 IR (KBr) $v_{max\ (cm}^{-1})$: 1691, 1650, 1606, 1530 NMR (270 MHz; DMSO-d$_6$) δ (ppm): 13.20(1H, brs), 7.54 (1H, d, J=16.2 Hz), 7.44(2H, d, J=8.6 Hz), 6.75(1H, d, J=16.2 Hz), 6.74(2H, d, J=8.6 Hz), 4.06(2H, q, J=6.9 Hz), 3.94(2H, q, J=6.9 Hz), 2.97(6H, s), 1.26 (3H, t, J=6.9 Hz), 1.14(3H, t, J=6.9 Hz)

Reference Example 167

(E)-1,3-Diethyl-8-(4-phenylstyryl)xanthine (Compound 170)

Substantially the same procedure as in Reference Example 70 was repeated using 2.50 g (12.6 mmol) of 5,6-diamino-1,3-diethyluracil and 3.12 g (13.9 mmol) of 4-phenylcinnamic acid. Then, the resultant crude crystals were recrystallized from dioxane/water to give 1.90 g (yield of Compound 170 as yellow flocculent precipitates.

Melting Point: >270° C. Elemental Analysis: $C_{23}H_{22}N_4O_2 \cdot 0.25H_2O$ Calcd. (%): C, 70.66; H, 5.80; N, 14.33 Found (%): C, 70.90; H, 5.75; N, 14.32 IR (KBr) $v_{max}$ (cm$^{-1}$): 1689, 1639, 1492 NMR (270 MHz; DMSO-d$_6$) δ (ppm): 7.80–7.65(7H, m), 7.49 (2H, t, J=7.3 Hz), 7.39(1H, t, J=7.3 Hz), 7.10(1H, d, J=16.3 Hz), 4.07(2H, q, J=7.1 Hz), 3.94(2H, q, J=6.8 Hz), 1.27 (3H, t, J=7.1 Hz), 1.14 (3H, t, J=6.8 Hz)

Reference Example 168

(E)-1,3-Diethyl-7-methyl-8-(4-phenylstyryl)xanthine (Compound 171)

Compound 170 (1.50 g, 3.89 mmol) obtained in Reference Example 167 was suspended in a mixed solvent of 13 ml of water, 3.9 ml of a 2N aqueous solution of sodium hydroxide, and 7 ml of methanol. To the suspension was dropwise added 0.55 ml (5.83 mmol) of dimethyl sulfate, and the resultant mixture was stirred at 60° C. for 4 hours. Water (10 ml) was added thereto, and the deposited crystals were collected by filtration and dried. The obtained crude crystals were purified by silica gel column chromatography, followed by recrystallization from ethyl acetate to give 480 mg (yield 28%) of Compound 171 as yellow columns.

Melting Point: 200.5°–201.3° C. Elemental Analysis: $C_{24}H_{24}N_4O_2 \cdot 0.5CH_3CO_2C_2H_5$ Calcd. (%): C, 70.25; H, 6.35; N, 12.72 Found (%): C, 70.36; H, 6.47; N, 12.60 IR (KBr) $v_{max}$ (cm$^{-1}$): 1685, 1649, 1541 NMR (270MHz; DMSO-d$_6$) δ (ppm): 7.95(1H, d, J=14.8 Hz), 7.76–7.69(6H, m), 7.52–7.45(3H, m), 7.39(1H, t, J=6.4 Hz), 4.12–3.99 (2H, m), 4.06 (3H, s), 3.92 (2H, q, J=6.9 Hz), 1.27(3H, t, J=6.9 Hz), 1.14(3H, t, J=7.0 Hz)

Reference Example 169

(E)-1,3-Diethyl-8-(3-fluoro-4-methoxystyryl)xanthine (Compound 172)

Substantially the same procedure as in Reference Example 70 was repeated using 2.50 g (12.6 mmol) of 5,6-diamino-1,3-diethyluracil and 2.72 g (13.9 mmol) of 3-fluoro-4-methoxycinnamic acid. Then, the resultant crude crystals were recrystallized from dioxane/water to give 1.97 g (yield 44%) of Compound 172 as pale yellow flocculent precipitates.

Melting Point: >270° C. Elemental Analysis: $C_{18}H_{19}FN_4O_3$ Calcd. (%): C, 60.33; H, 5.34; N, 15.63 Found (%): C, 59.99; H, 5.34; N, 15.57 IR (KBr) $v_{max}$ (cm$^{-1}$): 1694, 1644, 1520, 1491 NMR (270 MHz; DMSO-d$_6$) δ (ppm): 7.61–7.54 (2H, m), 7.40 (1H, d, J=8.8 Hz), 7.21 (1H, t, J=8.8 Hz), 6.93 (1H, d, J=16.3 Hz), 4.06 (2H, q, J=7.1

Hz), 3.97–3.88 (2H, m), 3.88 (3H, s), 1.25 (3H, t, J=7.2 Hz), 1.14 (3H, t, J=7.1 Hz)

Reference Example 170

(E)-1,3-Diethyl-8-(3-fluoro-4-methoxystyryl)-7-methylxanthine (Compound 173)

Substantially the same procedure as in Reference Example 1 was repeated using 1.50 g (4.19 mmol) of Compound 172 obtained in Reference Example 169 in place of Compound B. Then, the resultant crude crystals were recrystallized from toluene/ethanol to give 1.22 g (yield 78%) of Compound as a pale yellow powder.

Melting Point: 211.7°–212.2° C. Elemental Analysis: $C_{19}H_{21}FN_4O_3 \cdot 0.25H_2O$ Calcd. (%): C, 60.55; H, 5.75; N, 14.87 Found (%): C, 60.75; H, 5.81; N, 14.92 IR (KBr) $v_{max}$ (cm$^{-1}$): 1694; 1653, 1544, 1520, 1459 NMR (270 MHz; DMSO-d$_6$) δ (ppm): 7.82(1H, dd, J=12.9, 2.0 Hz), 7.59(1H, d, J=15.8 Hz), 7.56–7.52 (1H, m), 7.26 (1H, d, J=15.8 Hz), 7.19(1H, t, J=8.9 Hz), 4.10–4.02 (2H, m), 4.02 (3H, s), 3.94–3.88 (2H, m), 3.88 (3H, s), 1.25(3H, t, J=6.9 Hz), 1.13(3H, t, J=6.9 Hz)

Reference Example 171

(E)-1,3-Diethyl-8-(4-methoxy-3-methylstyryl)xanthine (Compound 174)

Substantially the same procedure as in Reference Example 70 was repeated using 2.50 g (12.6 mmol) of 5,6-diamino-1,3-diethyluracil and 3.00 g (13.9 mmol) of 4-methoxy-3-methylcinnamic acid. Then, the resultant crude crystals were recrystallized from dimethylsulfoxide/water to give 1.70 g (yield 36%) of Compound 174 as white flocculent precipitates.

Melting Point: >270° C. Elemental Analysis: $C_{19}H_{22}N_4O_3$ Calcd. (%): C, 64.39; H, 6.23; N, 15.81 Found (%): C, 64.05; H, 6.34; N, 15.74 IR (KBr) $v_{max}$ (cm$^{-1}$): 1689, 1644, 1510, 1459 NMR (270 MHz; DMSO-d$_6$) δ (ppm): 7.56(1H, d, J=16.3 Hz), 7.45(1H, s), 7.44 (1H, d, J=8.2 Hz), 6.98 (1H, J=8.2 Hz), 6.87(1H, d, J=16.3 Hz), 4.06(2H, q, J=7.1 Hz), 3.93 (2H, q, J=7.0 Hz), 3.82 (3H, s), 2.18 (3H, s), 1.25 (3H, t, J=7.1 Hz), 1.13 (3H, t, J=7.0 Hz)

Reference Example 172

(E) -1,3-Diethyl-8-(4-methoxy-3-methylstyryl)-7-methylxanthine (Compound 175)

Substantially the same procedure as in Reference Example 1 was repeated using 1.27 g (3.36 mmol) of Compound 174 obtained in Reference Example 171 in place of Compound B. Then, the resultant crude crystals were recrystallized from toluene/cyclohexane to give 1.01 g (yield 82%) of Compound 175 as yellow needles.

Melting Point: 176.5°–177.6° C. Elemental Analysis: $C_{20}H_{24}N_4O_3$ Calcd. (%): C, 65.20; H, 6.57; N, 15.21 Found (%): C, 65.22; H, 6.75; N, 15.22 IR (KBr) $v_{max}$ (cm$^{-1}$): 1687, 1648, 1542, 1505, 1434 NMR (270 MHz; DMSO-d$_6$) δ (ppm): 7.65(1H, s), 7.58 (1H, d, J=15.8 Hz), 7.57–7.53(1H, m), 7.16(1H, d, J=15.8 Hz), 6.97(1H, d, J=8.9 Hz), 4.10–4.01(2H, m), 4.01 (3H, s), 3.91 (2H, q, J=6.9 Hz), 3.88 (3H, s), 2.19(3H, s), 1.25(3H, t, J=6.9 Hz), 1.12(3H, t, J=6.9 Hz)

Reference Example 173

(E)-8-(3-Chloro-4-fluorostyryl)-1,3-diethylxanthine (Compound 176)

Substantially the same procedure as in Reference Example 70 was repeated using 2.50 g (12.6 mmol) of 5,6-diamino-1,3-diethyluracil and 3.01 g (15.1 mmol) of 3-chloro-4-fluorocinnamic acid. Then, the resultant crude crystals were recrystallized from tetrahydrofuran/water to give 560 mg (yield 32%) of Compound 176 as a white powder.

Melting Point: >270° C. Elemental Analysis: $C_{17}H_{16}ClFN_4O_2$ Calcd. (%): C, 56.28; H, 4.45; N, 15.44 Found (%): C, 56.30; H, 4.43; N, 15.53 IR (KBr) $v_{max}$ (cm$^{-1}$): 1695, 1649, 1504 NMR (270 MHz; DMSO-d$_6$) δ (ppm): 7.93–7.91 (1H, m), 7.66–7.63(1H, m), 7.58(1H, d, J=16.3 Hz), 7.46(1H, t, J=8.9 Hz), 7.08(1H, d, J=16.3 Hz), 4.05(2H, q, J=7.1 Hz), 3.93(2H, q, J=6.8 Hz), 1.26(3H, t, J=7.1 Hz), 1.14 (3H, t, J=6.8 Hz)

Reference Example 174

(E)-8-(3-Chloro-4-fluorostyryl)-1,3-diethyl-7-methylxanthine (Compound 177)

Substantially the same procedure as in Reference Example 1 was repeated using 1.80 g (4.98 mmol) of Compound 176 obtained in Reference Example 173 in place of Compound B. Then, the resultant crude crystals were recrystallized from ethyl acetate to give 820 mg (yield 44%) of Compound as yellow needles.

Melting Point: 218.4°–219.1° C. Elemental Analysis: $C_{18}H_{18}ClFN_4O_2$ Calcd. (%): C, 57.37; H, 4.81; N, 14.87 Found (%): C, 57.23; H, 4.85; N, 14.81 IR (KBr) $v_{max}$ (cm$^{-1}$): 1693, 1648, 1541, 1505, 1438 NMR (270 MHz; DMSO-d$_6$) δ (ppm): 8.18(1H, dd, J=7.2, 2.3Hz), 7.84–7.79(1H, m), 7.63(1H, d, J=15.8 Hz), 7.51–7.44 (2H, m), 4.11–3.99 (2H, m), 4.05 (3H, s), 3.92(2H, q, J=6.9 Hz), 1.25(3H, t, J=6.9 Hz), 1.13 (3H, t, J=6.9 Hz)

Reference Example 175

(E)-1,3-Diethyl-8-(3-methoxy-4,5-methylenedioxystyryl)xanthine (Compound 178)

Substantially the same procedure as in Reference Example 70 was repeated using 2.50 g (12.6 mmol) of 5,6-diamino-1,3-diethyluracil and 3.31 g (14.9 mmol) of 3-methoxy-4,5-methylenedioxycinnamic acid. Then, the resultant crude crystals were recrystallized from tetrahydrofuran/water to give 600 mg (yield 53%) of Compound as a white powder.

Melting Point: >270° C. Elemental Analysis: $C_{19}H_{20}N_4O_5$ Calcd. (%): C, 59.37; H, 5.24; N, 14.58 Found (%): C, 59.41; H, 5.26; N, 14.66 IR (KBr) $v_{max}$ (cm$^{-1}$): 1689, 1654, 1640, 1506 NMR (270 MHz; DMSO-d$_6$) δ (ppm): 7.54(1H, d, J=16.6 Hz), 6.94(2H, s), 6.93(1H, d, J=16.6 Hz), 6.04(2H, s), 4.05 (2H, q, J=6.9 Hz), 3.97–3.88 (2H, m), 3.88 (3H, s), 1.25(3H, t, J=7.2 Hz), 1.13(3H, t, J=7.2 Hz)

Reference Example 176

(E)-1,3-Diethyl-8-(3-methoxy-4,5-methylenedioxystyryl)7-methylxanthine (Compound 179)

Substantially the same procedure as in Reference Example 1 was repeated using 2.00 g (5.20 mmol) of Compound 178 obtained in Reference Example 175 in place of Compound B. Then, the resultant crude crystals were recrystallized from 2-propanol to give 730 mg (yield 35%) of Compound 179 as a yellow powder.

Melting Point: 201.5°–202.3° C. Elemental Analysis: $C_{20}H_{22}N_4O_5$ Calcd. (%): C, 60.29; H, 5.57; N, 14.06 Found (%): C, 60.18; H, 5.72; N, 13.98 IR (KBr) $v_{max}$ (cm$^{-1}$): 1694, 1650, 1543, 1512, 1433 NMR (270 MHz; DMSO-d$_6$) δ (ppm): 7.58(1H, d, J=15.8 Hz), 7.23 (1H, d, J=15.8 Hz), 7.20 (1H, d, J=1.0 Hz), 7.09 (1H, d, J=1.0 Hz), 6.05(2H, s), 4.09–4.02(2H, m), 4.02 (3H, s), 3.94–3.89 (2H, m), 3.89 (3H, s), 1.25 (3H, t, J=7.2 Hz), 1.13(3H, t, J=6.9 Hz)

Reference Example 177

(E)-1,3-Diethyl-8-(3-fluoro-2-methylstyryl)xanthine (Compound 180)

Substantially the same procedure as in Reference Example 70 was repeated using 2.50 g (12.6 mmol) of 5,6-diamino-1,3-diethyluracil and 2.50 g (13.9 mmol) of 3-fluoro-2-methylcinnamic acid. Then, the resultant crude crystals were recrystallized from dioxane to give 2.18 g (yield 51%) of Compound 180 as a white powder.

Melting Point: >270° C. Elemental Analysis: $C_{18}H_{19}FN_4O_2$ Calcd. (%): C, 63.15; H, 5.59; N, 16.36 Found (%): C, 62.81; H, 5.71; N, 16.09 IR (KBr) $v_{max}$ (cm$^{-1}$): 1696, 1658, 1499 NMR (270 MHz; DMSO-d$_6$) δ (ppm): 13.7 (1H, brs), 7.87 (1H, d, J=16.6 Hz), 7.59 (1H, d, J=7.4 Hz), 7.31–7.23 (1H, m), 7.15 (1H, t, J=8.7 Hz), 7.05 (1H, d, J=1 6.6 Hz), 4.06 (2H, q, J=6.9 Hz), 3.94 (2H, q, J=6.9 Hz), 2.33 (3H, d, J=2.0 Hz), 1.26(3H, t, J=7.1 Hz), 1.14 (3H, t, J=6.9 Hz)

Reference Example 178

(E)-1,3-Diethyl-8-(3-fluoro-2-methylstyryl)-7-methylxanthine (Compound 181)

Substantially the same procedure as in Reference Example 1 was repeated using 1.30 g (3.80 mmol) of Compound 180 obtained in Reference Example 177 in place of Compound B. Then, the resultant crude crystals were recrystallized from 2-propanol/water to give 1.12 g (yield 83%) of Compound as white flocculent precipitates.

Melting Point: 198.1°–198.7° C. Elemental Analysis: $C_{19}H_{21}FN_4O_2 \cdot 0.5H_2O$ Calcd. (%): C, 62.45; H, 6.07; N, 15.33 Found (%): C, 62.39; H, 6.26; N, 15.25 IR (KBr) $v_{max}$ (cm$^{-1}$): 1695, 1654, 1543 NMR (270 MHz; DMSO-d$_6$) δ (ppm):. 7.85(1H, d, J=15.5 Hz), 7.75 (1H, d, J=7.9 Hz), 7.34–7.27 (1H, m), 7.29(1H, d, J=15.5 Hz), 7.18(1H, t, J=8.9 Hz), 4.12–4.04(2H, m), 4.04(3H, s), 3.92(2H, q, J=6.9 Hz), 2.32 (3H, d, J=1.7 Hz), 1.27 (3H, t, J=7.1 Hz), 1.13 (3H, t, J=6.9 Hz)

Reference Example 179

(E)-8-(3,4-Dihydroxystyryl)-1,3-diethyl-7-methylxanthine (Compound 182)

Compound 74 (2.00 g, 5.20 mmol) obtained in Reference Example 71 was dissolved in 40 ml of methylene chloride. To the solution was added 26 ml (26 mmol) of boron tribromide (1.0M methylene chloride solution) under ice cooling in argon atmosphere, and the mixture was stirred overnight at room temperature. Methanol was added thereto and the mixture was separated with chloroform-an aqueous solution of sodium bicarbonate. The organic layer was washed with a saturated aqueous solution of sodium chloride and dried over anhydrous sodium sulfate, followed by evaporation under reduced pressure. The residue was recrystallized from ethanol to give 643 mg (yield 35%) of Compound 182 as pale yellow grains.

Melting Point: 247.5°–248.2° C. MS-EI m/e: 356 (M$^+$) IR (KBr) $v_{max}$ (cm$^{-1}$): 1675, 1642, 1543, 1520, 1298 NMR (270 MHz; DMSO-d$_6$) δ (ppm): 9.31(1H, brs), 8.95(1H, brs), 7.50(1H, d, J=15.8 Hz), 7.16(1H, s), 7.05(1H, d, J=7.9 Hz), 7.00(1H, d, J=15.8 Hz), 6.77(1H, d, J=7.9 Hz), 4.06 (2H, q, J=6.9 Hz), 3.99 (3H, s), 3.92 (2H, q, J=6.9 Hz), 1.25(3H, t, J=6.9 Hz), 1.13(3H, t, J=6.9 Hz)

Reference Example 180

(E)-1,3-Diethyl-8-(3-hydroxy-4-methoxystyryl)-7-methylxanthine (Compound 183)

Substantially the same procedure as in Reference Example 61 was repeated using 400 mg (1.12 mmol) of Compound obtained in Reference Example 179 to give 127 mg (yield of Compound 183 as a pale brown powder. The obtained crude crystals were further recrystallized from ethanol.

Melting Point: 204.5°–205.8° C. MS-EI m/e: 370 (M$^+$) IR (KBr) $v_{max}$ (cm$^{-1}$): 1689, 1653, 1515, 1442 NMR (270 MHz; DMSO-d$_6$) δ (ppm): 9.06 (1H, s), 7.53 (1H, d, J=15.5 Hz), 7.23(1H, s), 7.17(1H, d, J=8.3 Hz), 7.08(1H, d, J=15.5 Hz), 6.96(1H, d, J=8.3 Hz), 4.06 (2H, q, J=6.9 Hz), 4.00(3H, s), 3.92(2H, q, J=6.9 Hz), 3.82(3H, s), 1.25(3H, t, J=6.9 Hz), 1.13 (3H, t, J=6.9 Hz)

Reference Example 181

(E)-1,3-Diethyl-8-(4-hydroxystyryl)-7-methylxanthine (Compound 184)

Compound 146 (2.70 g, 7.02 mmol) obtained in Reference Example 143 was dissolved in 50 ml of tetrahydrofuran. To the solution was added 17.6 ml of 2N hydrochloric acid, and the mixture was heated under reflux for 2.5 hours. The reaction solution was neutralized with a N aqueous solution of sodium hydroxide under ice cooling, water was added thereto, and the deposited crystals were collected by filtration. The obtained crude crystals were recrystallized from 2-propanol to give 2.33 g (yield 98%) of Compound 184 as yellow grains.

Melting Point: >270° C. Elemental Analysis: $C_{18}H_{20}N_4O_3$ Calcd. (%): C, 63.52; H, 5.92; N, 16.46 Found (%): C, 63.17; H, 6.02; N, 16.18 IR (KBr) $v_{max}$ (cm$^{-1}$): 1696, 1636, 1607, 1517 NMR (270 MHz; DMSO-d$_6$) δ (ppm): 9.79(1H, s), 7.62(2H, d, J=8.3 Hz), 7.58(1H, d, J=15.8 Hz), 7.08(1H, d, J=15.8 Hz), 6.81 (2H, d, J=8.3Hz), 4.07 (2H, q, J=6.9 Hz), 3.99 (3H, s), 3.92 (2H, q, J=6.9 Hz), 1.26 (3H, t, J=6.9 Hz), 1.13(3H, t, J=6.9 Hz)

Reference Example 182

(E)-8-(4-Benzyloxystyryl)-1,3-diethyl-7-methylxanthine (Compound 185)

Compound 184 (100 mg, 0.29 mmol) obtained in Reference Example 181 was dissolved in 2 ml of dimethylformamide. To the solution were added 162 mg (1.17 mmol) of potassium carbonate and 0.28 ml (2.35 mmol) of benzyl bromide, and the mixture was stirred at 80° C. for 2.5 hours. Water was added thereto under ice cooling to dissolve potassium carbonate and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was recrystallized from hexane/ethyl acetate to give 67 mg (yield 53%) of Compound 185 as yellow needles.

Melting Point: 184.7°–185.4° C. Elemental Analysis: $C_{25}H_{26}N_4O_3$ Calcd. (%): C, 69.75; H, 6.08; N, 13.01 Found (%): C, 69.70; H, 6.26; N, 12.79 IR (KBr) $v_{max}$ (cm$^{-1}$): 1688, 1655, 1513, 1245 NMR (270 MHz; CDCl$_3$) δ (ppm): 7.74(1H, d, J=15.8 Hz), 7.53 (2H, d, J=8.9 Hz), 7.47–7.32 (5H, m), 7.01 (2H, d, J=8.9 Hz), 6.78 (1H, d, J=15.8 Hz), 5.11 (2H, s), 4.21 (2H, q, J=6.9 Hz), 4.09 (2H, q, J=6.9 Hz), 4.04 (3H, s), 1.38(3H, t, J=6.9 Hz), 1.26(3H, t, J=6.9 Hz)

Reference Example 183

(E)-8-[4-(4-Bromobutoxy)styryl]-1,3-diethyl-7-methylxanthine (Compound 186)

Compound 184 (200 mg, 0.59 mmol) obtained in Reference Example 181 was dissolved in 4 ml of dimethylformamide. To the solution were added 163 mg (1.18 mmol) of potassium carbonate and 0.56 ml (1.18 mmol) of 1,4-dibromobutane, and the mixture was stirred at 50° C. for 4 hours. Water was added thereto under ice cooling to dissolve potassium carbonate and the deposited crystals were collected by filtration. The obtained crude crystals were recrystallized from hexane/ethyl acetate to give 170 mg (yield 61%) of Compound 186 as pale yellow grains.

Melting Point: 174.8°–176.4° C. Elemental Analysis: $C_{22}H_{27}BrN_4O_3$ Calcd. (%): C, 55.59; H, 5.72; N, 11.79 Found (%): C, 55.68; H, 5.85; N, 11.69 IR (KBr) $v_{max}$ (cm$^{-1}$): 1688, 1656, 1515, 1244 NMR (270 MHz; CDCl$_3$) δ (ppm): 7.74(1H, d, J=15.8 Hz), 7.53 (2H, d, J=8.9 Hz), 6.92 (2H, d, J=8.9 Hz), 6.77 (1H, d, J=15.8 Hz), 4.21(2H, q, J=6.9 Hz), 4.13–4.02 (4H, m), 4.04(3H, s), 3.50(2H, t, J=6.6 Hz), 2.14–1.93 (4H, m), 1.38(3H, t, J=6.9 Hz), 1.26(3H, t, J=6.9 Hz)

Reference Example 184

(E)-8-[4-(4-Azidobutoxy)styryl]-1,3-diethyl-7-methylxanthine (Compound 187)

Compound 186 (235 mg, 0.49 mmol) obtained in Reference Example 183 was dissolved in 10 ml of dimethylformamide. To the solution was added 161 mg (2.48 mmol) of sodium azide, and the mixture was stirred at 80° C. for 3 hours. Water was added thereto under ice cooling and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was purified by silica gel column chromatography (eluent: chloroform), followed by recrystallization from hexane/ethyl acetate to give 216 mg (yield quant.) of Compound 187 as pale yellow grains.

Melting Point: 158.5°–158.9° C. MS-EI m/e: 437 (M$^+$) Elemental Analysis: $C_{22}H_{27}N_7O_3$ Calcd. (%): C, 60.40; H, 6.22; N, 22.41 Found (%): C, 60.15; H, 6.31; N, 22.32 IR (KBr) $v_{max}$ (cm$^{-1}$): 2094, 1653, 1605, 1543, 1515 NMR (270 MHz; CDCl$_3$) δ (ppm): 7.75(1H, d, J=15.5 Hz), 7.53 (2H, d, J=8.6 Hz), 6.92 (2H, d, J=8.6 Hz), 6.77 (1H, d, J=15.5 Hz), 4.21(2H, q, J=6.9 Hz), 4.13–3.69 (4H, m), 4.04 (3H, s), 3.39 (2H, t, J=6.6 Hz), 1.93–1.79(4H, m), 1.38(3H, t, J=6.9 Hz), 1.26(3H, t, J=6.9 Hz)

Reference Example 185

(E)-8-[4-(4-Aminobutoxy)styryl]-1,3-diethyl-7-methylxanthine (Compound 188)

Compound 187 (75 mg, 0.17 mmol) obtained in Reference Example 184 was dissolved in 7.5 ml of tetrahydrofuran. To the solution was added 90 mg (0.34 mmol) of triphenylphosphine, and the mixture was heated under reflux for 3 hours. Water (5 ml) was added thereto and the mixture was heated under reflux for further one hour. After cooling, a 2N aqueous solution of sodium hydroxide was added thereto, and the mixture was extracted with chloroform and dried over anhydrous sodium sulfate, followed by evaporation under reduced pressure. The residue was purified by silica gel column chromatography (eluent: chloroform/methanol/triethylamine) to give 74 mg (yield quant.) of Compound 188. The obtained crude crystals were further recrystallized from 2-propanol/water.

Melting Point: 212.1°–214.5° C. MS-EI m/e: 411 (M$^+$) IR (KBr) $v_{max}$ (cm$^{-1}$): 1692, 1649, 1606, 1544, 1515 NMR (270 MHz; DMSO-d$_6$) δ (ppm): 7.74(2H, d, J=8.6 Hz), 7.62(1H, d, J=16.2 Hz), 7.20(1H, d, J=16.2 Hz), 6.98 (2H, d, J=8.6 Hz), 4.08–3.88(6H, m), 4.02(3H, s), 2.83–2.74 (2H, m), 1.82–1.59(4H, m), 1.26(3H, t, J=6.9 Hz), 1.13 (3H, t, J=6.9 Hz)

Reference Example 186

(E)-8-(4-Ethoxycarbonylmethoxystyryl)-1,3-diethyl-7-methylxanthine (Compound 189)

Compound 184 (300 mg, 0.88 mmol) obtained in Reference Example 181 was dissolved in 10 ml of dimethylformamide. To the solution were added 731 mg (5.29 mmol) of potassium carbonate and 0.47 ml (4.41 mmol) of ethyl chloroacetate, and the mixture was stirred at room temperature for 2 hours. Water was added thereto to dissolve potassium carbonate and the deposited crystals were collected by filtration. The collected crude crystals were dissolved in chloroform, washed with a saturated aqueous solution of sodium chloride and dried over anhydrous sodium sulfate, followed by evaporation under reduced pressure. The residue was recrystallized from hexane/ethyl acetate to give 341 mg (yield 91%) of Compound 189 as pale yellow needles.

Melting Point: 191.8°–192.2° C. MS-E1 m/e: 426 (M$^+$) IR (KBr) $v_{max}$ (cm$^{-1}$): 1688, 1658, 1650, 1514, 1440 NMR (270 MHz; CDCl$_3$) δ (ppm): 7.74(1H, d, J=15.8 Hz), 7.54 (2H, d, J=8.6 Hz), 6.94 (2H, d, J=8.6 Hz), 6.79 (1H, d, J=15.8 Hz), 4.66(2H, s), 4.29(2H, q, J=6.9 Hz), 4.21 (2H, q, J=6.9 Hz), 4.09 (2H, q, J=6.9 Hz), 4.04 (3H, s), 1.38 (3H, t, J=6.9 Hz), 1.31 (3H, t, J=6.9 Hz), 1.26(3H, t, J=6.9 Hz)

Reference Example 187

(E)-8-(4-Carboxymethoxystyryl)-1,3-diethyl-7-methylxanthine (Compound 190)

Compound 189 (200 mg, 0.47 mmol) obtained in Reference Example 186 was dissolved in a mixed solvent of 4 ml of tetrahydrofuran, 4 ml of ethanol, and 2 ml of water. To the solution was added 98 mg (2.34 mmol) of lithium hydroxide monohydrate, and the mixture was stirred at room temperature for one hour. To the reaction solution was added 2N hydrochloric acid, and the mixture was extracted with chloroform and dried over anhydrous sodium sulfate, followed by evaporation under reduced pressure. The residue was purified by silica gel column chromatography (eluent: chloroform/methanol/acetic acid) to give 40 mg (yield 21%) of Compound 190 as a pale yellow solid.

Melting Point: 267.5°–269.0° C. MS-EI m/e: 398 (M$^+$) IR (KBr) $v_{max}$ (cm$^{-1}$): 1684, 1653, 1647, 1515 NMR (270 MHz; DMSO-d$_6$) δ (ppm): 7.74(2H, d, J=8.6 Hz), 7.62(1H, d, J=15.8 Hz), 7.20(1H, d, J=15.8 Hz), 6.96 (2H, d, J=8.6 Hz), 4.70(2H, s), 4.07(2H, q, J=6.9 Hz), 4.01 (3H, s), 3.92 (2H, q, J=6.9 Hz), 1.26 (3H, t, J=6.9 Hz), 1.13(3H, t, J=6.9 Hz)

Reference Example 188

(E)-1,3-Diethyl-8-(3-phenoxystyryl)xanthine (Compound 191)

Substantially the same procedure as in Reference Example 70 was repeated using 3.00 g (15.1 mmol) of 5,6-diamino-1,3-diethyluracil and 4.00 g (16.7 mmol) of 3-phenoxycinnamic acid. Then, the resultant crude crystals were recrystallized from dioxane/water to give 3.82 g (yield of Compound 191 as pale yellow needles.

Melting Point: 241.4°–243.4° C. Elemental Analysis: $C_{23}H_{22}N_4O_3$ Calcd. (%): C, 68.64; H, 5.51; N, 13.92 Found (%): C, 68.26; H, 5.59; N, 13.79 IR (KBr) $v_{max}$ (cm$^{-1}$): 1640, 1579, 1492, 1265 NMR (270 MHz; DMSO-d$_6$) δ (ppm): 13.52(1H, brs), 7.87 (1H, d, J=2.0 Hz), 7.63 (1H, dd, J=8.4, 2.0 Hz), 7.56 (1H, d, J=16.3 Hz), 7.16(1H, d, J=8.4 Hz), 6.95(1H, d, J=16.3 Hz), 4.06(2H, q, J=6.9 Hz), 3.93(2H, q, J=6.9 Hz), 3.89(3H, s), 1.26(3H, t, J=6.9 Hz), 1.14 (3H, t, J=6.9 Hz)

Reference Example 189

(E)-1,3-Diethyl-7-methyl-8-(3-phenoxystyryl)xanthine (Compound 192)

Substantially the same procedure as in Reference Example 1 was repeated using 2.00 g (4.97 mmol) of Compound 191 obtained in Reference Example 188 in place of Compound B. Then, the resultant crude crystals were recrystallized from hexane/ethyl acetate to give 1.78 g (yield 86%) of Compound 192 as yellow needles.

Melting Point: 205.1°–205.9° C. Elemental Analysis: $C_{24}H_{24}N_4O_3$ Calcd. (%): C, 69.22; H, 5.81; N, 13.45 Found (%): C, 69.02; H, 5.80; N, 13.48 IR (KBr) $v_{max}$ (cm$^{-1}$): 1692, 1652, 1492, 1241 NMR (270 MHz; CDCl$_3$) δ (ppm): 7.74(1H, d, J=15.8 Hz), 7.40–6.98(9H, m), 6.88(1H, d, J=15.8 Hz), 4.20(2H, q, J=6.9 Hz), 4.09(2H, q, J=6.9 Hz), 4.04(3H, s), 1.37(3H, t, J=6.9 Hz), 1.26(3H, t, J=6.9 Hz)

Reference Example 190

(E)-1,3-Diethyl-8-(4-hydroxystyryl)xanthine (Compound 193)

Substantially the same procedure as in Reference Example 181 was repeated using 500 mg (7.02 mmol) of Compound 145 obtained in Reference Example 142. Then, the resultant crude crystals were recrystallized from dioxane/water to give 430 mg (yield 98%) of Compound 193 as pale yellow needles.

Melting Point: >270° C. Elemental Analysis: $C_{17}H_{18}N_4O_3$ Calcd. (%): C, 62.57; H, 5.56; N, 17.17 Found (%): C, 62.60; H, 5.50; N, 17.07 IR (KBr) $v_{max}$ (cm$^{-1}$): 1674, 1634, 1520, 1488 NMR (270 MHz; DMSO-d$_6$) δ (ppm): 13.34(1H, brs), 9.77 (1H, s), 7.56(1H, d, J=16.2 Hz), 7.46(2H, d, J=8.6 Hz), 6.81 (2H, d, J=8.6 Hz), 6.80 (1H, d, J=16.2 Hz), 4.06(2H, q, J=6.9 Hz), 3.94(2H, q, J=6.9 Hz), 1.26(3H, t, J=6.9 Hz), 1.14(3H, t, J=6.9 Hz)

Reference Example 191

(E)-1,3-Diethyl-8-(4-hydroxy-2,3-dimethylstyryl)-7-methylxanthine (Compound 194)

Substantially the same procedure as in Reference Example 179 was repeated using 500 mg (1.31 mmol) of Compound 82 obtained in Reference Example 79. Then, the resultant crude crystals were recrystallized from 2-propanol to give 290 mg (yield 60%) of Compound 194 as a pale yellow powder.

Melting Point: 240.2°–242.0° C. MS-EI m/e: 368 (M$^+$) IR (KBr) $v_{max}$ (cm$^{-1}$): 1683, 1656, 1586, 1460 NMR (270 MHz; DMSO-d$_6$) δ (ppm): 10.20(1H, brs), 9.64 (1H, brs), 7.92(1H, d, J=15.6 Hz), 7.57(1H, d, J=8.7 Hz), 6.97 (1H, d, J=15.6 Hz), 6.74 (1H, d, J=8.7 Hz), 4.07 (2H, q, J=6.9 Hz), 3.99 (3H, s), 3.91 (2H, q, J=6.9 Hz), 2.29(3H, s), 2.10(3H, s), 1.26 (3H, t, J=6.9 Hz), 1.13(3H, t, J=6.9 Hz)

Industrial Applicability

According to the present invention, there can be provided an excellent antidepressant.

We claim:

1. A method of treating depression which comprises administering to a patient suffering from depression an effective amount of a xanthine derivative of the following Formula (I):

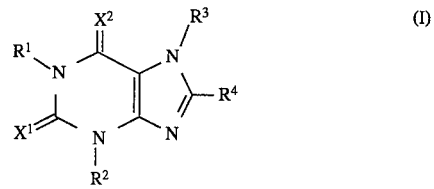

in which $R^1$, $R^2$ and $R^3$ independently represent hydrogen, lower alkyl, lower alkenyl or lower alkynyl; $R^4$ represents cycloalkyl, —(CH$_2$)$_n$—$R^5$ (in which $R^5$ represents substituted or unsubstituted aryl or a substituted or unsubstituted heterocyclic group; and n is an integer of 0 to 4), or

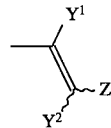

(in which $Y^1$ and $Y^2$ independently represent hydrogen, halogen or lower alkyl; and Z represents substituted or unsubstituted aryl,

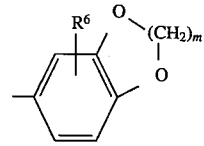

(in which $R^6$ represents hydrogen, hydroxy, lower alkyl, lower alkoxy, halogen, nitro or amino; and m represents an integer of 1 to 3), or a substituted or unsubstituted heterocyclic group); and $X^1$ and $X^2$ independently represent O or S.

2. A method of treating depression according to claim 1, in which $R^1$, $R^2$ and $R^3$ independently represent hydrogen, lower alkyl, allyl or propargyl; and $Y^1$ and $Y^2$ independently represent hydrogen, fluorine or methyl.

* * * * *

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

ABSTRACT

Line 14, "alkenyl;" should read --alkenyl or lower alkynyl;--.

COLUMN 1

Line 38, "3,,4,5-trimethoxyphenyl" should read --3,4,5-trimethoxyphenyl.--.
    Line 51, Y2b" should read --$Y^{2b}$--.

COLUMN 3

Line 1, "all" should read --di--.
    Line 16, "arid" should read --and--.
    Line 28, "(i)" should read --(I)--.

COLUMN 6

Line 31, "substituent (s)]" should read --substituent(s)]--.
    Line 45, "substituent (s)]" should read --substituent(s)]--.
    Line 66, "formulae;," should read --formulae,--.

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 8

Line 3, "inert:" should read --inert--.

COLUMN 9

Line 7, "substituent (s)]" should read
      --substituent(s)]--.

COLUMN 10

Line 17, "arid" should read --and--.

COLUMN 12

Line 25, "(E)-B-" should read --(E)-8- --.

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

<u>COLUMN 14</u>

After Line 16 insert:

161  (E)-8-(3-bromostyryl)-1,3-diethylxanthine 162  (E)-8-(3-bromostyryl)-1,3-diethyl-7-methylxanthine 163  (E)-1,3-diethyl-8-(3-trifluoromethylstyryl)-xanthine 164  (E)-1,3-diethyl-7-methyl-8-(3-trifluoromethyl-styryl)xanthine 165  (E)-8-(2-bromo-4,5-methylenedioxystyryl)-1,3-diethylxanthine 166  (E)-8-(2-bromo-4,5-methylenedioxystyryl)-1,3-diethyl-7-methylxanthine 167  (E)-1,3-diethyl-8-(2-fluorostyryl)xanthine 168  (E)-1,3-diethyl-8-(2-fluorostyryl)-7-methyl-xanthine

UNITED STATES PATENT AND TRADEMARK OFFICE
CERTIFICATE OF CORRECTION

PATENT NO. : 5,543,415

DATED : August 6, 1996

INVENTOR(S): FUMIO SUZUKI ET AL.

It is certified that error appears in the above-identified patent and that said Letters Patent is hereby corrected as shown below:

169  (E)-8-[4-(N,N-dimethylamino)styryl]-1,3-diethylxanthine 170  (E)-1,3-diethyl-8-(4-phenylstyryl)xanthine 171  (E)-1,3-diethyl-7-methyl-8-(4-phenylstyryl)-xanthine 172  (E)-1,3-diethyl-8-(3-fluoro-4-methoxystyryl)-xanthine 173  (E)-1,3-diethyl-8-(3-fluoro-4-methoxystyryl)-7-methylxanthine 174  (E)-1,3-diethyl-8-(4-methoxy-3-methylstyryl)-xanthine 175  (E)-1,3-diethyl-8-(4-methoxy-3-methylstyryl)-7-methylxanthine 176  (E)-8-(3-chloro-4-fluorostyryl)-1,3-diethylxanthine

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 42

Line 64, "15)" should read --(15)--.
    Line 66, "15)" should read --(15)--.

COLUMN 43

Line 9, "(15" should read --(15)--.
    Line 11, "(15" should read --(15)--.
    Line 14, "8.36" should read --8.35--.

UNITED STATES PATENT AND TRADEMARK OFFICE
CERTIFICATE OF CORRECTION

PATENT NO. : 5,543,415

DATED : August 6, 1996

INVENTOR(S): FUMIO SUZUKI ET AL.

It is certified that error appears in the above-identified patent and that said Letters Patent is hereby corrected as shown below:

COLUMN 43

After Line 38 insert:

| 82  | 0.63 | 6.5 ± 2.46 (15) | 55.1 ± 12.58** (15) | 8.5  |
|-----|------|-----------------|---------------------|------|
| 84  | 10   | 2.9 ± 2.51 (15) | 16.1 ± 3.70** (15)  | 6.9  |
| 86  | 10   | 5.0 ± 1.55 (15) | 51.5 ± 8.73*** (15) | 10.3 |
| 86  | 2.5  | 5.0 ± 1.55 (15) | 30.9 ± 6.39** (15)  | 6.2  |
| 88  | 10   | 5.4 ± 2.03 (15) | 40.9 ± 7.33*** (15) | 7.6  |
| 88  | 2.5  | 5.4 ± 2.03 (15) | 54.7 ± 10.76*** (15)| 10.1 |
| 90  | 10   | 3.6 ± 1.14 (15) | 18.7 ± 5.07* (15)   | 5.2  |
| 92  | 10   | 6.4 ± 2.98 (10) | 55.4 ± 14.66** (10) | 8.7  |
| 106 | 10   | 4.1 ± 2.60 (15) | 22.3 ± 8.04* (15)   | 5.4  |

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

| 108 | 2.5 | 5.6 ± 2.54 (15) | 25.6 ± 5.59** (15) | 4.6 |
|---|---|---|---|---|
| 110 | 10 | 1.5 ± 0.74 (15) | 42.5 ± 11.37** (15) | 28.3 |
| 110 | 2.5 | 2.3 ± 0.92 (15) | 36.6 ± 7.72*** (15) | 27.9 |

COLUMN 43

Line 46, "52.2± 11.79 48" to read --59.5± 13.61 55--.

After Line 47 insert:

| 136 | 10 | 2.6 ± 1.69 (10) | 16.1 ± 5.26* (10) | 6.2 |
|---|---|---|---|---|
| 140 | 10 | 10.8 ± 7.51 (10) | 52.2 ± 11.79** (10) | 4.8 |
| 146 | 10 | 2.9 ± 1.65 (10) | 62.3 ± 14.16** (10) | 21.5 |

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 46

Line 22, "ill" should read --111--.

COLUMN 47

Line 2, "acceptable;" should read --acceptable--.

COLUMN 49

Line 32, "2,602;795)" should read --2,602,795)--.
   Line 57, "$C_{2.1}$" should read --$C_{21}$--.

COLUMN 51

Line 26, "2N.sodium" should read --2N sodium--.

COLUMN 52

Line 53, "J=16.0" (first occurrence) should not be a paragraph.

COLUMN 53

Line 63, "Substantially-the" should read --Substantially the--.

UNITED STATES PATENT AND TRADEMARK OFFICE
CERTIFICATE OF CORRECTION

PATENT NO. : 5,543,415

DATED : August 6, 1996

INVENTOR(S): FUMIO SUZUKI ET AL.

It is certified that error appears in the above-identified patent and that said Letters Patent is hereby corrected as shown below:

COLUMN 54

Line 45, "C, 4.84;" should read --C, 64.84;--.

COLUMN 56

Line 53, "61.944" should read --61.94;--.

COLUMN 59

Line 35, "7.7 0 g" should read --7.70g--.
Line 36, "(yield" should read --(yield 81%)--.
Line 39, $(cm^{-1})$:" should read --$(cm^{-1})$:--
Line 43, "(3H, s," should read --(3H, s),--.

COLUMN 61

Line 45, "6.2.6;" should read --6.26;--.

COLUMN 62

Line 17, "62.0 g;" should read --62.09;--.
Line 22, "e," should read --t,--.

COLUMN 63

Line 10, "68%" should read --68%)--.

UNITED STATES PATENT AND TRADEMARK OFFICE
CERTIFICATE OF CORRECTION

PATENT NO. : 5,543,415

DATED : August 6, 1996

INVENTOR(S): FUMIO SUZUKI ET AL.

It is certified that error appears in the above-identified patent and that said Letters Patent is hereby corrected as shown below:

COLUMN 65

Line 60, "64%" should read --64%)--.

COLUMN 67

Line 7, "q,:" should read --q,--.
    Line 50, "1.90-3.65" should read --1.90-1.65--.

COLUMN 69

Line 28, "pound" should read --pound 62--.

COLUMN 70

Line 44, "3.80(3H; s)," should read --3.80 (3H, s),--.
    Line 61, "6.74.;" should read --6.74;--.

COLUMN 71

Line 38, "(yield" should read --(yield 54%)--.

COLUMN 72

Line 49, "73," should read --75,--.

UNITED STATES PATENT AND TRADEMARK OFFICE
CERTIFICATE OF CORRECTION

PATENT NO. : 5,543,415

DATED : August 6, 1996

INVENTOR(S): FUMIO SUZUKI ET AL.

It is certified that error appears in the above-identified patent and that said Letters Patent is hereby corrected as shown below:

COLUMN 74

Line 40, "Compound" should read --Compound 78--.
Line 60, "57%" should read --57%)--.
Line 65, "12.3 9" should read --12.39--.

COLUMN 75

Line 15, "Compound" should read --Compound 80--.

COLUMN 76

Line 67, "Compound" should read --Compound 85--.

COLUMN 77

Line 3, "Compound" should read --Compound 86--.

COLUMN 78

Line 10, "8.7" should read --87--.
Line 59, "Compound" should read --Compound 92--.

COLUMN 79

Line 46, "retool)" should read --mmol)--.

UNITED STATES PATENT AND TRADEMARK OFFICE
CERTIFICATE OF CORRECTION

PATENT NO.  : 5,543,415

DATED       : August 6, 1996

INVENTOR(S) : FUMIO SUZUKI ET AL.

It is certified that error appears in the above-identified patent and that said Letters Patent is hereby corrected as shown below:

COLUMN 80

Line 21, "(yield" should read --(yield 41%)--.

COLUMN 82

Line 28, "3 64" should read --3.64--.

COLUMN 83

Line 27, "-24.2.6°C." should read --242.6°C.--.
Line 42, "pound" should read --pound 107--.

COLUMN 85

Line 13, "C, 51 57; H, 4 57;" should read
    --C, 51.57; H, 4.57;--.
Line 34, "Compound" should read --Compound 114--.

COLUMN 86

Line 7, "Compound" should read --Compound 115--.

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 87

Line 27, "7.03(1 H, s)," should read --7.03(1H,s),--.
Line 57, "Compound" should read --Compound 121--.
Line 60, "Compound" should read --Compound 122--.
Line 61, "2.59.9°" should read --259.9°--.

COLUMN 89

Line 27, "retool)" should read --mmol)--.
Line 30, "40%" should read --40%)--.

COLUMN 91

Line 42, "(SH, m)," should read --(5H, m),--.

COLUMN 93

Line 61, "$C_{18}H_{19}{}^{BrN}{}_4O_2.O.25H_2O$" should read
   --$C_{18}H_{19}BrN_4O_2.O.25H_2O$--.

COLUMN 94

Line 1, "14" should read --140--.
Line 67, "154" should read --145--.

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 95

Line 21, "(yield" should read --(yield 53%)--.
    Line 44, "1.23.6°" should read --123.6°--.

COLUMN 96

Line 55, "Compound" should read --Compound 151--.
    Line 58, "Compound" should read --Compound 152--.

COLUMN 97

Line 49, "63%" should read --63%)--.

COLUMN 98

Line 37, "pound" should read --pound 157--.

COLUMN 100

Line 27, "Compound" should read --Compound 163--.

COLUMN 101

Line 21, "(yield" should read --(yield 41%)--.

UNITED STATES PATENT AND TRADEMARK OFFICE
CERTIFICATE OF CORRECTION

PATENT NO. : 5,543,415

DATED : August 6, 1996

INVENTOR(S) : FUMIO SUZUKI ET AL.

It is certified that error appears in the above-identified patent and that said Letters Patent is hereby corrected as shown below:

COLUMN 102

Line 13, "(yield" should read --(yield 39%)--.

COLUMN 104

Line 30, "Compound" should read --Compound 177--.

COLUMN 105

Line 29, "J=1 6.6" should read --J=16.6--.

COLUMN 106

Line 17, "Compound" should read --Compound 182--.
    Line 18, "(yield" should read --(yield 76%)--.
    Line 37, "N" should read --2N--.

Signed and Sealed this

First Day of July, 1997

Attest:

BRUCE LEHMAN

*Attesting Officer*       *Commissioner of Patents and Trademarks*